United States Patent
Lee

(10) Patent No.: US 8,310,232 B2
(45) Date of Patent: *Nov. 13, 2012

(54) NMR DEVICE FOR DETECTION OF ANALYTES

(75) Inventor: W. David Lee, West Newton, MA (US)

(73) Assignee: T2 Biosystems, Inc., Lexington, MA (US)

( * ) Notice: Subject to any disclaimer, the term of this patent is extended or adjusted under 35 U.S.C. 154(b) by 367 days.

This patent is subject to a terminal disclaimer.

(21) Appl. No.: 12/844,680

(22) Filed: Jul. 27, 2010

(65) Prior Publication Data

US 2011/0021374 A1    Jan. 27, 2011

Related U.S. Application Data

(63) Continuation of application No. 12/231,426, filed on Sep. 2, 2008, now Pat. No. 8,102,176, which is a continuation of application No. 11/513,503, filed on Aug. 31, 2006, now Pat. No. 7,564,245.

(60) Provisional application No. 60/713,176, filed on Aug. 31, 2005.

(51) Int. Cl.
*G01V 3/00* (2006.01)

(52) U.S. Cl. ............................................... 324/307

(58) Field of Classification Search .......... 324/300–322; 600/407–445; 435/7, 6, 5; 422/69; 436/526
See application file for complete search history.

(56) References Cited

U.S. PATENT DOCUMENTS

| | | | |
|---|---|---|---|
| 4,101,435 A | 7/1978 | Hasegawa et al. |
| 4,452,773 A | 6/1984 | Molday |
| 4,672,040 A | 6/1987 | Josephson |
| 4,920,061 A | 4/1990 | Poynton et al. |
| 5,136,095 A | 8/1992 | Tarnowski et al. |
| 5,164,297 A | 11/1992 | Josephson et al. |
| 5,204,457 A | 4/1993 | Maruno et al. |
| 5,254,460 A | 10/1993 | Josephson et al. |
| 5,262,176 A | 11/1993 | Palmacci et al. |
| 5,424,419 A | 6/1995 | Hasegawa et al. |
| 5,445,970 A | 8/1995 | Rohr |

(Continued)

FOREIGN PATENT DOCUMENTS

EP    0 859 491 A1    8/1998

(Continued)

OTHER PUBLICATIONS

Atanasijevic et al., "Calcium-Sensitive MRI Contrast Agents Based on Superparamagnetic Iron Oxide Nanoparticles and Calmodulin," *Proc. Natl. Acad. Sci. U.S.A.* 103(40): 14707-14712, 2006.

(Continued)

*Primary Examiner* — Brij Shrivastav
(74) *Attorney, Agent, or Firm* — Clark & Elbing LLP

(57) ABSTRACT

This invention relates generally to detection devices having one or more small wells each surrounded by, or in close proximity to, an NMR micro coil, each well containing a liquid sample with magnetic nanoparticles that self-assemble or disperse in the presence of a target analyte, thereby altering the measured NMR properties of the liquid sample. The device may be used, for example, as a portable unit for point of care diagnosis and/or field use, or the device may be implanted for continuous or intermittent monitoring of one or more biological species of interest in a patient.

67 Claims, 14 Drawing Sheets

U.S. PATENT DOCUMENTS

| | | | |
|---|---|---|---|
| 5,445,971 | A | 8/1995 | Rohr |
| 5,492,814 | A | 2/1996 | Weissleder |
| 5,508,164 | A | 4/1996 | Kausch et al. |
| 5,512,439 | A | 4/1996 | Hornes et al. |
| 5,578,325 | A | 11/1996 | Domb et al. |
| 5,637,469 | A | 6/1997 | Wilding et al. |
| 5,677,133 | A | 10/1997 | Oberhardt |
| 5,679,323 | A | 10/1997 | Menz et al. |
| 5,705,628 | A | 1/1998 | Hawkins |
| 5,711,871 | A | 1/1998 | Miltenyi |
| 5,773,307 | A | 6/1998 | Colin et al. |
| 5,801,003 | A | 9/1998 | Shimamura et al. |
| 5,898,071 | A | 4/1999 | Hawkins |
| 5,925,573 | A | 7/1999 | Colin et al. |
| 5,973,138 | A | 10/1999 | Collis |
| 6,007,845 | A | 12/1999 | Domb et al. |
| 6,013,188 | A | 1/2000 | Terstappen et al. |
| 6,033,574 | A | 3/2000 | Siddiqi |
| 6,097,188 | A | 8/2000 | Sweedler et al. |
| 6,136,549 | A | 10/2000 | Feistel |
| 6,159,378 | A | 12/2000 | Holman et al. |
| 6,165,378 | A | 12/2000 | Maruno et al. |
| 6,194,900 | B1 | 2/2001 | Freeman et al. |
| 6,228,268 | B1 | 5/2001 | Siddiqi |
| 6,294,342 | B1 | 9/2001 | Rohr et al. |
| 6,297,062 | B1 | 10/2001 | Gobinski |
| 6,342,396 | B1 | 1/2002 | Perrin et al. |
| 6,361,944 | B1 | 3/2002 | Mirkin et al. |
| 6,500,343 | B2 | 12/2002 | Siddiqi |
| 6,548,311 | B1 | 4/2003 | Knoll |
| 6,599,498 | B1 | 7/2003 | Groman et al. |
| 6,630,355 | B1 | 10/2003 | Pivarnik et al. |
| 6,767,635 | B1 | 7/2004 | Bahr et al. |
| 6,774,635 | B1 | 8/2004 | Gerald, II et al. |
| 6,788,061 | B1 | 9/2004 | Sweedler et al. |
| 6,822,452 | B2 | 11/2004 | Ham et al. |
| 6,866,838 | B1 | 3/2005 | Mondain-Monval et al. |
| 7,001,589 | B2 | 2/2006 | Mondain-Monval et al. |
| 7,018,849 | B2 | 3/2006 | Piasio et al. |
| 7,093,482 | B2 | 8/2006 | Berndt |
| 7,200,430 | B2 | 4/2007 | Thomas et al. |
| 7,217,457 | B2 | 5/2007 | Elaissari et al. |
| 7,332,353 | B2 | 2/2008 | Baudry et al. |
| 7,345,479 | B2 | 3/2008 | Park et al. |
| 7,553,542 | B2 | 6/2009 | Ou et al. |
| 7,564,245 | B2 | 7/2009 | Lee |
| 7,781,228 | B2 | 8/2010 | Menon et al. |
| 7,829,350 | B2 | 11/2010 | Josephson et al. |
| 8,102,176 | B2 * | 1/2012 | Lee ............... 324/309 |
| 2003/0092029 | A1 | 5/2003 | Josephson et al. |
| 2003/0137971 | A1 | 7/2003 | Gibson et al. |
| 2003/0174384 | A1 | 9/2003 | Halas et al. |
| 2003/0222648 | A1 | 12/2003 | Fan |
| 2006/0053870 | A1 | 3/2006 | Berndt |
| 2006/0269965 | A1 | 11/2006 | Josephson et al. |
| 2007/0116600 | A1 | 5/2007 | Kochar et al. |
| 2007/0116602 | A1 | 5/2007 | Lee |
| 2007/0166730 | A1 | 7/2007 | Menon et al. |
| 2008/0305048 | A1 | 12/2008 | Josephson et al. |
| 2009/0099342 | A1 | 4/2009 | Braconnot et al. |
| 2009/0146658 | A1 | 6/2009 | McDowell et al. |
| 2010/0120174 | A1 | 5/2010 | Josephson et al. |
| 2010/0301858 | A1 * | 12/2010 | Lowery et al. ............ 324/309 |
| 2011/0018538 | A1 * | 1/2011 | Lee ............... 324/309 |
| 2011/0020787 | A1 * | 1/2011 | Lee ............... 435/5 |
| 2011/0020788 | A1 * | 1/2011 | Lee ............... 435/5 |
| 2011/0020953 | A1 * | 1/2011 | Lee ............... 436/526 |
| 2012/0100546 | A1 * | 4/2012 | Lowery et al. ............ 435/6.12 |
| 2012/0107839 | A1 * | 5/2012 | Lee ............... 435/7.23 |
| 2012/0164644 | A1 * | 6/2012 | Neely et al. ............ 435/6.11 |

FOREIGN PATENT DOCUMENTS

| | | |
|---|---|---|
| JP | 2001-269326 | 10/2001 |
| JP | 2002-152251 A | 5/2002 |
| JP | 2008-542684 | 11/2008 |
| WO | WO 90/06045 A2 | 6/1990 |
| WO | WO 91/17428 A1 | 11/1991 |
| WO | WO 95/22963 A1 | 8/1995 |
| WO | WO 96/09313 A1 | 3/1996 |
| WO | WO 97/40181 A1 | 10/1997 |
| WO | WO 98/04740 A1 | 2/1998 |
| WO | WO 98/21587 A1 | 5/1998 |
| WO | WO 01/00876 A1 | 1/2001 |
| WO | WO 01/11360 | 2/2001 |
| WO | WO 01/19405 A2 | 3/2001 |
| WO | WO 02/098364 A2 | 12/2002 |
| WO | WO 2005/061724 A1 | 7/2005 |
| WO | WO 2005/099419 | 10/2005 |
| WO | WO 2006/122083 A2 | 11/2006 |
| WO | WO 2007/027843 A1 | 3/2007 |
| WO | WO 2008/057578 A1 | 5/2008 |

OTHER PUBLICATIONS

Costanzo et al., "Protein-Ligand Mediated Aggregation of Nanoparticles: A Study of Synthesis and Assembly Mechanism," *Chem. Mater.* 16(9): 1775-1785, 2004.

Demas et al., "Portable, Low-Cost NMR with Laser-Lathe Lithography Produced Microcoils," *J. Mag. Reson.* 189(1): 121-129, 2007.

Hatch and Stelter, "Magnetic Design Considerations for Devices and Particles Used for Biological High-Gradient Magnetic Separation (HGMS) Systems," *J. Magn. Magn. Mater.* 225(1-2): 262-276, 2001.

Inglis et al., "Microfluidic High Gradient Magnetic Cell Separation," *J. Appl. Physics* 99(8): 08K101-08K101-3, 2006.

Kriz et al., "Magnetic Permeability Measurements in Bioanalysis and Biosensors," *Anal. Chem.* 68(11): 1966-1970, 1996.

Kriz et al., "Advancements Towards Magneto Immunoassays," *Biosens. Bioelectron.* 13(7-8): 817-823, 1998.

Magin et al., "Miniature Magnetic Resonance Machines," *IEEE Spectrum* 34(10): 51-61, 1997.

Malba et al., "Laser-Lathe Lithography—A Novel Method for Manufacturing Nuclear Magnetic Resonance Microcoils," *Biomed. Microdevices* 5(1): 21-27, 2003.

Massin et al., "Planar Microcoil-Based Microfluidic NMR Probes," *J. Magn. Reson.* 164(2): 242-255, 2003.

Massin et al., "Planar Microcoil-Based Magnetic Resonance Imaging of Cells," *Transducers, Solid-State Sensors, Actuators and Microsystems, 12$^{th}$ International Conference* 2(9): 967-970, 2003.

Peck et al., "RF Microcoils Patterned Using Microlithographic Techniques for Use as Microsensors in NMR," *Conf. Proc. IEEE Eng. Med. Bio. Soc.* pp. 174-175, 1993.

Perez et al., "Viral-Induced Self Assembly of Magnetic Nanoparticles Allows the Detection of Viral Particles in Biological Media," *J. Am. Chem. Soc.* 125(34): 10192-10193, 2003.

Routley et al., "The HALO System—A Light Weight Portable Imaging System," *Magn. Reson. Imaging* 22(8): 1145-1151, 2004.

Shapiro et al., "Dynamic Imaging with MRI Contrast Agents: Quantitative Considerations," *Magn. Reson. Imaging* 24(4): 449-462, 2006.

Syms et al., "MEMS Helmoholtz Coils for Magnetic Resonance Imaging," *J. Micromech. Microeng.* 15(7): S1-S9, 2005.

Tong et al., "Coating Optimization of Superparamagnetic Iron Oxide Nanoparticles for High T2 Relaxivity," *Nano Lett.* 10(11): 4607-4613, 2010.

Weissleder et al., "Cell-Specific Targeting of Nanoparticles by Multivalent Attachment of Small Molecules," *Nat. Biotechnol.* 23(11): 1418-1423, 2005.

Wu et al., "$^1$H-NMR Spectroscopy on the Nanoliter Scale for Static and Online Measurements," *Anal. Chem.* 66(22): 3849-3857, 1994.

Office Action mailed May 1, 2008 in U.S. Appl. No. 11/513,503, Lee, W.D., filed Aug. 31, 2006.

Perez et al., "Use of Magnetic Nanoparticles as Nanosensors to Probe for Molecular Interactions," *Chembiochem Wiley-Vch Verlag*, 5(3): 261-264 (2004).

Perez et al., "Magnetic Relaxation Switches Capable of Sensing Molecular Interactions," *Nature Biotechnology*, 20(8): 816-820 (2002).

Gijs, "Magnetic Bead Handling on-chip: New Opportunities for Analytical Applications," *Microfluid Nanofluid*, 1: 22-40 (2004) XP002418117.

Fry, G. et al., "A New Approach to Template Purification for Sequencing Applications Using Paramagnetic Particles," *BioTechniques*, vol. 13, No. 1 (1992).

Högemann, D. et al., "Improvement of MRI Probes to Allow Efficient Detection of Gene Expression," *Bioconjugate Chem*, vol. 11, No. 6, pp. 941-946 (2000).

Josephson, L. et al., "High-Efficiency Intracellular Magnetic Labeling with Novel Superparamagnetic-Tat Peptide Conjugates," *Bioconjugate Chem*, vol. 10, No. 2, pp. 186-191 (1999).

Josephson, L. et al., "Magnetic Nanosensors for the Detection of Oligonucleotide Sequences," *Agnew. Chem. Int. Ed.*, vol. 40, No. 17, pp. 3204-3206 (2001).

Lewin, M. et al., "Tat Peptide-Derivatized Magnetic Nanoparticles Allow in vivo Tracking and Recovery or Progenitor Cells," *Nature Biotechnology*, vol. 18, pp. 410-414 (Apr. 2000).

Perez et al., "DNA-Based Magnetic Nanoparticle Assembly Acts as a Magnetic Relaxation Nanoswitch Allowing Screening of DNA-Cleaving Agents," *J. Am. Chem. Soc.*, vol. 124, No. 12, pp. 2856-2857 (2002).

Kötitz et al., "Determination of the Binding Reaction Between Avidin and Biotin by Relaxation Measurements of Magnetic Nanoparticles," *Journal of Magnetism and Magnetic Materials*, 194: 62-68 (1999).

Niemeyer et al., "Self-Assembly of DNA-Streptavidin Nanostructures and their Use as Reagents in Immuno-PCR," *Nucleic Acid Research*, 27(23): 4553-4561 (1999).

Lowery, T.J. et al., "Single-Coil, Multisample, Proton Relaxation Method for Magnetic Relaxation Switch Assays," *Anal. Chem.* 80: 1118-1123 (2008); including Supplementary Information for Single-Coil, Multisample, Proton Relaxation Method for Magnetic Relaxation Switch Assays (pp. 1-5).

Boero, G. et al., "An NMR Magnetometer With Planar Microcoils and Integrated Electronics for Signal Detection and Amplification," *Sensors and Actuators* A 67:18-23 (1998).

Lee, C.S. et al., "Microelectromagnets for the Control of Magnetic Nanoparticles," *Appl. Phys. Lett.* 79(20):3308-3310 (2001).

Mäkiranta, J.J. and Lekkala, J.O., "Modeling and Simulation of Magnetic Nanoparticle Sensor," Master of Science Thesis, Tampere University of Technology, Oct. 13, 2004.

Mäkiranta, J.J. and Lekkala, J.O., "Modeling and Simulation of Magnetic Nanoparticle Sensor," Engineering in Medicine and Biology, $27^{th}$ Annual Conference, Shanghai, China, Sep. 1-4, pp. 1256-1259, (2005).

Massin, C. et al., "High-$Q$ Factor RF Planar Microcoils for Microscale NMR Spectroscopy," *Sensors and Actuators* A 97-98: 280-288 (2002).

Ramadan, Q. et al., "On-Chip Micro-Electromagnets for Magnet-Based Bio-Molecules Separation," *Journal of Magnetism and Magnetic Materials* 281: 150-172 (2004).

Renaud, L. et al., "Implantable Planar RF Microcoils for NMR Microspectroscopy," *Sensors and Actuators* A 99: 244-248 (2002).

Rida, A. et al., "Long-Range Transport of Magnetic Microbeads Using Simple Planar Coils Placed in a Uniform Magnetostatic Field," *Appl. Phys. Lett.* 83(12): 2396-2398 (2003).

Sillerud, L.O. et al., "H. NMR Detection of Superparamagnetic Nanoparticles at 1T Using a Microcoil and Novel Tuning Circuit," *Journal of Magnetic Resonance* 181: 181-190 (2006).

Wensink, H. et al., "High Signal to Noise Ratio in Low Field NMR on Chip Simulations and Experimental Results," *Micro Electro Mechanical Systems*, $17^{th}$ IEEE International Conference, Netherlands, pp. 407-410 (2004).

Zhang, X. et al., "A Probe Design for the Acquisition of Homonuclear, Heteronuclear, and Inverse Detected NMR Spectra From Multiple Samples," *Journal of Magnetic Resonance* 153: 254-258, (2001).

Vasseur, J.P. et al., "Inter-area and Inter-AS MPLS Traffic Engineering," Feb. 2004. IETF Standard-Working-Draft, Internet Engineering Task Force, IETF, CH.

Awduche, D. et al., "RSVP-TE: 1-14 Extensions to RSVP for LSP Tunnels," Dec. 2001. IETF Standard, Internet Engineering Task Force, IETF, CH.

Lee, C.Y. et al., "Exclude Routes—Extension to RSVP-TE," Dec. 2003. Internet Engineering Task Force, IETF, CH, Vol. Ccamp, No. 1.

Notification of Reasons for Rejection issued in Japanese Patent Application No. 2008-529259, dated Jun. 12, 2012.

* cited by examiner

FIG. 6B PANEL CHIP-MULTIPLE ASSAY

FIG. 6A SINGLE WELL CHIP

NMR DEVICE FOR DETECTION OF ANALYTES

RELATED APPLICATIONS

This application is a continuation of U.S. application Ser. No. 12/231,426, filed Sep. 2, 2008, which is a continuation of U.S. application Ser. No. 11/513,503, filed Aug. 31, 2006, now U.S. Pat. No. 7,564,245, which claims the benefit of U.S. Provisional Patent Application No. 60/713,176, filed Aug. 31, 2005, each of which is incorporated herein by reference.

FIELD OF THE INVENTION

This invention relates generally to devices for the detection of analytes. More particularly, in certain embodiments, the invention relates to a detection device having one or more small wells each surrounded by, or in close proximity to, an NMR micro coil, each well containing a liquid sample with magnetic nanoparticles that self-assemble or disperse in the presence of a target analyte, thereby altering the measured NMR properties of the liquid sample.

BACKGROUND OF THE INVENTION

Biocompatible magnetic nanosensors have been designed to detect molecular interactions in biological media. Upon target binding, these nanosensors cause changes in the spin-spin relaxation times of neighboring water molecules (or any solvent molecule with free hydrogens) of a sample, which can be detected by classical magnetic resonance (NMR/MRI) techniques. Thus, by using these nanosensors in a liquid sample, it is possible to detect the presence of an analyte at very low concentration—for example, small molecules, specific DNA, RNA, proteins, carbohydrates, organisms, and pathogens (e.g. viruses)—with sensitivity in the low femtomole range (from about 0.5 to about 30 fmol).

In general, magnetic nanosensors are superparamagnetic nanoparticles that bind or otherwise link to their intended molecular target to form clusters (aggregates) or nanoassemblies. It is thought that when superparamagnetic nanoparticles assemble into clusters and the effective cross sectional area becomes larger, the nanoassembly becomes more efficient at dephasing the spins of surrounding water (or other solvent) protons, leading to an enhancement of the measured relaxation rates (1/T2). Additionally, nanoassembly formation can be designed to be reversible (e.g., by temperature shift, chemical cleavage, pH shift, etc.) so that "forward" or "reverse" assays can be developed for detection of specific analytes. Forward (clustering) and reverse (declustering) types of assays can be used to detect a wide variety of biologically relevant materials. Furthermore, the spin-lattice relaxation time (T1) is considered independent of nanoparticle assembly formation and can be used to measure concentration in both nano-assembled and dispersed states within the same solution.

Examples of magnetic nanosensors are described in Perez et al., "Use of Magnetic Nanoparticles as Nanosensors to Probe for Molecular Interactions," *ChemBioChem*, 2004, 5, 261-264, and in U.S. Patent Application Publication No. US2003/0092029 (Josephson et al.), the texts of which are incorporated by reference herein, in their entirety. Examples of magnetic nanosensors include monocrystalline iron oxide nanoparticles from about 3 to about 5 nm in diameter surrounded with a dextran coating approximately 10 nm thick such that the average resulting particle size is from about 25 to about 30 nm.

More stably coated and amino-functionalized nanosensors can be prepared, for example, by cross-linking the dextran coating of the metal oxide particle core with epichlorohydrin, then treating with ammonia to provide functional amino groups. Aminated cross-linked iron oxide nanoparticles (amino-CLIO) have been made with 40 amino groups per particle, with an average particle size from about 40 to about 50 nm. These particles can withstand harsh treatment, such as incubation at 120° C. for 30 minutes, without a change in size or loss of their dextran coat. Amino groups in amino-CLIO can react by N-hydroxysuccinimide (NHS) based bifunctional cross-linking, allowing attachment of a range of sulfhydryl-bearing biomolecules. This gives rise to biomolecule-nanoparticle conjugates with unique biological properties. In addition to their use as sensors, the resultant superparamagnetic nanoparticles are valuable for imaging specific molecular targets, and as reagents for cell labeling and tracking.

Current diagnostic systems involve, for example, microarray technology, polymerase chain reaction (PCR), in situ hybridization, antibody-based immunoassays (e.g. enzyme-linked immunosorbant assays), chemiluminescence, nephelometry, and/or photometry. These systems cannot perform the diversity of assays at high sensitivity that is possible with an NMR-based nanosensor system.

Various non-NMR-based point of care bio-assays have been developed, such as portable blood glucose meters that operate using test strips impregnated with glucose oxidase. However, these systems are generally not as reliable as central hospital assays because they lack the sensitivity, calibration, and maintenance that a laboratory setting provides. These portable systems also lack the sensitivity that is possible with NMR-based nanosensor systems, and they cannot be easily adapted for multiple analyte detection.

The above-cited Josephson et al. and Perez et al. documents describe application of classical NMR relaxation methods with nanosensors using off-the-shelf relaxometers and MRI units. However, these units require large NMR RF coils and large magnets and are bulky, expensive, and are not tailored for use with magnetic nanosensors.

There is a need for a less expensive, commercially-realizable NMR-based analyte detection device suitable for use with magnetic nanosensors.

SUMMARY OF THE INVENTION

The invention provides a small, integrated NMR-based analyte detection device with superparamagnetic nanosensors which can be customized for detection of any of a wide variety of analytes. The device may be used, for example, as a portable unit for point of care diagnosis and/or field use, or the device may be implanted for continuous or intermittent monitoring of one or more biological species of interest in a patient.

In one configuration, the device contains an array of many small wells (e.g. 100, 1000, 10,000, or more "micro wells") for containing a liquid sample, each well surrounded by a tiny radio frequency (RF) coil that detects an echo response produced by exposing the liquid sample in the well to a bias magnetic field and RF excitation. The magnetic field is created using one or more magnets which may be part of the device itself, or may be external to the device. As used herein, "well" means any localizer of a liquid sample, for example, an indentation, a container, a support, a channel, a reservoir, a sunken volume, a compartment, a recessed area, an enclosure with or without an opening, a tube, a trough, a semipermeable membrane, an interface between two phases (e.g. an organic-inorganic interface, a hydrophilic-hydrophobic interface, an oligophilic-oligophobic interface, and the like), and/or an interface between two fluids (gases and/or liquids).

Superparamagnetic nanoparticles are pre-deposited onto/into the micro wells before introduction of the liquid sample, or, alternatively, the nanoparticles may be introduced into the wells along with the liquid sample. The nanoparticles have binding moieties on their surfaces, which are operative to bind to (i) an analyte, (ii) another of the binding moieties, and/or (iii) an aggregation-inducing molecule in the liquid sample. These binding moieties may be customized such that aggregation or disaggregation of the nanoparticles occurs in the presence of one or more analyte(s) to be detected.

The superparamagnetic character of the nanoparticles enhances water (or other solvent with free hydrogens) relaxation rates, an enhancement that is altered by the aggregation or disaggregation of the particles. The presence and/or concentration(s) of the analyte(s) of interest can be detected via NMR relaxation methods, even at extremely low concentrations, for example, 100 femto-molar and below. This increased sensitivity can be achieved because of the effect of the analyte on aggregation, coupled with the effect of the state of aggregation on T2 relaxation times.

In preferred embodiments, the devices offer a number of technological advancements geared toward increasing sensitivity of analyte detection. These include, for example: (i) the use of a plurality of micro wells; (ii) the use of a well whose cross section varies spatially; (iii) the design of well/coil pairs with high filling factor; (iv) the positioning of an electrical element for echo signal conditioning in close proximity to the RF sensing coil; (v) the use of RF sensing coils with high Q factor; (vi) the use of one or more rare earth magnets for producing the bias magnetic field; (vii) the positioning of the magnet(s) in close proximity to the liquid sample; and (viii) the reduction in bandwidth made possible by customization of the coated nanoparticles and well/coil geometry for detection of a specific analyte. Embodiments of the invention may make use of one or more of these technological advancements in any combination.

The use of a plurality of micro wells further enhances detection sensitivity, repeatability, and precision. Duplicate sampling wells allow multiple, substantially simultaneous measurements of analyte(s). Furthermore, the binding moieties on the surfaces of the nanoparticles used in the wells can be customized to provide greater sensitivity and precision. For example, the concentration of nanoparticles and/or binding moieties, and/or the types of binding moieties used in the different wells can be varied, allowing for more sensitive detection and/or more precise concentration measurement of the target analyte(s). Also, built-in self-calibration is enabled by the presence of one or more wells reserved for calibration. For example, one or more wells having a known NMR relaxation characteristic that is substantially unaffected by the analyte can be dedicated for calibration.

In addition to the use of an array of well/coil pairs, another technological feature improving analyte detection sensitivity of the devices is the use of a well whose cross section varies spatially to concentrate the analyte in the magnetic field. For example, each well may have a portion of larger cross-sectional area and a portion of smaller cross-sectional area. Superparamagnetic nanoparticles coated with binding moieties differentially move analyte-containing aggregations in the intense magnetic field. A bias magnetic field moves target analyte trapped in the aggregation of the magnetic nanoparticles in the direction of the field from the large cross-section area of the well into the small cross-section area of the well. In this way, the analyte is concentrated in the small cross-sectional area of the well. The small cross-sectional area of the well is surrounded by an RF coil for sensing the echo response of the solution. In this way, the analyte may be concentrated, for example, by a factor of about 1000, thereby increasing sensitivity of the device about 1000 fold. The magnet(s) and/or magnetic field used to evoke an NMR relaxation response is synergistically used to concentrate the target analyte for improved detection sensitivity. The device may include an array of many micro wells and tiny RF coils surrounding the narrow portions of these wells.

Yet another technological feature improving analyte detection sensitivity of the devices is the use of a well and RF coil configured to provide a high filling factor. Filling factor, as used herein, is the volume of liquid sample in a well divided by the volume circumscribed by the RF coil. Improved analyte detection sensitivity can be achieved by using a well and RF coil with a filling factor of at least about 0.1, preferably at least about 0.7, and more preferably about 1. For example, in one embodiment, the device contains an array of micro wells surrounded by tiny RF coils, where each well/coil combination has a filling factor of about 1.

Still another technological feature improving analyte detection sensitivity is the positioning of an electrical element for echo signal conditioning in close proximity to the RF coil. The small size of the wells facilitates placement of signal conditioning electronics within 1 millimeter, for example, of the corresponding RF coil. The echo signal conditioning performed by the electrical element may include, for example, amplification, rectification, and/or digitization of the echo signal. The electrical element (as the term is used herein in the singular) may include one or more discrete electrical components.

A further technological feature improving analyte detection sensitivity is the use of RF sensing coils with high Q factor. Quality factor, or Q factor, of an RF coil is a measure of its efficiency as an inductor, and is defined herein as the ratio of the inductive reactance of the RF coil to its resistance at a given frequency, for example, the Larmor frequency. Using coils having high Q factor improves the sensitivity of the device.

Another technological feature enhancing analyte detection sensitivity is the use of rare earth magnets to create the bias magnetic field. Examples of rare earth magnets include, for example, neodymium magnets such as $Nd_2Fe_{14}B$ (neodymium-iron-boron), and samarium cobalt magnets such as $SmCo_5$. This helps to maximize the strength of the magnetic field and improves sensitivity.

Another technological feature of the device is the positioning of the magnet(s), for example, rare earth magnet(s), used to produce the bias magnetic field in close proximity to the liquid sample, for example, within 1 millimeter. This allows the generation of a bias magnetic field with strength, for example, from about 1 to about 2 Tesla, as compared with commercial units that operate at 0.5 Tesla. The close proximity of the magnet to the liquid sample is facilitated by the micro design of the system and the integrated nature of the device.

Sensitivity of the device is also improved by the ability to use narrow bandwidth. Bandwidth in this sense is the amplitude roll off of the signal processing chain. The wider the bandwidth, the flatter the roll off with frequency. A wider bandwidth must be used when it is not clear what frequency is to be detected; however increased bandwidth results in increased noise. Use of a narrower bandwidth results in less noise (and increased signal-to-noise ratio, S/N), but may not be possible unless the frequency to be detected is precisely known. The device makes possible the use of a reduced bandwidth, because the analyte to be detected in each well is known and typically pre-determined, and the coated nanoparticles and/or the well/coil geometry can be specifically customized for detection of the specific analyte. Multiple analytes may still be detected, since different wells can be customized for detection of different analytes, for example, by use of different binding moieties on the nanoparticles in the different wells.

Further customization of the electronics is possible. For example, the electronics for a given well may be tuned to a specific, determinable frequency characteristic based at least in part on the type of analyte/nanoparticle combination in the well and/or the concentration of the analyte and/or nanoparticle in the well. Furthermore, the use of one or more pulse sequences may be developed for optimum detection sensitivity/accuracy for a given analyte of interest, and/or for a given nanosensor.

In preferred embodiments, the device uses low power and is able to operate in magnetic fields of less strength than current NMR systems, for example, less than about 7 T, less than about 5 T, less than about 4 T, less than about 3 T, less than about 2 T, at about 1 T, or less than about 1 T. In general, higher magnetic field strength could be used for assays requiring greater sensitivity, while lower magnetic field strength (for example, below 1 T) could be used for assays requiring less sensitivity. The power source may be any power source, for example, a battery or any electrical power source. An example power source would be a lithium ion battery, such as (or similar to) a lithium ion battery used in cellular telephones.

Aggregation of the nanoparticles is an equilibrium process. Nanoparticles may aggregate for a specific period of time (e.g. sufficient time for measurement to take place), then return to a nonaggregated condition. Thus, the nanoparticles, localized in the wells, may be reused and would not need to be replaced following each test. This enhances the convenience and low cost of the unit.

Because of the adaptability of the nanoparticles (and binding moieties linked thereto), the device may perform numerous bio-diagnostic functions. The device may be customized to perform a specific function, or adapted to perform more than one function, e.g. via changeable cartridges containing arrays of micro wells with customized, lyophilized nanoparticles deposited thereon.

The device may be used to perform bio-diagnostics rapidly, with high sensitivity, and at low cost. The device can be made portable and may include a chip, module, or cartridge containing the sample wells, as well as a handheld reader (remote or attached), making the unit useful in the field by paramedics, emergency room personnel, or other medical personnel for emergency medical care. Applications of the device include use by paramedics (e.g. in an ambulance or in the field), emergency room personnel, or other military or civilian medical personnel. The device may also be suitable for pediatric or adult home health care, for example, for the monitoring of glucose levels in the treatment of diabetes. Home diagnostics may reduce the need for doctor and hospital visits. Implantable versions of the device may provide continuous monitoring of species of interest, for example, glucose, coumadin, bacteria (e.g., post surgery), and/or drugs (e.g. for controlled dosing), to name a few.

The device may be used to detect a very wide range of biologically active substances, as well as other analytes. Of current methods (e.g. chemiluminescence, nephelometry, photometry, and/or other optical/spectroscopic methods), no single approach can achieve the diversity of analysis that is possible with NMR, even without the sensitivity improvements made possible by embodiments described herein. The sensitivity improvements provided by embodiments of the invention described herein allow further breadth and adaptability of analysis over current NMR techniques. For example, embodiments of the invention may be used or adapted for detection, for example, of any protein (e.g., biomarkers for cancer, serum proteins, cell surface proteins, protein fragments, modified proteins), any infectious disease (e.g., bacterial based on surface or secreted molecules, virus based on core nucleic acids, cell surface modifications, and the like), as well as a wide range of gases and/or small molecules.

A wider range of drugs may be developed, due to the improved ability to detect and maintain appropriate dosages using the NMR device described herein. Drugs may be administered either manually or automatically (e.g. via automatic drug metering equipment), and may be monitored intermittently or continuously using the device. Dosage may therefore be more accurately controlled, and drugs may be more accurately maintained within therapeutic ranges, avoiding toxic concentrations in the body. Thus, drugs whose toxicity currently prevents their use may become approved for therapeutic use when monitored with the device described herein.

Medical conditions that may be rapidly diagnosed by the device for proper triaging and/or treatment include, for example, pain, fever, infection, cardiac conditions (e.g. stroke, thrombosis, and/or heart attack), gastrointestinal disorders, renal and urinary tract disorders, skin disorders, blood disorders, and/or cancers. Tests for infectious disease and cancer biomarkers for diseases not yet diagnosable by current tests may be developed and performed using the NMR device described herein.

The device may be used for detection of chemical and/or biological weapons in the field, for example, nerve agents, blood agents, blister agents, pulmonary agents, incapacitating agents (e.g. lachrymatory agents), anthrax, ebola, bubonic plague, cholera, tularemia, brucellosis, Q fever, typhus, encephalitis, smallpox, ricin, SEB, botulism toxin, saxitoxin, mycotoxin, and/or other toxins.

Because the devices are adaptable for detection of multiple analytes, a unit may be used to perform many ICU tests (including, e.g., PICU, SICU, NICU, CCU, and PACU) quickly and with a single blood draw. The tests may also be performed in the emergency room, in the physician's office, in field medicine (e.g. ambulances, military medical units, and the like), in the home, on the hospital floor, and/or in clinical labs. The multiplexing capability of the devices also makes them a valuable tool in the drug discovery process, for example, by performing target validation diagnostics.

Measurements for one or more analytes may be made, for example, based on a single draw, temporary draws, an intermittent feed, a semi-continuous feed, a continuous feed, serial exposures, and/or continuous exposures. Measurements may include a detection of the presence of the one or more analytes and/or a measurement of the concentration of one or more analytes present in the sample.

Where the device is used as an implantable unit, one embodiment includes a semi-permeable pouch containing the nanoparticles and a set of bias field permanent magnets. The implantable unit may be small, for example, about 2 mm diameter and about 5 mm long, and may be implanted in the arm. A reading may be made using a band, similar to a heart rate monitor band, that is placed around the arm such that the reader, outside the body, is in proximity to the implant and measurements are performed non-invasively. The band may contain the RF coil and associated electronics.

In another embodiment of an implantable device, the unit may be a deep implantable with RF excitation and/or sense coil(s), bias magnet(s), nanoparticle pouch, and power source all implanted. In another embodiment of an implantable device, the bias magnet(s), RF excitation and/or sense coil(s), and electronics are all external. The nanoparticle pouch is implanted, for example, in the arm, and a reader on a band contains the signal side bias magnet, RF coil(s), and electronics. The band may be worn as would be a watch band, providing continuous or intermittent monitoring of an analyte of interest without wires penetrating the body. The implant would not require a power source, the power being provided by the reader worn externally by the patient.

In one aspect, the invention relates to a device for the detection of an analyte, the device including: a support defining a well for holding a liquid sample including magnetic particles and the analyte, the magnetic particles having binding moieties linked thereto; and an RF coil disposed about the liquid sample, the RF coil being configured to detect an echo response produced by exposing the liquid sample to a bias magnetic field created using one or more magnets and an RF excitation, wherein the RF coil has a characteristic dimension from about 10 μm to about 1000 μm.

The characteristic dimension may be, for example, the diameter of the coil (e.g. an inner diameter, an outer diameter, or an average diameter), the length of the coil, or the depth of the coil. In certain embodiments, the RF coil has a diameter no greater than about 900 μm, no greater than about 800 μm, no greater than about 700 μm, no greater than about 600 μm, no greater than about 500 μm, no greater than about 400 μm, or no greater than about 300 μm. In certain embodiments, the RF coil has a length or depth no greater than about 900 μm, no greater than about 800 μm, no greater than about 700 μm, no greater than about 600 μm, no greater than about 500 μm, no greater than about 400 μm, or no greater than about 300 μm.

In certain embodiments, the well and the RF coil are configured to provide a filling factor of at least about 0.1, where the filling factor is the volume of the liquid sample in the well divided by the volume circumscribed by the RF coil. In other embodiments, the filling factor is at least about 0.2, at least about 0.3, at least about 0.4, at least about 0.5, at least about 0.6, at least about 0.7, at least about 0.8, at least about 0.9, at least about 0.95, or about 1.

The well is preferably a micro well, meaning that the volume of the liquid sample in the well is less than about 1 mL. In certain embodiments, the volume of the liquid sample in the well is less than about 800 μL, less than about 700 μL, less than about 600 μL, less than about 500 μL, less than about 400 μL, less than about 300 μL, less than about 200 μL, less than about 100 μL, less than about 10 μL, less than about 1 μL, less than about 500 nL, less than about 300 nL, less than about 100 nL, less than about 50 nL, less than about 20 nL, less than about 5 nL, less than about 2 nL, or about 1 nL.

The RF coil is preferably a micro coil, meaning that the volume circumscribed by the RF coil is less than about 1 mL. In certain embodiments, the volume circumscribed by the RF coil is less than about 800 μL, less than about 700 μL, less than about 600 μL, less than about 500 μL, less than about 400 μL, less than about 300 μL, less than about 200 μL, less than about 100 μL, less than about 10 μL, less than about 1 μL, less than about 500 nL, less than about 300 nL, less than about 100 nL, less than about 50 nL, less than about 20 nL, less than about 5 nL, less than about 2 nL, or about 1 nL.

In certain embodiments either or both of (i) the volume of the liquid sample in the well and (ii) the volume circumscribed by the RF coil is/are less than about 1 mL. In certain embodiments, either or both of (i) the volume of the liquid sample in the well and (ii) the volume circumscribed by the RF coil is/are less than about 800 μL, less than about 700 μL, less than about 600 μL, less than about 500 μL, less than about 400 μL, less than about 300 μL, less than about 200 μL, less than about 100 μL, less than about 10 μL, less than about 1 μL, less than about 500 nL, less than about 300 nL, less than about 100 nL, less than about 50 nL, less than about 20 nL, less than about 5 nL, less than about 2 nL, or about 1 nL.

The device may further include an electrical element in communication with the RF coil, the electrical element configured to at least partially condition a signal corresponding to the echo response. For example, the electrical element may include a pre-amplifier, an amplifier, a rectifier, a transmitter, and/or a digitizer for amplifying, rectifying, transmitting, and/or digitizing the signal corresponding to the echo response. In certain embodiments, the electrical element is configured to do at least one of the following: (i) amplify the signal, (ii) rectify the signal, (iii) digitize the signal. The electrical element (as the term is used herein in the singular) may include one or more discrete electrical components. For example, the electrical element may include any combination of the components shown in FIG. 14 such as the power splitter, power combiner, pre-amplifier, mixer, low-pass filter, and/or low noise amplifier.

The RF coil is preferably disposed sufficiently close to the electrical element to provide a Q factor of at least 1, where the Q factor (quality factor) is the ratio of the inductive reactance of the RF coil to its resistance at a given frequency, for example, the Larmor frequency. In certain embodiments, the Q factor is at least about 5, at least about 10, at least about 20, at least about 30, at least about 40, at least about 50, at least about 60, at least about 70, at least about 80, at least about 90, at least about 100, or at least about 125. The proximity of the RF coil to the electrical element is important in the preservation of the signal, allowing increased sensitivity.

The RF coil may be integrated with the support that defines the well, where the RF coil is disposed about the well. The support may be a substrate, with the well etched from the substrate material. Alternatively, the support may form the base of the well, with the RF coil itself serving as part or all of one or more sides of the well.

Preferably, the RF coil is disposed within one centimeter of the electrical element. In certain embodiments, the RF coil is disposed within 5 millimeters of the electrical element, within 3 millimeters of the electrical element, within 2 millimeters of the electrical element, within 1 millimeter of the electrical element, within 500 micrometers of the electrical element, within 100 micrometers of the electrical element, within 50 micrometers of the electrical element, or within 5 micrometers of the electrical element.

The magnetic particles may include superparamagnetic nanoparticles with binding moieties on their surfaces. The binding moieties are preferably operative to alter an aggregation of the magnetic particles as a function of the presence or concentration of the analyte. The magnetic particles may include an oxide and/or a hydroxide of Fe, Si, Sn, An, Ti, Bi, Zr, and/or Zn. The magnetic particles are preferably superparamagnetic and have crystallite size from about 1 nm to about 100 nm. The magnetic nanoparticles preferably have a metal oxide core of about 1 to about 25 nm, from about 3 to about 10 nm, or about 5 nm in diameter. The binding moieties may include one or more species of one or more of the following: an amino acid, a nucleic acid, an oligonucleotide, a therapeutic agent, a metabolite of a therapeutic agent, a peptide, a polypeptide, a protein, a carbohydrate, a polysaccharide, a virus, and/or bacteria. For example, in one embodiment, the binding moieties may include one, two, or more types of oligonucleotides and/or one, two, or more types of proteins. The binding moieties may be a polymer, or may be part of a polymer that is linked to, or otherwise associated with one or more of the magnetic particles. The binding moieties preferably include functional groups, for example, the binding moieties may include one or more species of one or more of the following: an amino group, a carboxyl group, a sulfhydryl group, an amine group, an imine group, an epoxy group, a hydroxyl group, a thiol group, an acrylate group, and/or an isocyano group.

The analyte may include one or more species of one or more of the following: a protein, a peptide, a polypeptide, an amino acid, a nucleic acid, an oligonucleotide, a therapeutic agent, a metabolite of a therapeutic agent, RNA, DNA, an antibody, an organism, a virus, bacteria, a carbohydrate, a polysaccharide, and glucose. The analyte may also include, for example, a lipid, a gas (e.g., oxygen, carbon dioxide), an electrolyte (e.g., sodium, potassium, chloride, bicarbonate, BUN, creatinine, glucose, magnesium, phosphate, calcium, ammonia, lactate), a lipoprotein, cholesterol, a fatty acid, a glycoprotein, a proteoglycan, and/or a lipopolysaccharide. Furthermore, as used herein, "detection of an analyte" may also mean measurement of physical properties of a solution containing one or more analytes, for example, measurement of dipole moment, ionization, solubility/saturation, viscosity, gellation, crystallization, and/or phase changes of the solution.

The bias magnetic field may be substantially uniform, or it may have a spatial gradient. The device itself may include at least one of the one or more magnets. At least one of the one or more magnets may be external to the device. The RF excitation may be transmitted via an RF excitation coil, separate from the RF coil disposed about the well (where the coil disposed about the well may be termed the "sensing" coil). In one embodiment, the RF excitation may be transmitted via the RF coil disposed about the well. For example, the RF coil may both transmit the RF excitation and detect the echo response (the RF coil is both an excitation coil and a sensing coil).

The device (or an element thereof) may be fabricated on a chip. For example, the device (or an element thereof) may be fabricated in a MEMS (micro electromechanical systems) process. The support (e.g., defining the well) may include a plastic, polymer, film, fluid, fluid interface, liquid-liquid interface, organic (fluid)-inorganic (fluid) interface, and/or metals, for example. The support may include glass, Si, and/or SiGe. In certain embodiments, the liquid sample runs over the support for a continuous read (the liquid is not necessarily stationary on the support).

The RF coil may be deposited on a surface of the chip. The RF coil may be a wound solenoid coil, a planar coil, a saddle coil, a Helmholtz coil, or a MEMS solenoid coil.

In certain embodiments, the magnetic particles are deposited onto the surface of the support defining the wells, for example, prior to introduction of the liquid sample into the wells. The particles may be deposited onto the support (e.g. a substrate) with a printer (e.g. a matrix dot printer or a laser printer), and/or the particles may be reconstitutable upon introduction of liquid. In certain embodiments, the magnetic particles are lyophilized.

The binding moieties are preferably operative to bind to at least one of the following (i, ii, and/or iii): (i) the analyte; (ii) another of the binding moieties; and (iii) an aggregation-inducing molecule in the liquid sample. In this way, the binding moieties are operative to produce an aggregate of multiply-linked magnetic particles as a function of the presence or concentration of the analyte in the liquid sample. An example of an aggregation-inducing molecule is avidin and may be used, for example, where the binding moieties include biotin. In another embodiment, the aggregation-inducing molecule is biotin and the binding moieties include avidin. Alternatively, the aggregate of multiply-linked magnetic particles may be disaggregated as a function of the presence or concentration of the analyte in the liquid sample. The bonds and/or links are preferably reversible, such that aggregation and/or disaggregation is/are reversible, equilibrium-driven processes.

The aggregate may have an approximate size from about 100 nm to about 500 nm in its largest dimension, for example. In certain embodiments, the aggregate has an approximate size greater than about 50 nm, greater than about 100 nm, greater than about 200 nm, or greater than about 300 nm. The aggregate may contain, for example, from about 2 to about 20 magnetic particles linked via the binding moieties. The magnetic particles may have an average size from about 5 nm to about 500 nm in their largest dimension. In certain embodiments, the magnetic particles have an average size less than about 500 nm in their largest dimension, less than about 200 nm in their largest dimension, less than about 100 nm in their largest dimension, less than about 50 nm in their largest dimension, less than about 40 nm in their largest dimension, less than about 30 nm in their largest dimension, or less than about 20 nm in their largest dimension. The largest dimension may be diameter, for example.

The device may further include a reader configured to receive the signal corresponding to the echo response. The reader may include an electrical element for processing the signal and a display for indicating analyte presence or concentration. For example, the reader may determine a change in T2 relaxation time according to the signal corresponding to the echo response, thereby indicating analyte presence or concentration. The reader may include a magnet for creation of the bias magnetic field and/or an RF excitation coil for providing the RF excitation. The reader may be spatially separated from the well and/or the sensing RF coil. For example, in the case where the device includes an implantable, the reader may be held outside the body. The device may be implantable and operable without skin-penetrating wires. Other embodiments may include one or more elements that penetrate the skin.

The device may be portable. For example, the device may weigh less than about 1 kilogram, less than about 500 grams, less than about 400 grams, or less than about 300 grams.

In another aspect, the invention relates to a device for the detection of an analyte, the device including a plurality of wells for holding a liquid sample including magnetic particles and the analyte, the magnetic particles having binding moieties linked thereto, and, for each of the wells: an RF coil disposed about the well, the RF coil configured to detect an echo response produced by exposing the liquid sample in the well to a bias magnetic field created using one or more magnets and an RF excitation. The description of elements of the embodiments above can be applied to this aspect of the invention as well.

The wells and the RF coils are preferably small. For example, in certain embodiments either or both of (i) the volume of the liquid sample in each well and (ii) the volume circumscribed by each RF coil is/are less than about 1 mL. In certain embodiments, either or both of (i) the volume of the liquid sample in each well and (ii) the volume circumscribed by each RF coil is/are less than about 800 μL, less than about 700 μL, less than about 600 μL, less than about 500 μL, less than about 400 μL, less than about 300 μL, less than about 200 μL, less than about 100 μL, less than about 10 μL, less than about 1 μL, less than about 500 nL, less than about 300 nL, less than about 100 nL, less than about 50 nL, less than about 20 nL, less than about 5 nL, less than about 2 nL, or about 1 nL.

The wells are preferably arranged in an array, which may be, for example, a 2-D or a 3-D array. The device may be configured to allow distribution of liquid into the plurality of wells. For example, channels may be designed according to methods known in the art of microfluidics to allow distribution of liquid into the plurality of wells. For example, the design may enable pressure driven flow using one or more positive displacements pumps or micropumps, such as syringe pumps. The design may also or alternatively enable electrokinetic flow via electroosmotic pumping.

The wells may include one or more wells dedicated for calibration. For example, one or more wells may have a known measurable characteristic that is substantially unaffected by the analyte.

The plurality of wells may allow detection or concentration measurement of one or more analytes. For example, the magnetic particles having different binding moieties are disposed in different wells for detection of multiple analytes. In certain embodiments, magnetic particles having the same binding moieties are disposed in different wells for replicate measurements, thereby improving accuracy (where improved accuracy may mean improved detection sensitivity). In certain embodiments, the magnetic particles having the same binding moieties (same species of binding moiety) are disposed in different wells for detection of varying analyte concentrations in the liquid sample. In certain embodiments, the different wells have different concentrations of binding moieties disposed therein. In certain embodiments, the magnetic particles having different binding moieties are disposed in different wells for detection of the analyte, where the different binding moieties promote aggregation or disaggregation of the magnetic particles in proportion to concentration of the analyte.

The device may further include, for each of the wells, an electrical element in communication with the RF coil corresponding to the well, the electrical element configured to at least partially condition a signal corresponding to the echo response. For example, each electrical element may include an amplifier, a rectifier, a transmitter, and/or a digitizer for amplifying, rectifying, transmitting, and/or digitizing the signal corresponding to the echo response. In certain embodiments, each electrical element is configured to do at least one of the following: (i) amplify the signal from the corresponding well, (ii) rectify the signal, (iii) digitize the signal. The electrical element (as the term is used herein in the singular) may include one or more discrete electrical components.

Each RF coil is preferably disposed sufficiently close to the corresponding electrical element to provide a Q factor of at least 1, where the Q factor (quality factor) is the ratio of the inductive reactance of the RF coil to its resistance at a given frequency, for example, the Larmor frequency. In certain embodiments, the Q factor is at least about 5, at least about 10, at least about 20, at least about 30, at least about 40, at least about 50, at least about 60, at least about 70, at least about 80, at least about 90, at least about 100, or at least about 125.

The RF coils may be integrated with (e.g. embedded in) a substrate that defines the wells, where each RF coil is disposed about its respective well. Alternatively, a substrate may serve as the base of each of the wells, with each RF coil itself serving as part or all of one or more sides of the well. Preferably, each RF coil is disposed within one centimeter of the corresponding electrical element. In certain embodiments, the RF coil is disposed within 5 millimeters of the electrical element, within 3 millimeters of the electrical element, within 2 millimeters of the electrical element, within 1 millimeter of the electrical element, within 500 micrometers of the electrical element, within 100 micrometers of the electrical element, within 50 micrometers of the electrical element, or within 5 micrometers of the electrical element.

The binding moieties are preferably operative to alter an aggregation of the magnetic particles as a function of the presence or concentration of the analyte. The magnetic particles may include superparamagnetic nanoparticles with binding moieties on their surfaces. The magnetic particles may include an oxide and/or a hydroxide of Fe, Si, Sn, An, Ti, Bi, Zr, and/or Zn. The magnetic particles are preferably superparamagnetic and have crystallite size from about 1 nm to about 100 nm. The magnetic nanoparticles preferably have a metal oxide core of about 1 to about 25 nm, from about 3 to about 10 nm, or about 5 nm in diameter. The binding moieties may include one or more species of one or more of the following: an amino acid, a nucleic acid, an oligonucleotide, a therapeutic agent, a metabolite of a therapeutic agent, a peptide, a polypeptide, a protein, a carbohydrate, a polysaccharide, a virus, and/or bacteria. For example, in one embodiment, the binding moieties may include one, two, or more types of oligonucleotides and/or one, two, or more types of proteins. The binding moieties may be a polymer, or may be part of a polymer that is linked to, or otherwise associated with one or more of the magnetic particles. The binding moieties preferably include functional groups, for example, the binding moieties may include one or more species of one or more of the following: an amino group, a carboxyl group, a sulfhydryl group, an amine group, an imine group, an epoxy group, a hydroxyl group, a thiol group, an acrylate group, and/or an isocyano group.

The analyte may include one or more species of one or more of the following: a small organic molecule, a protein, a peptide, a polypeptide, an amino acid, a nucleic acid, an oligonucleotide, a therapeutic agent, a metabolite of a therapeutic agent, RNA, DNA, an antibody, an organism, a virus, bacteria, a carbohydrate, a polysaccharide, and glucose. The analyte may also include, for example, a lipid, a gas (e.g., oxygen, carbon dioxide), an electrolyte (e.g., sodium, potassium, calcium, ammonia, lactate, lactic acid), a lipoprotein, cholesterol, a fatty acid, a glycoprotein, a proteoglycan, and/or a lipopolysaccharide. Furthermore, "detection of an analyte" may also mean measurement of physical properties of a solution containing one or more analytes, for example, measurement of dipole moment, ionization, solubility/saturation, viscosity, gellation, crystallization, and/or phase changes of the solution.

The bias magnetic field may be substantially uniform, or it may have a spatial gradient. The device itself may include at least one of the one or more magnets. At least one of the one or more magnets may be external to the device. The RF excitation may be transmitted via an RF excitation coil, separate from the RF coils disposed about the wells (where the coils disposed about the wells may be termed the "sensing" coils). In one embodiment, the RF excitation may be transmitted via the RF coils disposed about the wells. For example, the RF coils may both transmit the RF excitation and detect the echo responses from the liquid samples in their respective wells (where each of the RF coils acts as both an excitation coil and a sensing coil).

The device (or an element thereof) may be fabricated on a chip. For example, the device (or an element thereof) may be fabricated in a MEMS (micro electromechanical systems) process.

The RF coils may be deposited on a surface of the chip. The RF coils may include wound solenoid coils, planar coils, saddle coils, Helmholtz coils, and/or MEMS solenoid coils.

In certain embodiments, the magnetic particles are deposited onto surfaces of the wells (e.g. a substrate from which the wells are etched or built up), for example, prior to introduction of the liquid sample into the wells. The particles may be deposited onto the surfaces with a printer, and/or the particles may be reconstitutable upon introduction of liquid. In certain embodiments, the magnetic particles are lyophilized.

The binding moieties are preferably operative to bind to at least one of the following (i, ii, and/or iii): (i) the analyte; (ii) another of the binding moieties; and (iii) an aggregation-inducing molecule in the liquid sample. In this way, the binding moieties are operative to produce an aggregate of multiply-linked magnetic particles as a function of the presence or concentration of the analyte in the liquid sample. An example of an aggregation-inducing molecule is avidin and may be used, for example, where the binding moieties include biotin. In another embodiment, the aggregation-inducing molecule is biotin and the binding moieties include avidin. Alternatively, the aggregate of multiply-linked magnetic particles may be disaggregated as a function of the presence or concentration of the analyte in the liquid sample.

The device may include a replaceable and/or interchangeable cartridge containing the array of wells pre-loaded with dried (e.g. lyophilized) magnetic particles. The cartridge may be designed for detection and/or concentration measurement of a particular analyte. The device may be usable with different cartridges, each designed for detection and/or concentration measurements of different analytes. The cartridge may be sized for convenient insertion into and ejection from a housing containing one or more of the magnets and/or an RF excitation coil.

The device may further include a reader configured to receive the signals corresponding to the echo responses from the wells. The reader may include an electrical element for processing the signals and a display for indicating analyte presence or concentration. For example, the reader may determine a change in T2 relaxation time according to the signals corresponding to the echo responses, thereby indicating analyte presence or concentration. The reader may include a magnet for creation of the bias magnetic field and/or an RF excitation coil for providing the RF excitation. The reader may be spatially separated from the wells and/or the sensing RF coil. For example, in the case where the device is adapted for implementation into a mammal, the reader may be held outside the body. The device may be implantable and operable without skin-penetrating wires. Other embodiments may include one or more elements that penetrate the skin.

The device may be portable. For example, the device may weigh less than about 1 kilogram, less than about 500 grams, less than about 400 grams, or less than about 300 grams.

In yet another aspect, the invention relates to a device including a support defining one or more wells for holding a liquid sample; and disposed on the support, for reconstitution within the one or more wells, dried superparamagnetic particles having binding moieties linked thereto, where the binding moieties are operative to alter an aggregation of the magnetic particles in the liquid sample as a function of the presence or concentration of an analyte in the liquid sample. The description of elements of the embodiments above can be applied to this aspect of the invention as well.

In one embodiment, the device further includes, for each of the one or more wells, an RF coil disposed about the well and an electrical element in communication with the RF coil, wherein the RF coil is configured to detect an echo response produced by exposing the liquid sample in the well to a bias magnetic field created using one or more magnets and an RF excitation, wherein the electrical element is configured to at least partially condition a signal corresponding to the echo response.

In certain embodiments, the device is a component of an analyte detection system. For example, in certain embodiments, the device is a replaceable and/or interchangeable cartridge containing the array of wells pre-loaded with dried (e.g. lyophilized) magnetic particles. The cartridge may be designed for detection and/or concentration measurement of a particular analyte. Different cartridges may be designed for detection and/or concentration measurements of different analytes. The cartridges may themselves include the RF coils configured to detect echo responses from the liquid samples in corresponding wells, or the RF coils may be separate from the cartridges. The cartridges may be designed for operation with a console, for example, where the console includes one or more magnets for producing the bias magnetic field and/or an RF excitation coil for transmitting the RF excitation.

In certain embodiments, the device further includes an RF excitation coil for transmitting the RF excitation, where the RF excitation coil is separate from the one or more RF coils disposed about the one or more wells (e.g. the RF coils for sensing echo response). For each of the one or more wells, the respective RF coil is disposed within one centimeter, within one millimeter, or within 100 μm of the electrical element in communication with the RF coil. The electrical element may be configured to do at least one of the following: (i) amplify the signal corresponding to the echo response; (ii) rectify the signal; (iii) digitize the signal.

The binding moieties are preferably operative to alter an aggregation of the superparamagnetic particles as a function of the presence or concentration of the analyte. The superparamagnetic particles may include superparamagnetic nanoparticles with binding moieties on their surfaces. The superparamagnetic particles may include an oxide and/or a hydroxide of Fe, Si, Sn, An, Ti, Bi, Zr, and/or Zn. The superparamagnetic particles preferably have crystallite size from about 1 nm to about 100 nm. The superparamagnetic particles preferably have a metal oxide core of about 1 to about 25 nm, from about 3 to about 10 nm, or about 5 nm in diameter. The binding moieties may include one or more species of one or more of the following: an amino acid, a nucleic acid, an oligonucleotide, a therapeutic agent, a metabolite of a therapeutic agent, a peptide, a polypeptide, a protein, a carbohydrate, a polysaccharide, a virus, and/or bacteria. For example, in one embodiment, the binding moieties may include one, two, or more types of oligonucleotides and/or one, two, or more types of proteins. The binding moieties may be a polymer, or may be part of a polymer that is linked to, or otherwise associated with one or more of the superparamagnetic particles. The binding moieties preferably include functional groups, for example, the binding moieties may include one or more species of one or more of the following: an amino group, a carboxyl group, a sulfhydryl group, an amine group, an imine group, an epoxy group, a hydroxyl group, a thiol group, an acrylate group, and/or an isocyano group.

The analyte may include one or more species of one or more of the following: a protein, a peptide, a polypeptide, an amino acid, a nucleic acid, an oligonucleotide, a therapeutic agent, a metabolite of a therapeutic agent, RNA, DNA, an antibody, an organism, a virus, bacteria, a carbohydrate, a polysaccharide, and glucose. The analyte may also include, for example, a lipid, a gas (e.g., oxygen, carbon dioxide), an electrolyte (e.g., sodium, potassium, calcium, ammonia, lactate, lactic acid), a lipoprotein, cholesterol, a fatty acid, a glycoprotein, a proteoglycan, and/or a lipopolysaccharide. Furthermore, "detection of an analyte" may also mean measurement of physical properties of a solution containing one or more analytes, for example, measurement of dipole moment, ionization, solubility/saturation, viscosity, gellation, crystallization, and/or phase changes of the solution.

For each of the one or more wells, the well and the RF coil disposed about the well are preferably configured to provide a filling factor of at least about 0.7, at least about 0.9, or about 1.

The device may further include a reader configured to receive, for each of the wells, the signal corresponding to the echo response from the respective well.

In another aspect of the invention, in invention relates to a device including a support defining one or more wells for holding a liquid sample, the sample comprising magnetic particles and an analyte, the magnetic particles having binding moieties linked thereto, wherein the binding moieties are operative to alter an aggregation of said magnetic particles in the liquid sample as a function of the presence or concentration of the analyte in the liquid sample, and wherein at least one of the wells has a varying cross section such that, in the presence of a magnetic field, aggregations of the particles move from an area of larger cross section to an area of smaller cross section, thereby concentrating the analyte carried with the aggregations. The description of elements of the embodiments above can be applied to this aspect of the invention as well.

In certain embodiments, the device includes, for each of the one or more wells, an RF coil disposed about the well and an electrical element in communication with the RF coil, wherein the RF coil is configured to detect an echo response produced by exposing the liquid sample in the well to a bias magnetic field created using one or more magnets and an RF excitation, wherein the electrical element is configured to at least partially condition a signal corresponding to the echo response. In preferred embodiments, at least one of the binding moieties is operative to bind to at least one of the following (thereby producing the aggregations): (i) the analyte; (ii) another of the binding moieties; (iii) an aggregation-inducing molecule in the liquid sample.

The binding moieties may include one or more species of one or more of the following: an amino acid, a nucleic acid, an oligonucleotide, a therapeutic agent, a metabolite of a therapeutic agent, a peptide, a polypeptide, a protein, a carbohydrate, a polysaccharide, a virus, and/or bacteria.

The analyte may include one or more species of one or more of the following: a protein, a peptide, a polypeptide, an amino acid, a nucleic acid, an oligonucleotide, a therapeutic agent, a metabolite of a therapeutic agent, RNA, DNA, an antibody, an organism, a virus, bacteria, a carbohydrate, a polysaccharide, and glucose. The analyte may also include, for example, a lipid, a gas (e.g., oxygen, carbon dioxide), an electrolyte (e.g., sodium, potassium, calcium, ammonia, lactate, lactic acid), a lipoprotein, cholesterol, a fatty acid, a glycoprotein, a proteoglycan, and/or a lipopolysaccharide. Furthermore, "detection of an analyte" may also mean measurement of physical properties of a solution containing one or more analytes, for example, measurement of dipole moment, ionization, solubility/saturation, viscosity, gellation, crystallization, and/or phase changes of the solution.

In another aspect, the invention relates to a device for detection of an analyte, the device including a support defining a well for holding a liquid sample including magnetic particles and the analyte, the magnetic particles having binding moieties linked thereto; and an RF coil disposed about the liquid sample, the RF coil configured to detect an echo response produced by exposing the liquid sample to a bias magnetic field created using one or more magnets and an RF excitation, the well and the RF coil configured to provide a filling factor of at least about 0.1. In certain embodiments, the filling factor is at least about 0.7, at least about 0.9, at least about 0.95, or about 1. The description of elements of the embodiments above can be applied to this aspect of the invention as well.

In another aspect, the invention relates to a device for detection of an analyte, the device including a support defining a well for holding a liquid sample including magnetic particles and the analyte, the magnetic particles having binding moieties linked thereto; and an RF coil disposed about the liquid sample, the RF coil configured to detect an echo response produced by exposing the liquid sample to a bias magnetic field created using one or more magnets and an RF excitation, wherein at least one of the following is less than about 1 mL: (i) the volume circumscribed by the RF coil; (ii) the volume of the liquid sample. In certain embodiments either or both of (i) and (ii) is/are less than about 800 μL, less than about 700 μL, less than about 600 μL, less than about 500 μL, less than about 400 μL, less than about 300 μL, less than about 200 μL, less than about 100 μL, less than about 10 μL, less than about 1 μL, less than about 500 nL, less than about 300 nL, less than about 100 nL, less than about 50 nL, less than about 20 nL, less than about 5 nL, less than about 2 nL, or about 1 nL. The description of elements of the embodiments above can be applied to this aspect of the invention as well.

In another aspect, the invention relates to a device for detection of an analyte, the device including a support defining a well for holding a liquid sample including magnetic particles and the analyte, the magnetic particles having binding moieties linked thereto; an RF coil disposed about the liquid sample, the RF coil configured to detect an echo response produced by exposing the liquid sample to a bias magnetic field created using one or more magnets and an RF excitation; and an electrical element in communication with the RF coil, the electrical element configured to at least partially condition a signal corresponding to the echo response, wherein the RF coil is disposed sufficiently close to the electrical element to provide a Q factor of at least 1, where the Q factor (quality factor) is the ratio of the inductive reactance of the RF coil to its resistance at a given frequency, for example, the Larmor frequency. In certain embodiments, the Q factor is at least about 5, at least about 10, at least about 20, at least about 30, at least about 40, at least about 50, at least about 60, at least about 70, at least about 80, at least about 90, at least about 100, or at least about 125. The description of elements of the embodiments above can be applied to this aspect of the invention as well.

The RF coil may be integrated with the support that defines the well, where the RF coil is disposed about the well. The support may be a substrate, with the well etched from the substrate material. Alternatively, the support may form the base of the well, with the RF coil itself serving as part or all of one or more sides of the well. Preferably, the RF coil is disposed within one centimeter of the electrical element. In certain embodiments, the RF coil is disposed within 5 millimeters of the electrical element, within 3 millimeters of the electrical element, within 2 millimeters of the electrical element, within 1 millimeter of the electrical element, within 500 micrometers of the electrical element, within 100 micrometers of the electrical element, within 50 micrometers of the electrical element, or within 5 micrometers of the electrical element.

In another aspect, the invention relates to a method of measuring one or more analytes in a sample using any one of (or any combination of) the following devices:

(i) a device including: a support defining a well for holding a liquid sample including magnetic particles and the analyte, the magnetic particles having binding moieties linked thereto; and an RF coil disposed about the liquid sample, the RF coil configured to detect an echo response produced by exposing the liquid sample to a bias magnetic field created using one or more magnets and an RF excitation, wherein the RF coil has a characteristic dimension from about 10 μm to about 1000 μm;

(ii) a device including a plurality of wells for holding a liquid sample including magnetic particles and the analyte, the magnetic particles having binding moieties linked thereto, and, for each of the wells: an RF coil disposed about the well, the RF coil configured to detect an echo response produced by exposing the liquid sample in the well to a bias magnetic field created using one or more magnets and an RF excitation;

(iii) a device including a support defining one or more wells for holding a liquid sample; and disposed on the support, for reconstitution within the one or more wells, dried superparamagnetic particles having binding moieties linked thereto, where the binding moieties are operative to alter an aggregation of the magnetic particles in the liquid sample as a function of the presence or concentration of an analyte in the liquid sample;

(iv) a device including a support defining one or more wells for holding a liquid sample, the sample comprising magnetic particles and an analyte, the magnetic particles having binding moieties linked thereto, wherein the binding moieties are operative to alter an aggregation of said magnetic particles in the liquid sample as a function of the presence or concentration of the analyte in the liquid sample, and wherein at least one of the wells has a varying cross section such that, in the presence of a magnetic field, aggregations of the particles move from an area of larger cross section to an area of smaller cross section, thereby concentrating the analyte carried with the aggregations;

(v) a device including a support defining a well for holding a liquid sample including magnetic particles and the analyte, the magnetic particles having binding moieties linked thereto; and an RF coil disposed about the liquid sample, the RF coil configured to detect an echo response produced by exposing the liquid sample to a bias magnetic field created using one or more magnets and an RF excitation, the well and the RF coil configured to provide a filling factor of at least about 0.1;

(vi) a device including a support defining a well for holding a liquid sample including magnetic particles and the analyte, the magnetic particles having binding moieties linked thereto; and an RF coil disposed about the liquid sample, the RF coil configured to detect an echo response produced by exposing the liquid sample to a bias magnetic field created using one or more magnets and an RF excitation, wherein at least one of the following is less than about 1 mL: (A) the volume circumscribed by the RF coil; (B) the volume of the liquid sample; and/or (vii) a device including a support defining a well for holding a liquid sample including magnetic particles and the analyte, the magnetic particles having binding moieties linked thereto; an RF coil disposed about the liquid sample, the RF coil configured to detect an echo response produced by exposing the liquid sample to a bias magnetic field created using one or more magnets and an RF excitation; and an electrical element in communication with the RF coil, the electrical element configured to at least partially condition a signal corresponding to the echo response, wherein the RF coil is disposed sufficiently close to the electrical element to provide a Q factor of at least 1, where the Q factor (quality factor) is the ratio of the inductive reactance of the RF coil to its resistance at a given frequency, for example, the Larmor frequency. The description of elements of the embodiments above can be applied to this aspect of the invention as well.

In certain embodiments, the one or more analytes measured by the device(s) include one or more biologically active substances. In certain embodiments, the sample includes a research sample, a cell sample, and/or an organism-derived sample. In certain embodiments, the method is performed in vivo (for example, where the device is implantable). In certain embodiments, the measuring step includes determining the concentration of the one or more analytes in the sample. In certain embodiments, the measuring step includes detecting the presence of the one or more analytes in the sample. In certain embodiments, the measuring step includes continuously monitoring the one or more analytes, semi-continuously monitoring the one or more analytes, and/or intermittently monitoring the one or more analytes. In certain embodiments, the measuring step includes continuously monitoring the one or more analytes in vivo.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

While the invention is particularly shown and described herein with reference to specific examples and specific embodiments, it should be understood by those skilled in the art that various changes in form and detail may be made therein without departing from the spirit and scope of the invention.

FIG. 6A is a schematic diagram of an NMR system including a single well, according to an illustrative embodiment of the invention.

FIG. 6B is a schematic diagram of an NMR system including a multiple-well array, according to an illustrative embodiment of the invention.

DETAILED DESCRIPTION OF THE INVENTION

Figure 1:
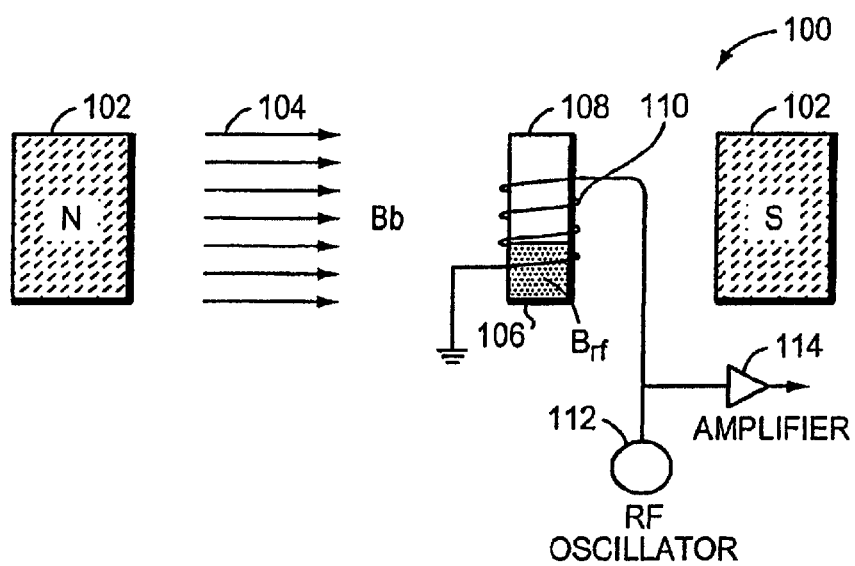
FIG. 1 is a schematic diagram of an NMR system for detection of an echo response of a sample to an RF excitation, according to an illustrative embodiment of the invention.
Figure 1:
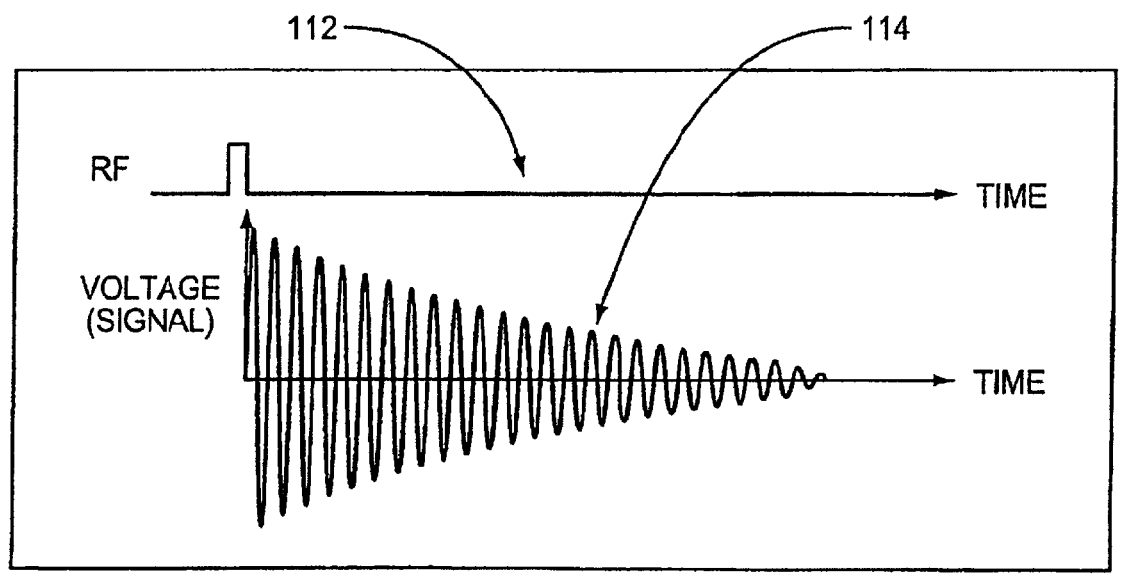

It is contemplated that devices, systems, methods, and processes of the claimed invention encompass variations and adaptations developed using information from the embodiments described herein. Adaptation and/or modification of the devices, systems, methods, and processes described herein may be performed by those of ordinary skill in the relevant art.

Throughout the description, where devices and systems are described as having, including, or comprising specific components, or where processes and methods are described as having, including, or comprising specific steps, it is contemplated that, additionally, there are devices and systems of the present invention that consist essentially of, or consist of, the recited components, and that there are processes and methods according to the present invention that consist essentially of, or consist of, the recited processing steps. Use of the term "about" with respect to any quantity is contemplated to include that quantity. For example, "about 10 µm" is contemplated herein to include "10 µm", as well as values understood in the art to be approximately 10 µm with respect to the entity described.

It should be understood that the order of steps or order for performing certain actions is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

As used herein, "nanoparticle" is understood to mean a particle having at least one dimension less than about 200 nm.

As used herein, "microparticle" is understood to mean a particle having at least one dimension less than about 200 µm.

As used herein, "characteristic dimension" of an entity is a dimension that is characteristic of the entity; for example, height is a characteristic dimension of a human being.

As used herein, "filling factor" is understood to mean the volume of the liquid sample in a well divided by the volume circumscribed by the RF coil.

As used herein, "quality factor" or "Q factor" of an RF coil is understood to be a measure of its efficiency as an inductor, and is defined as the ratio of the inductive reactance of the RF coil to its resistance at a given frequency, for example, the Larmor frequency.

As used herein, "linked" is understood to mean attached or bound by covalent bonds, non-covalent bonds, and/or linked via Van der Waals forces, hydrogen bonds, and/or other intermolecular forces.

The following headers are provided as a general organizational guide and do not serve to limit support for any given element of the invention to a particular section of the Description.

Nanoparticles

The nanoparticles described herein include those described in U.S. Patent Application Publication No. US 2003/0092029, the text of which is incorporated herein by reference. The nanoparticles may be in the form of conjugates, that is, a magnetic nanoparticle with one or more binding moieties (e.g. an oligonucleotide, nucleic acid, polypeptide, or polysaccharide) linked thereto. The binding moiety causes a specific interaction with a target analyte (or an aggregation-inducing molecule, such as avidin). The binding moiety specifically binds to a selected target analyte, for example, a nucleic acid, polypeptide, or polysaccharide, or the binding moiety can be designed to bind to another binding moiety to form an aggregate that is cleaved by the target molecule. Binding causes aggregation of the conjugates, resulting in a decrease of the spin-spin relaxation time (T2) of adjacent water protons in an aqueous solution (or free protons in a non-aqueous solvent). Cleavage causes dispersal of the aggregate into separate conjugates, resulting in an increase of the spin-spin relaxation time (T2) of adjacent water protons in an aqueous solution (or free protons in a non-aqueous solvent).

The conjugates have high relaxivity owing to the superparamagnetism of their iron or metal oxide. The conjugates have an R1 relaxivity from about 5 to about 30 $mM^{-1} sec^{-1}$, e.g., 10, 15, 20, or 25 $mM^{-1} sec^{-1}$. The conjugates have an R2 relaxivity between about 15 and 100 $mM^{-1} sec^{-1}$, e.g., 25, 50, 75, or 90 $mM^{-1} sec^{-1}$. The conjugates generally have a ratio of R2 to R1 from about 1.5 to about 4, e.g., about 2, 2.5, or 3. The conjugates generally have an iron oxide content that is greater than about 10% of the total mass of the particle, e.g., greater than 15, 20, 25 or 30 percent.

The nanoparticles can be monodisperse (a single crystal of a magnetic material, e.g., metal oxide, such as superparamagnetic iron oxide, per nanoparticle) or polydisperse (a plurality of crystals, e.g., 2, 3, or 4, per nanoparticle). The magnetic metal oxide can also comprise cobalt, magnesium, zinc, or mixtures of these metals with iron. The term "magnetic" as used herein means materials of high positive magnetic susceptibility such as paramagnetic compounds, superparamagnetic compounds, and magnetite, gamma ferric oxide, or metallic iron. Important features and elements of nanoparticles that are useful to produce conjugates include: (i) a high relaxivity, i.e., strong effect on water (or other solvent) relaxation, (ii) a functional group to which the binding moiety can be covalently attached, (iii) a low non-specific binding of interactive moieties to the nanoparticle, and/or (iv) stability in solution, i.e., the nanoparticles do not precipitate.

The nanoparticles may be linked to the binding moieties via functional groups. In some embodiments, the nanoparticles are associated with a polymer that includes the functional groups, and that also serves to keep the metal oxides dispersed from each other. The polymer can be a synthetic polymer, such as, but not limited to, polyethylene glycol or silane, natural polymers, or derivatives of either synthetic or natural polymers or a combination of these. The polymer may be hydrophilic. In some embodiments, the polymer "coating" is not a continuous film around the magnetic metal oxide, but is a "mesh" or "cloud" of extended polymer chains attached to and surrounding the metal oxide. The polymer can comprise polysaccharides and derivatives, including dextran, pullanan, carboxydextran, carboxmethyl dextran, and/or reduced carboxymethyl dextran. The metal oxide can be a collection of one or more crystals that contact each other, or that are individually entrapped or surrounded by the polymer.

In other embodiments, the nanoparticles are associated with non-polymeric functional group compositions. Methods of synthesizing stabilized, functionalized nanoparticles without associated polymers are described, for example, in Halbreich et al., Biochimie, 80 (5-6):379-90, 1998.

The nanoparticles may have an overall size of less than about 1-100 nm. The metal oxides may be in the form of crystals about 1-25 nm, e.g., about 3-10 nm, or about 5 nm in diameter. The polymer component in some embodiments can be in the form of a coating, e.g., about 5 to 20 nm thick or more. The overall size of the nanoparticles is about 15 to 200 nm, e.g., about 20 to 100 nm, about 40 to 60 nm; or about 50 nm.

The nanoparticles may be prepared in a variety of ways. It is preferred that the nanoparticle have functional groups that link the nanoparticle to the binding moiety.

Carboxy functionalized nanoparticles can be made, for example, according to the method of Gorman (see WO 00/61191). In this method, reduced carboxymethyl (CM) dextran is synthesized from commercial dextran. The CM-dextran and iron salts are mixed together and are then neutralized with ammonium hydroxide. The resulting carboxy functionalized nanoparticles can be used for coupling amino functionalized oligonucleotides.

Carboxy-functionalized nanoparticles can also be made from polysaccharide coated nanoparticles by reaction with bromo or chloroacetic acid in strong base to attach carboxyl groups. In addition, carboxy-functionalized particles can be made from amino-functionalized nanoparticles by converting amino to carboxy groups by the use of reagents such as succinic anhydride or maleic anhydride.

Nanoparticle size can be controlled by adjusting reaction conditions, for example, by using low temperature during the neutralization of iron salts with a base as described in U.S. Pat. No. 5,262,176. Uniform particle size materials can also be made by fractionating the particles using centrifugation, ultrafiltration, or gel filtration, as described, for example in U.S. Pat. No. 5,492,814.

Nanoparticles can also be synthesized according to the method of Molday (Molday, R. S. and D. MacKenzie, "Immunospecific ferromagnetic iron-dextran reagents for the labeling and magnetic separation of cells," J. Immunol. Methods, 1982, 52(3):353-67, and treated with periodate to form aldehyde groups. The aldehyde-containing nanoparticles can then be reacted with a diamine (e.g., ethylene diamine or hexanediamine), which will form a Schiff base, followed by reduction with sodium borohydride or sodium cyanoborohydride.

Dextran-coated nanoparticles can be made and cross-linked with epichlorohydrin. The addition of ammonia reacts with epoxy groups to generate amine groups, see Hogemann, D., et al., Improvement of MRI probes to allow efficient detection of gene expression Bioconjug. Chem. 2000, 11(6): 941-6, and Josephson et al., "High-efficiency intracellular magnetic labeling with novel superparamagnetic-Tat peptide conjugates," Bioconjug. Chem., 1999, 10(2):186-91. This material is known as cross-linked iron oxide or "CLIO" and when functionalized with amine is referred to as amine-CLIO or $NH_2$-CLIO.

Carboxy-functionalized nanoparticles can be converted to amino-functionalized magnetic particles by the use of water-soluble carbodiimides and diamines such as ethylene diamine or hexane diamine.

Avidin or streptavidin can be attached to nanoparticles for use with a biotinylated binding moiety, such as an oligonucleotide or polypeptide. See, e.g., Shen et al., "Magnetically labeled secretin retains receptor affinity to pancreas acinar cells," Bioconjug. Chem., 1996, 7(3):311-6. Similarly, biotin can be attached to a nanoparticle for use with an avidin-labeled binding moiety.

Low molecular weight compounds can be separated from the nanoparticles by ultra-filtration, dialysis, magnetic separation, or other means. The unreacted oligonucleotides can be separated from the oligonucleotide-nanoparticle conjugates, e.g., by magnetic separation or size exclusion chromatography.

Binding Moieties

In general, a binding moiety is a molecule, synthetic or natural, that specifically binds or otherwise links to, e.g., covalently or non-covalently binds to or hybridizes with, a target molecule, or with another binding moiety (or, in certain embodiments, with an aggregation inducing molecule). For example, the binding moiety can be a synthetic oligonucleotide that hybridizes to a specific complementary nucleic acid target. The binding moiety can also be an antibody directed toward an antigen or any protein-protein interaction. Also, the binding moiety can be a polysaccharide that binds to a corresponding target. In certain embodiments, the binding moieties can be designed or selected to serve, when bound to another binding moiety, as substrates for a target molecule such as enzyme in solution.

Binding moieties include, for example, oligonucleotide binding moieties, polypeptide binding moieties, antibody binding moieties, and polysaccharide binding moieties.

Oligonucleotide Binding Moieties

In certain embodiments, the binding moieties are oligonucleotides, attached/linked to the nanoparticles using any of a variety of chemistries, by a single, e.g., covalent, bond, e.g., at the 3' or 5' end to a functional group on the nanoparticle.

An oligonucleotide binding moiety can be constructed using chemical synthesis. A double-stranded DNA binding moiety can be constructed by enzymatic ligation reactions using procedures known in the art. For example, a nucleic acid (e.g., an oligonucleotide) can be chemically synthesized using naturally occurring nucleotides or variously modified nucleotides designed to increase the biological stability of the molecules or to increase the physical stability of the duplex formed between the complementary strands, e.g., phosphorothioate derivatives and acridine substituted nucleotides can be used. The nucleic acid also can be produced biologically using an expression vector into which a nucleic acid has been subcloned.

One method uses at least two populations of oligonucleotide magnetic nanoparticles, each with strong effects on water (or other solvent) relaxation. As the oligonucleotide-nanoparticle conjugates react with a target oligonucleotide, they form aggregates (e.g. 100-500 nm). Upon prolonged standing, e.g., overnight at room temperature, the aggregates form large clusters (micron-sized particles), which settle out of solution. Preferred embodiments use magnetic resonance to determine the relaxation properties of the solvent, which are altered when the mixture of magnetic oligonucleotide nanoparticles reacts with a target nucleic acid to form aggregates.

Certain embodiments employ a mixture of at least two types of magnetic metal oxide nanoparticles, each with a specific sequence of oligonucleotide, and each with more than one copy of the oligonucleotide attached, e.g., covalently, per nanoparticle. For example, the assay protocol may involve preparing a mixture of populations of oligonucleotide-nanoparticle conjugates and reacting the mixture with a target nucleic acid. Alternatively, oligonucleotide-nanoparticle conjugates can be reacted with the target in a sequential fashion. Certain embodiments feature the use of magnetic resonance to detect the reaction of the oligonucleotide-nanoparticle conjugates with the target nucleic acid. When a target is present, the dispersed conjugates self-assemble to form small aggregates.

For example, oligonucleotide binding moieties can be linked to the metal oxide through covalent attachment to a functionalized polymer or to non-polymeric surface-functionalized metal oxides. In the latter method, the nanoparticles can be synthesized according to the method of Albrecht et al., Biochimie, 80 (5-6): 379-90, 1998. Dimercapto-succinic acid is coupled to the iron oxide and provides a carboxyl functional group.

In certain embodiments, oligonucleotides are attached to magnetic nanoparticles via a functionalized polymer associated with the metal oxide. In some embodiments, the polymer is hydrophilic. In certain embodiments, the conjugates are made using oligonucleotides that have terminal amino, sulfhydryl, or phosphate groups, and superparamagnetic iron oxide nanoparticles bearing amino or carboxy groups on a hydrophilic polymer. There are several methods for synthesizing carboxy and amino derivatized-nanoparticles.

Polypeptide Binding Moieties

In certain embodiments, the binding moiety is a polypeptide (i.e., a protein, polypeptide, or peptide), attached, using any of a variety of chemistries, by a single covalent bond in such a manner so as to not affect the biological activity of the polypeptide. In one embodiment, attachment is done through the thiol group of single reactive cysteine residue so placed that its modification does not affect the biological activity of the polypeptide. In this regard the use of linear polypeptides, with cysteine at the C-terminal or N-terminal end, provides a single thiol in a manner similar to which alkanethiol supplies a thiol group at the 3' or 5' end of an oligonucleotide. Similar bifunctional conjugation reagents, such as SPDP and reacting with the amino group of the nanoparticle and thiol group of the polypeptide, can be used with any thiol bearing binding moiety. The types of polypeptides used as binding moieties can be antibodies, antibody fragments, and natural and synthetic polypeptide sequences, for example. The peptide binding moieties generally have a binding partner, that is, a molecule to which they selectively bind.

Use of peptides as binding moieties offers several advantages. For example, the mass per binding site is low. For example, up to twenty 2 kDa peptides can be attached to a nanoparticle, calculated assuming 2064 iron atoms per nanoparticle. With larger binding moieties like proteins (generally greater than about 30 kDa) the same mass of attached polypeptide results in only approximately 1-4 binding moieties per nanoparticle. Also, polypeptides can be engineered to have uniquely reactive residues, distal from the residues required for biological activity, for attachment to the nanoparticle. The reactive residue can be a cysteine thiol, an N-terminal amino group, a C-terminal carboxyl group or a carboxyl group of aspartate or glutamate, etc. A single reactive residue on the peptide is used to insure a unique site of attachment. These design principles can be followed with chemically synthesized peptides or biologically produced polypeptides.

The binding moieties can also contain amino acid sequences from naturally occurring (wild-type) polypeptides or proteins. For example, the natural polypeptide may be a hormone, (e.g., a cytokine, a growth factor), a serum protein, a viral protein (e.g., hemagglutinin), an extracellular matrix protein, a lectin, or an ectodomain of a cell surface protein. In general, the resulting binding moiety-nanoparticle is used to measure the presence of analytes in a test media reacting with the binding moiety.

Examples of protein hormones include: platelet-derived growth factor (PDGF) which binds the PDGF receptor; insulin-like growth factor-I and -II (Igf) which binds the Igf receptor; nerve growth factor (NGF) which binds the NGF receptor; fibroblast growth factor (FGF) which binds the FGF receptor (e.g., aFGF and bFGF); epidermal growth factor (EGF) which binds the EGF receptor; transforming growth factor (TGF, e.g., TGF-.alpha. and TGF-.beta.) which bind the TGF receptor; erythropoietin, which binds the erythropoitin receptor; growth hormone (e.g., human growth hormone) which binds the growth hormone receptor; and proinsulin, insulin, A-chain insulin, and B-chain insulin, which all bind to the insulin receptor.

Receptor binding moieties are useful for detecting and imaging receptor clustering on the surface of a cell. Useful ectodomains include those of the Notch protein, Delta protein, integrins, cadherins, and other cell adhesion molecules.

Antibody Binding Moieties

Other polypeptide binding moieties include immunoglobulin binding moieties that include at least one immunoglobulin domain, and typically at least two such domains. An "immunoglobulin domain" refers to a domain of a antibody molecule, e.g., a variable or constant domain. An "immunoglobulin superfamily domain" refers to a domain that has a three-dimensional structure related to an immunoglobulin domain, but is from a non-immunoglobulin molecule. Immunoglobulin domains and immunoglobulin superfamily domains typically include two .beta.-sheets formed of about seven .beta.-strands, and a conserved disulphide bond (see, e.g., Williams and Barclay 1988 Ann. Rev. Immunol. 6:381-

405). Proteins that include domains of the Ig superfamily domains include T cell receptors, CD4, platelet derived growth factor receptor (PDGFR), and intercellular adhesion molecule (ICAM).

One type of immunoglobulin binding moiety is an antibody. The term "antibody," as used herein, refers to a full-length, two-chain immunoglobulin molecule and an antigen-binding portion and fragments thereof, including synthetic variants. A typical antibody includes two heavy (H) chain variable regions (abbreviated herein as VH), and two light (L) chain variable regions (abbreviated herein as VL). The VH and VL regions can be further subdivided into regions of hypervariability, termed "complementarity determining regions" (CDR), interspersed with regions that are more conserved, termed "framework regions" (FR). The extent of the framework region and CDR's has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917). Each VH and VL is composed of three CDR's and four FRs, arranged from amino-terminus to carboxy-terminus in the following order: FR1, CDR1, FR2, CDR2, FR3, CDR3, FR4.

An antibody can also include a constant region as part of a light or heavy chain. Light chains can include a kappa or lambda constant region gene at the COOH-terminus (termed CL). Heavy chains can include, for example, a gamma constant region (IgG1, IgG2, IgG3, IgG4; encoding about 330 amino acids). A gamma constant region can include, e.g., CH1, CH2, and CH3. The term "full-length antibody" refers to a protein that includes one polypeptide that includes VL and CL, and a second polypeptide that includes VH, CH1, CH2, and CH3.

The term "antigen-binding fragment" of an antibody, as used herein, refers to one or more fragments of a full-length antibody that retain the ability to specifically bind to a target. Examples of antigen-binding fragments include, but are not limited to: (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also encompassed within the term "antigen-binding fragment."

In certain embodiments, the binding moiety is a polysaccharide, linked, for example, using any of a variety of chemistries, by a single bond, e.g., a covalent bond, at one of the two ends, to a functional group on the nanoparticle. The polysaccharides can be synthetic or natural. Mono-, di-, tri- and polysaccharides can be used as the binding moiety. These include, e.g., glycosides, N-glycosylamines, O-acyl derivatives, O-methyl derivatives, osazones, sugar alcohols, sugar acids, sugar phosphates when used with appropriate attachment chemistry to the nanoparticle.

A method of accomplishing linking is to couple avidin to a magnetic nanoparticle and react the avidin-nanoparticle with commercially available biotinylated polysaccharides, to yield polysaccharide-nanoparticle conjugates. For example, sialyl Lewis based polysaccharides are commercially available as biotinylated reagents and will react with avidin-CLIO (see Syntesome, Gesellschaft fur medizinische Biochemie mbH.). The sialyl Lewis x tetrasaccharide ($Sle^x$) is recognized by proteins known as selecting, which are present on the surfaces of leukocytes and function as part of the inflammatory cascade for the recruitment of leukocytes.

Still other targeting moieties include a non-proteinaceous element, e.g., a glycosyl modification (such as a Lewis antigen) or another non-proteinaceous organic molecule.

Biologically Active Substances

Embodiments of the invention include devices and/or systems for detecting and/or measuring the concentration of one or more analytes in a sample. The analyte(s) may include one or more biologically active substances and/or metabolite(s), marker(s), and/or other indicator(s) of biologically active substances. A biologically active substance may be described as a single entity or a combination of entities. The term "biologically active substance" includes without limitation, medications; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

Non-limiting examples of broad categories of useful biologically active substances include the following therapeutic categories: anabolic agents, antacids, anti-asthmatic agents, anti-cholesterolemic and anti-lipid agents, anti-coagulants, anti-convulsants, anti-diarrheals, anti-emetics, anti-infective agents, anti-inflammatory agents, anti-manic agents, anti-nauseants, anti-neoplastic agents, anti-obesity agents, antipyretic and analgesic agents, anti-spasmodic agents, antithrombotic agents, anti-uricemic agents, anti-anginal agents, antihistamines, anti-tussives, appetite suppressants, biologicals, cerebral dilators, coronary dilators, decongestants, diuretics, diagnostic agents, erythropoietic agents, expectorants, gastrointestinal sedatives, hyperglycemic agents, hypnotics, hypoglycemic agents, ion exchange resins, laxatives, mineral supplements, mucolytic agents, neuromuscular drugs, peripheral vasodilators, psychotropics, sedatives, stimulants, thyroid and anti-thyroid agents, uterine relaxants, vitamins, and prodrugs.

More specifically, non-limiting examples of useful biologically active substances include the following therapeutic categories: analgesics, such as nonsteroidal anti-inflammatory drugs, opiate agonists and salicylates; antihistamines, such as $H_1$-blockers and $H_2$-blockers; anti-infective agents, such as anthelmintics, antianaerobics, antibiotics, aminoglycoside antibiotics, antifungal antibiotics, cephalosporin antibiotics, macrolide antibiotics, miscellaneous .beta.-lactam antibiotics, penicillin antibiotics, quinolone antibiotics, sulfonamide antibiotics, tetracycline antibiotics, antimycobacterials, antituberculosis antimycobacterials, antiprotozoals, antimalarial antiprotozoals, antiviral agents, antiretroviral agents, scabicides, and urinary anti-infectives; antineoplastic agents, such as alkylating agents, nitrogen mustard alkylating agents, nitrosourea alkylating agents, antimetabolites, purine analog antimetabolites, pyrimidine analog antimetabolites, hormonal antineoplastics, natural antineoplastics, antibiotic natural antineoplastics, and vinca alkaloid natural antineoplastics; autonomic agents, such as anticholinergics, antimuscarinic anticholinergics, ergot alkaloids, parasympathomimetics, cholinergic agonist parasympathomimetics, cholinesterase inhibitor parasympathomimetics, sympatholytics, alpha-blocker sympatholytics, beta-blocker sympatholytics, sympathomimetics, and adrenergic agonist sympathomimetics; cardiovascular agents, such as antianginals, beta-blocker antianginals, calcium-channel blocker antianginals, nitrate antianginals, antiarrhythmics, cardiac glycoside antiarrhythmics, class I antiarrhythmics, class II antiarrhythmics, class III antiarrhythmics, class IV antiarrhythmics, antihypertensive agents, alpha-blocker antihypertensives, angiotensin-converting enzyme inhibitor (ACE inhibitor) antihypertensives, beta-blocker antihypertensives, calcium-channel blocker antihypertensives, central-acting adrenergic antihypertensives, diuretic antihypertensive agents, peripheral vasodilator antihypertensives, antilipemics, bile acid sequestrant antilipemics, HMG-COA reductase inhibitor antilipemics, inotropes, cardiac glycoside inotropes, and thrombolytic agents; dermatological agents, such as antihistamines, anti-inflammatory agents, corticosteroid anti-inflammatory agents, antipruritics/local anesthetics, topical anti-infectives, antifungal topical anti-infectives, antiviral topical anti-infectives, and topical antineoplastics; electrolytic and renal agents, such as acidifying agents, alkalinizing agents, diuretics, carbonic anhydrase inhibitor diuretics, loop diuretics, osmotic diuretics, potassium-sparing diuretics, thiazide diuretics, electrolyte replacements, and uricosuric agents; enzymes, such as pancreatic enzymes and thrombolytic enzymes; gastrointestinal agents, such as antidiarrheals, antiemetics, gastrointestinal anti-inflammatory agents, salicylate gastrointestinal anti-inflammatory agents, antacid anti-ulcer agents, gastric acid-pump inhibitor anti-ulcer agents, gastric mucosal anti-ulcer agents, $H_2$-blocker anti-ulcer agents, cholelitholytic agents, digestants, emetics, laxatives and stool softeners, and prokinetic agents; general anesthetics, such as inhalation anesthetics, halogenated inhalation anesthetics, intravenous anesthetics, barbiturate intravenous anesthetics, benzodiazepine intravenous anesthetics, and opiate agonist intravenous anesthetics; hematological agents, such as antianemia agents, hematopoietic antianemia agents, coagulation agents, anticoagulants, hemostatic coagulation agents, platelet inhibitor coagulation agents, thrombolytic enzyme coagulation agents, and plasma volume expanders; hormones and hormone modifiers, such as abortifacients, adrenal agents, corticosteroid adrenal agents, androgens, anti-androgens, antidiabetic agents, sulfonylurea antidiabetic agents, antihypoglycemic agents, oral contraceptives, progestin contraceptives, estrogens, fertility agents, oxytocics, parathyroid agents, pituitary hormones, progestins, antithyroid agents, thyroid hormones, and tocolytics; immunobiologic agents, such as immunoglobulins, immunosuppressives, toxoids, and vaccines; local anesthetics, such as amide local anesthetics and ester local anesthetics; musculoskeletal agents, such as anti-gout anti-inflammatory agents, corticosteroid anti-inflammatory agents, gold compound anti-inflammatory agents, immuno-suppressive anti-inflammatory agents, nonsteroidal anti-inflammatory drugs (NSAIDs), salicylate anti-inflammatory agents, skeletal muscle relaxants, neuromuscular blocker skeletal muscle relaxants, and reverse neuromuscular blocker skeletal muscle relaxants; neurological agents, such as anticonvulsants, barbiturate anticonvulsants, benzodiazepine anticonvulsants, anti-migraine agents, anti-parkinsonian agents, anti-vertigo agents, opiate agonists, and opiate antagonists; ophthalmic agents, such as anti-glaucoma agents, beta-blocker anti-glaucoma agents, miotic anti-glaucoma agents, mydriatics, adrenergic agonist mydriatics, antimuscarinic mydriatics, ophthalmic anesthetics, ophthalmic anti-infectives, ophthalmic aminoglycoside anti-infectives, ophthalmic macrolide anti-infectives, ophthalmic quinolone anti-infectives, ophthalmic sulfonamide anti-infectives, ophthalmic tetracycline anti-infectives, ophthalmic anti-inflammatory agents, ophthalmic corticosteroid anti-inflammatory agents, and ophthalmic nonsteroidal anti-inflammatory drugs (NSAIDs); psychotropic agents, such as antidepressants, heterocyclic antidepressants, monoamine oxidase inhibitors (MAOIs), selective serotonin re-uptake inhibitors (SSRIs), tricyclic antidepressants, antimanics, antipsychotics, phenothiazine antipsychotics, anxiolytics, sedatives, and hypnotics, barbiturate sedatives and hypnotics, benzodiazepine anxiolytics, sedatives, and hypnotics, and psychostimulants; respiratory agents, such as antitussives, bronchodilators, adrenergic agonist bronchodilators, antimuscarinic bronchodilators, expectorants, mucolytic agents, respiratory anti-inflammatory agents, and respiratory corticosteroid anti-inflammatory agents; toxicology agents, such as antidotes, heavy metal antagonists/chelating agents, substance abuse agents, deterrent substance abuse agents, and withdrawal substance abuse agents; minerals; and vitamins, such as vitamin A, vitamin B, vitamin C, vitamin D, vitamin E, and vitamin K.

Examples of classes of biologically active substances from the above categories include: nonsteroidal anti-inflammatory drugs (NSAIDs) analgesics, such as diclofenac, ibuprofen, ketoprofen, and naproxen; opiate agonist analgesics, such as codeine, fentanyl, hydromorphone, and morphine; salicylate analgesics, such as aspirin (ASA) (enteric coated ASA); $H_1$-blocker antihistamines, such as clemastine and terfenadine; $H_2$-blocker antihistamines, such as cimetidine, famotidine, nizadine, and ranitidine; anti-infective agents, such as mupirocin; antianaerobic anti-infectives, such as chloramphenicol and clindamycin; antifungal antibiotic anti-infectives, such as amphotericin b, clotrimazole, fluconazole, and ketoconazole; macrolide antibiotic anti-infectives, such as azithromycin and erythromycin; miscellaneous beta-lactam antibiotic anti-infectives, such as aztreonam and imipenem; penicillin antibiotic anti-infectives, such as nafcillin, oxacillin, penicillin G, and penicillin V; quinolone antibiotic anti-infectives, such as ciprofloxacin and norfloxacin; tetracycline antibiotic anti-infectives, such as doxycycline, minocycline, and tetracycline; antituberculosis antimycobacterial anti-infectives such as isoniazid (INH), and rifampin; antiprotozoal anti-infectives, such as atovaquone and dapsone; antimalarial antiprotozoal anti-infectives, such as chloroquine and pyrimethamine; anti-retroviral anti-infectives, such as ritonavir and zidovudine; antiviral anti-infective agents, such as acyclovir, ganciclovir, interferon alfa, and rimantadine; alkylating antineoplastic agents, such as carboplatin and cisplatin; nitrosourea alkylating antineoplastic agents, such as carmustine (BCNU); antimetabolite antineoplastic agents, such as methotrexate; pyrimidine analog antimetabolite antineoplastic agents, such as fluorouracil (5-FU) and gemcitabine; hormonal antineoplastics, such as goserelin, leuprolide, and tamoxifen; natural antineoplastics, such as aldesleukin, interleukin-2, docetaxel, etoposide (VP-16), interferon alfa, paclitaxel, and tretinoin (ATRA); antibiotic natural antineoplastics, such as bleomycin, dactinomycin, daunorubicin, doxorubicin, and mitomycin; vinca alkaloid natural antineoplastics, such as vinblastine and vincristine; autonomic agents, such as nicotine; anticholinergic autonomic agents, such as benztropine and trihexyphenidyl; antimuscarinic anticholinergic autonomic agents, such as atropine and oxybutynin; ergot alkaloid autonomic agents, such as bromocriptine; cholinergic agonist parasympathomimetics, such as pilocarpine; cholinesterase inhibitor parasympathomimetics, such as pyridostigmine; alpha-blocker sympatholytics, such as prazosin; 9-blocker sympatholytics, such as atenolol; adrenergic agonist sympathomimetics, such as albuterol and dobutamine; cardiovascular agents, such as aspirin (ASA) (enteric coated ASA); i-blocker antianginals, such as atenolol and propranolol; calcium-channel blocker antianginals, such as nifedipine and verapamil; nitrate antianginals, such as isosorbide dinitrate (ISDN); cardiac glycoside antiarrhythmics, such as digoxin; class I antiarrhythmics, such as lidocaine, mexiletine, phenyloin, procainamide, and quinidine; class II antiarrhythmics, such as atenolol, metoprolol, propranolol, and timolol; class III anitiarrhythmics, such as amiodarone; class IV antiarrhythmics, such as diltiazem and verapamil; alpha-blocker antihypertensives, such as prazosin; angiotensin-converting enzyme inhibitor (ACE inhibitor) antihypertensives, such as captopril and enalapril; beta-blocker antihypertensives, such as atenolol, metoprolol, nadolol, and propanolol; calcium-channel blocker antihypertensive agents, such as diltiazem and nifedipine; central-acting adrenergic antihypertensives, such as clonidine and methyldopa; diurectic antihypertensive agents, such as amiloride, furosemide, hydrochlorothiazide (HCTZ), and spironolactone; peripheral vasodilator antihypertensives, such as hydralazine and minoxidil; antilipemics, such as gemfibrozil and probucol; bile acid sequestrant antilipemics, such as cholestyramine; HMG-CoA reductase inhibitor antilipemics, such as lovastatin and pravastatin; inotropes, such as amrinone, dobutamine, and dopamine; cardiac glycoside inotropes, such as digoxin; thrombolytic agents, such as alteplase (TPA), anistreplase, streptokinase, and urokinase; dermatological agents, such as colchicine, isotretinoin, methotrexate, minoxidil, tretinoin (ATRA); dermatological corticosteroid anti-inflammatory agents, such as betamethasone and dexamethasone; antifungal topical anti-infectives, such as amphotericin B, clotrimazole, miconazole, and nystatin; antiviral topical anti-infectives, such as acyclovir; topical antineoplastics, such as fluorouracil (5-FU); electrolytic and renal agents, such as lactulose; loop diuretics, such as furosemide; potassium-sparing diuretics, such as triamterene; thiazide diuretics, such as hydrochlorothiazide (HCTZ); uricosuric agents, such as probenecid; enzymes such as RNase and DNase; thrombolytic enzymes, such as alteplase, anistreplase, streptokinase and urokinase; antiemetics, such as prochlorperazine; salicylate gastrointestinal anti-inflammatory agents, such as sulfasalazine; gastric acid-pump inhibitor anti-ulcer agents, such as omeprazole; $H_2$-blocker anti-ulcer agents, such as cimetidine, famotidine, nizatidine, and ranitidine; digestants, such as pancrelipase; prokinetic agents, such as erythromycin; opiate agonist intravenous anesthetics such as fentanyl; hematopoietic antianemia agents, such as erythropoietin, filgrastim (G-CSF), and sargramostim (GM-CSF); coagulation agents, such as antihemophilic factors 1-10 (AHF 1-10); anticoagulants, such as warfarin; thrombolytic enzyme coagulation agents, such as alteplase, anistreplase, streptokinase and urokinase; hormones and hormone modifiers, such as bromocriptine; abortifacients, such as methotrexate; antidiabetic agents, such as insulin; oral contraceptives, such as estrogen and progestin; progestin contraceptives, such as levonorgestrel and norgestrel; estrogens such as conjugated estrogens, diethylstilbestrol (DES), estrogen (estradiol, estrone, and estropipate); fertility agents, such as clomiphene, human chorionic gonadatropin (HCG), and menotropins; parathyroid agents such as calcitonin; pituitary hormones, such as desmopressin, goserelin, oxytocin, and vasopressin (ADH); progestins, such as medroxyprogesterone, norethindrone, and progesterone; thyroid hormones, such as levothyroxine; immunobiologic agents, such as interferon beta-1b and interferon gamma-1b; immunoglobulins, such as immune globulin IM, IMIG, IGIM and immune globulin IV, IVIG, IGIV; amide local anesthetics, such as lidocaine; ester local anesthetics, such as benzocaine and procaine; musculoskeletal corticosteroid anti-inflammatory agents, such as beclomethasone, betamethasone, cortisone, dexamethasone, hydrocortisone, and prednisone; musculoskeletal anti-inflammatory immunosuppressives, such as azathioprine, cyclophosphamide, and methotrexate; musculoskeletal nonsteroidal anti-inflammatory drugs (NSAIDs), such as diclofenac, ibuprofen, ketoprofen, ketorlac, and naproxen; skeletal muscle relaxants, such as baclofen, cyclobenzaprine, and diazepam; reverse neuromuscular blocker skeletal muscle relaxants, such as pyridostigmine; neurological agents, such as nimodipine, riluzole, tacrine and ticlopidine; anticonvulsants, such as carbamazepine, gabapentin, lamotrigine, phenyloin, and valproic acid; barbiturate anticonvulsants, such as phenobarbital and primidone; benzodiazepine anticonvulsants, such as clonazepam, diazepam, and lorazepam; anti-parkisonian agents, such as bromocriptine, levodopa, carbidopa, and pergolide; anti-vertigo agents, such as meclizine; opiate agonists, such as codeine, fentanyl, hydromorphone, methadone, and morphine; opiate antagonists, such as naloxone; beta-blocker anti-glaucoma agents, such as timolol; miotic anti-glaucoma agents, such as pilocarpine; ophthalmic aminoglycoside antiinfectives, such as gentamicin, neomycin, and tobramycin; ophthalmic quinolone anti-infectives, such as ciprofloxacin, norfloxacin, and ofloxacin; ophthalmic corticosteroid anti-inflammatory agents, such as dexamethasone and prednisolone; ophthalmic nonsteroidal anti-inflammatory drugs (NSAIDs), such as diclofenac; antipsychotics, such as clozapine, haloperidol, and risperidone; benzodiazepine anxiolytics, sedatives and hypnotics, such as clonazepam, diazepam, lorazepam, oxazepam, and prazepam; psychostimulants, such as methylphenidate and pemoline; antitussives, such as codeine; bronchodilators, such as theophylline; adrenergic agonist bronchodilators, such as albuterol; respiratory corticosteroid anti-inflammatory agents, such as dexamethasone; antidotes, such as flumazenil and naloxone; heavy metal antagonists/chelating agents, such as penicillamine; deterrent substance abuse agents, such as disulfuram, naltrexone, and nicotine; withdrawal substance abuse agents, such as bromocriptine; minerals, such as iron, calcium, and magnesium; vitamin B compounds, such as cyanocobalamin (vitamin $B_{12}$) and niacin (vitamin $B_3$); vitamin C compounds, such as ascorbic acid; and vitamin D compounds, such as calcitriol; recombinant beta-glucan; bovine immunoglobulin concentrate; bovine superoxide dismutase; the formulation comprising fluorouracil, epinephrine, and bovine collagen; recombinant hirudin (r-Hir), HIV-1 immunogen; human anti-TAC antibody; recombinant human growth hormone (r-hGH); recombinant human hemoglobin (r-Hb); recombinant human mecasermin (r-IGF-1); recombinant interferon beta-1a; lenograstim (G-CSF); olanzapine; recombinant thyroid stimulating hormone (r-TSH); topotecan; acyclovir sodium; aldesleukin; atenolol; bleomycin sulfate, human calcitonin; salmon calcitonin; carboplatin; carmustine; dactinomycin, daunorubicin HCl; docetaxel; doxorubicin HCl; epoetin alfa; etoposide (VP-16); fluorouracil (5-FU); ganciclovir sodium; gentamicin sulfate; interferon alfa; leuprolide acetate; meperidine HCl; methadone HCl; methotrexate sodium; paclitaxel; ranitidine HCl; vinblastin sulfate; and zidovudine (AZT).

Further specific examples of biologically active substances from the above categories include: antineoplastics such as androgen inhibitors, antimetabolites, cytotoxic agents, and immunomodulators; anti-tussives such as dextromethorphan, dextromethorphan hydrobromide, noscapine, carbetapentane citrate, and chlorphedianol hydrochloride; antihistamines such as chlorpheniramine maleate, phenindamine tartrate, pyrilamine maleate, doxylamine succinate, and phenyltoloxamine citrate; decongestants such as phenylephrine hydrochloride, phenylpropanolamine hydrochloride, pseudoephedrine hydrochloride, and ephedrine; various alkaloids such as codeine phosphate, codeine sulfate and morphine; mineral supplements such as potassium chloride, zinc chloride, calcium carbonates, magnesium oxide, and other alkali metal and alkaline earth metal salts; ion exchange resins such as cholestryramine; anti-arrhythmics such as N-acetylprocainamide; antipyretics and analgesics such as acetaminophen, aspirin and ibuprofen; appetite suppressants such as phenylpropanolamine hydrochloride or caffeine; expectorants such as guaifenesin; antacids such as aluminum hydroxide and magnesium hydroxide; biologicals such as peptides, polypeptides, proteins and amino acids, hormones, interferons or cytokines, and other bioactive peptidic compounds, such as interleukins 1-18 including mutants and analogues, RNase, DNase, luteinizing hormone releasing hormone (LHRH) and analogues, gonadotropin releasing hormone (GnRH), transforming growth factor-beta (TGF-beta), fibroblast growth factor (FGF), tumor necrosis factor-alpha & beta (TNF-alpha & beta), nerve growth factor (NGF), growth hormone releasing factor (GHRF), epidermal growth factor (EGF), fibroblast growth factor homologous factor (FGFHF), hepatocyte growth factor (HGF), insulin growth factor (IGF), invasion inhibiting factor-2 (IIF-2), bone morphogenetic proteins 1-7 (BMP 1-7), somatostatin, thymosin-.alpha.-1, T-globulin, superoxide dismutase (SOD), complement factors, hGH, tPA, calcitonin, ANF, EPO and insulin; and anti-infective agents such as antifungals, anti-virals, antiseptics and antibiotics.

Biologically active substances also include radiosensitizers, such as metoclopramide, sensamide or neusensamide (manufactured by Oxigene); profiromycin (made by Vion); RSR13 (made by Allos); Thymitaq (made by Agouron), etanidazole or lobenguane (manufactured by Nycomed); gadolinium texaphrin (made by Pharmacyclics); BuDR/Broxine (made by NeoPharm); IPdR (made by Sparta); CR2412 (made by Cell Therapeutic); L1X (made by Terrapin); or the like.

Biologically active substances include medications for the gastrointestinal tract or digestive system, for example, antacids, reflux suppressants, antiflatulents, antidoopaminergics, proton pump inhibitors, H2-receptor antagonists, cytoprotectants, prostaglandin analogues, laxatives, antispasmodics, antidiarrheals, bile acid sequestrants, and opioids; medications for the cardiovascular system, for example, beta-receptor blockers, calcium channel blockers, diuretics, cardiac glycosides, antiarrhythmics, nitrate, antianginals, vascoconstrictors, vasodilators, peripheral activators, ACE inhibitors, angiotensin receptor blockers, alpha blockers, anticoagulants, heparin, HSGAGs, antiplatelet drugs, fibrinolytics, anti-hemophilic factors, haemostatic drugs, hypolipaemic agents, and statins; medications for the central nervous system, for example, hypnotics, anaesthetics, antipsychotics, antidepressants, anti-emetics, anticonvulsants, antiepileptics, anxiolytics, barbiturates, movement disorder drugs, stimulants, benzodiazepine, cyclopyrrolone, dopamine antagonists, antihistamine, cholinergics, anticholinergics, emetics, cannabinoids, 5-HT antagonists; medications for pain and/or consciousness, for example, NSAIDs, opioids and orphans such as paracetamol, tricyclic antidepressants, and anticonvulsants; for musculo-skeletal disorders, for example, NSAIDs, muscle relaxants, and neuromuscular drug anticholinersterase; medications for the eye, for example, adrenergic neurone blockers, astringents, ocular lubricants, topical anesthetics, sympathomimetics, parasympatholytics, mydriatics, cycloplegics, antibiotics, topical antibiotics, sulfa drugs, aminoglycosides, fluoroquinolones, anti-virals, anti-fungals, imidazoles, polyenes, NSAIDs, corticosteroids, mast cell inhibitors, adrenergic agonists, beta-blockers, carbonic anhydrase inhibitors/hyperosmotiics, cholinergics, miotics, parasympathomimetics, prostaglandin, agonists/prostaglandin inhibitors, nitroglycerin; medications for the ear, nose and oropharynx, for example, sympathomimetics, antihistamines, anticholinergics, NSAIDs, steroids, antiseptics, local anesthetics, antifungals, cerumenolytics; medications for the respiratory system, for example, bronchodilators, NSAIDs, anti-allergics, antitussives, mucolytics, decongestants, corticosteroids, beta-receptor antagonists, anticholinergics, steroids; medications for endocrine problems, for example, androgen, antiandrogen, gonadotropin, corticosteroids, growth hormone, insulin, antidiabetics, thyroid hormones, antithyroid drugs, calcitonin, diphosphonate, and vasopressin analogues; medications for the reproductive system or urinary system, for example, antifungals, alkalising agents, quinolones, antibiotics, cholinergics, anticholinergics, anticholinesterase, antispasmodics, 5-alpha reductase inhibitor, selective alpha-1 blockers, and sildenafil; medications for contraception, for example, oral contraceptives, spermicides, and depot contraceptives; medications for obstetrics and gynacology, for example, NSAIDs, anticholinergics, haemostatic drugs, antifibrinolytics, hormone replacement therapy, bone regulator, beta-receptor agonists, follicle stimulating hormone, luteinising hormone, LHRH gamolenic acid, gonadotropin release inhibitor, progestogen, dopamine agonist, oestrogen, prostaglandin, gonadorelin, clomiphene, tammoxifen, and diethylstilbestrol; medications for the skin, for example, emollients, anti-pruritics, antifungals, disinfectants, scabicide, pediculicide, tar products, vitamin A derivatives, vitamin D analogue, keratolytics, abrasives, systemic antibiotics, topical antibiotics, hormones, desloughing agents, exudate absorbents, fibrinolytics, proteolytics, sunscreens, antiperspirants, and corticosteroids; medications for infections and infestations, for example, antibiotics, antifungals, antileprotics, antituberculous drugs, antimalarials, anthelmintics, amoebicide, antivirals, antiprotozoals, and antiserum; medications for the immune system, for example, vaccines, immunoglobulin, immunosuppressants, interferon, monoclonal antibodies; medications for allergic disorders, for example, anti-allergics, antihistamines, and NSAIDs; medications for nutrition, for example, tonics, iron preparations, electrolytes, vitamins, anti-obesity drugs, anabolic drugs, haematopoietic drugs, and food product drugs; medications for neoplastic disorders, for example, cytotoxic drugs, sex hormones, aromatase inhibitors, somatostatin inhibitors, recombinant interleukins, G-CSF, and erythropoietin; medications for diagnostics, for example, contrast agents; and medications for cancer (anti-cancer agents).

Examples of pain medications (e.g. analgesics) include opioids such as buprenorphine, butorphanol, dextropropoxyphene, dihydrocodeine, fentanyl, diamorphine (heroin), hydromorphone, morphine, nalbuphine, oxycodone, oxymorphone, pentazocine, pethidine (meperidine), and tramadol; salicylic acid and derivatives such as acetylsalicylic acid (aspirin), diflunisal, and ethenzamide; pyrazolones such as aminophenazone, metamizole, and phenazone; anilides such as paracetamol (acetaminophen), phenacetin; and others such as ziconotide and tetradyrocannabinol.

Examples of blood pressure medications (e.g. antihypertensives and diuretics) include antiadrenergic agents such as clonidine, doxazosin, guanethidine, guanfacine, mecamylamine, methyldopa, moxonidinie, prazosin, rescinnamine, and reserpine; vasodilators such as diazoxide, hydralazine, minoxidil, and nitroprusside; low ceiling diuretics such as bendroflumethiazide, chlorothiazide, chlortalidone, hydrochlorothiazide, indapamide, quinethazone, mersalyl, metolazone, and theobromine; high ceiling diuretics such as bumetanide, furosemide, and torasemide; potassium-sparing diuretics such as amiloride, eplerenone, spironolactone, and triamterene; and other antihypertensives such as bosentan and ketanserin.

Examples of anti-thrombotics (e.g. thrombolytics, anticoagulants, and antiplatelet drugs) include vitamin K antagonists such as acenocoumarol, clorindione, dicumarol, diphenadione, ethyl biscoumacetate, phenprocoumon, phenindione, tioclomarol, and warfarin; heparin group (platelet aggregation inhibitors) such as antithrombin III, bemiparin, dalteparin, danaparoid, enoxaparin, heparin, nadroparin, parnaparin, reviparin, sulodexide, and tinzaparin; other platelet aggregation inhibitors such as abciximab, acetylsalicylic acid (aspirin), aloxiprin, beraprost, ditazole, carbasalate calcium, cloricromen, clopidogrel, dipyridamole, epoprostenol, eptifibatide, indobufen, iloprost, picotamide, prasugrel, ticlopidine, tirofiban, treprostinil, and triflusal; enzymes such as alteplase, ancrod, anistreplase, brinase, drotrecogin alfa, fibrinolysin, procein C, reteplase, saruplase, streptokinase, tenecteplase, and urokinase; direct thrombin inhibitors such as argatroban, bivalirudin, desirudin, lepirudin, melagatran, and ximelagatran; other antithrombotics such as dabigatran, defibrotide, dermatan sulfate, fondaparinux, and rivaroxaban; and others such as citrate, EDTA, and oxalate.

Examples of anticonvulsants include barbiturates such as barbexaclone, metharbital, methylphenobarbital, phenobarbital, and primidone; hydantoins such as ethotoin, fosphenyloin, mephenyloin, and phenyloin; oxazolidinediones such as ethadione, paramethadione, and trimethadione; succinimides such as ethosuximide, mesuximide, and phensuximide; benzodiazepines such as clobazam, clonazepam, clorazepate, diazepam, lorazepam, midazolam, and nitrazepam; carboxamides such as carbamazepine, oxcarbazepine, rufinamide; fatty acid derivatives such as valpromide and valnoctamide; carboxylic acids such as valproic acid, tiagabine; GABA analogs such as gabapentin, pregabalin, progabide, and givabatrin; monosaccharides such as topiramate; aromatic allyllic alcohols such as stiripentol; ureas such as phenacemide and pheneturide; carbamates such as emylcamate, felbamate, and meprobamate; pyrrolidines such as brivaracetam, levetiracetam, nefiracetam, and seletracetam; sulfa drugs such as acetazolamide, ethoxzolamide, sultiame, and zonisamide; propionates such as beclamide; aldehydes such as paraldehyde; and bromides such as potassium bromide.

Examples of anti-cancer agents include acivicin; aclarubicin; acodazole hydrochloride; acronine; adriamycin; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interferon alfa-2a; interferon alfa-2b; interferon alfa-n1; interferon alfa-n3; interferon beta-1a; interferon gamma-I b; iproplatin; irinotecan hydrochloride; lanreotide acetate; letrozole; leuprolide acetate; liarozole hydrochloride; lometexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; topotecan hydrochloride; toremifene citrate; trestolone acetate; triciribine phosphate; trimetrexate; trimetrexate glucuronate; triptorelin; tubulozole hydrochloride; Uracil mustard; rredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other biologically active substances include those mentioned in *Basic and Clinical Pharmacology* (LANGE Basic Science), Katzung and Katzung, ISBN 0071410929, McGraw-Hill Medical, 9$^{th}$ edition (2003).

Medical Conditions

Embodiments of the invention may be used in the monitoring of one or more biologically active substance(s) in the diagnosis, management, and/or treatment of any of a wide range of medical conditions. Various categories of medical conditions include, for example, disorders of pain; of alterations in body temperature (e.g., fever); of nervous system dysfunction (e.g., syncope, myalgias, movement disorders, numbness, sensory loss, delirium, dimentioa, memory loss, sleep disorders); of the eyes, ears, nose, and throat; of circulatory and/or respiratory functions (e.g., dysplnea, pulmonary edema, cough, hemoptysis, hypertension, myocardial infarctions, hypoxia, cyanosis, cardiovascular collapse, congestive heart failure, edema, shock); of gastrointestinal function (e.g., dysphagia, diarrhea, constipation, GI bleeding, jaundice, ascites, indigestion, nausea, vomiting); of renal and urinary tract function (e.g., acidosis, alkalosis, fluid and electrolyte imbalances, azotemia, urinary abnormalities); of sexual function and reproduction (e.g., erectile dysfunction, menstrual disturbances, hirsutism, virilization, infertility, pregnancy associated disorders and standard measurements); of the skin (e.g., eczema, psoriasis, acne, rosacea, cutaneous infection, immunological skin diseases, photosensitivity); of the blood (e.g., hematology); of genes (e.g., genetic disorders); of drug response (e.g., adverse drug responses); and of nutrition (e.g., obesity, eating disorders, nutritional assessment). Other medical fields with which embodiments of the invention find utility include oncology (e.g., neoplasms, malignancies, angiogenesis, paraneoplasic syndromes, oncologic emergencies); hematology (e.g., anemia, hemoglobinopathies, megaloblastic anemias, hemolytic anemias, aplastic anemia, myelodysplasia, bone marrow failure, polycythemia vera, myloproliferative diseases, acute myeloid leukemia, chronic myeloid leukemia, lymphoid malignancies, plasma cell disorders, transfusion biology, transplants); hemostasis (e.g., disorders of coagulation and thrombosis, disorders of the platelet and vessel wall); and infectious diseases (e.g., sepsis, septic shock, fever of unknown origin, endocardidtis, bites, burns, osteomyelitis, abscesses, food poisoning, peliv inflammatory disease, bacterial (gram positive, gram negative, miscellaneous (nocardia, actimoyces, mixed), mycobacterial, spirochetal, rickettsia, mycoplasma); chlamydia; viral (DNA, RNA), fungal and algal infections; protozoal and helminthic infections; endocrine diseases; nutritional diseases; and metabolic diseases.

Other medical conditions and/or fields with which embodiments of the invention find utility include those mentioned in *Harrison's Principles of Internal Medicine*, Kasper et al., ISBN 0071402357, McGraw-Hill Professional, 16$^{th}$ edition (2004), as well as those mentioned in *Robbins Basic Pathology*, Kumar, Cotran, and Robbins, eds., ISBN 1416025340, Elsevier, 7$^{th}$ edition (2005).

Medical tests (e.g. blood tests, urine tests, and/or other human or animal tissue tests) that may be performed using various embodiments of the invention described herein include, for example, general chemistry tests (e.g., analytes include albumin, blood urea nitrogen, calcium, creatinine, magnesium, phosphorus, total protein, and/or uric acid); electrolyte tests (e.g., analytes include sodium, potassium, chloride, and/or carbon dioxide); diabetes tests (e.g., analytes include glucose, hemoglobin A1C, and/or microalbumin); lipids tests (e.g., analytes include apolipoprotein A1, apolipoprotein B, cholesterol, triglyceride, low density lipoprotein cholesteral, and/or high density lipoprotein cholesterol); nutritional assessment (e.g., analytes include albumin, prealbumin, transferrin, retinol binding protein, alpha1-acid glycoprotein, and/or ferritin); hepatic tests (e.g., analytes include alanine transaminase, albumin, alkaline phosphatase, aspartate transaminase, direct bilirubin, gamma glutamyl transaminase, lactate dehydrogenase, immunoglobulin A, immunoglobulin G, immunoglobulin M, prealbumin, total bilirubin, and/or total protein); cardiac tests (e.g., analytes include apolipoprotein A1, apolipoprotein B, cardiac troponin-1, creatine kinase, creatine kinase MB isoenzyme, high sensitivity CRP, mass creatine kinase MB isoenzyme myoglobin, and/or N-terminal pro-brain natriuretic peptide); tests for anemia (e.g., analytes include ferritin, folate, homocysteine, haptoglobin, iron, soluble transferrin receptor, total iron binding capacity, transferrin, and/or vitamin B12); pancreatic tests (e.g., analytes include amylase and/or lipase); nephropathies (e.g., analytes include albumin, alpha1-microglobulin, alpha2-macroglobulin, beta2-microglobulin, cystatin C, retinol binding protein, and/or transferrin); bone tests (e.g., analytes include alkaline phosphatase, calcium, and/or phosphorous); cancer marker monitoring (e.g., analytes include total PSA); thyroid tests (e.g., analytes include free thyroxine, free triiodothyronine, thyroxine, thyroid stimulating hormone, and/or triiodothyronine); fertility tests (e.g., analytes include beta-human chorionic gonadotropin); therapeutic drug monitoring (e.g., analytes include carbamazepine, digoxin, digitoxin, gentamicin, lidocaine, lithium, N-acetyl procainamide, phenobarbital, phenyloin, procainamide, theophylline, tobramycin, valproic acid, and/or vancomycin); immunosuppressive drugs (e.g., analytes include cyclosporine A, sirolimus, and/or tacrolimus); tests for complement activity and/or autoimmune disease (e.g., analytes include C3 complement, C4 complement, C1 inhibitor, C-reactive protein, and/or rheumatoid factor); polyclonal/monoclonal gammopathies (e.g., analytes include immunoglobulin A, immunoglobulin G, immunoglobulin M, 1 g light chains types kappa and/or lambda, immunoglobulin G subclasses 1, 2, 3, and/or 4); tests for infectious disease (e.g., analytes include antistreptolysin O); tests for inflammatory disorders (e.g., analytes include alpha1-acid glycoprotein, alpha1-antitrypsin, ceruloplasmin, C-reactive protein, and/or haptoglobin); allergy testing (e.g., analytes include immunoglobulin E); urine protein tests (e.g., analytes include alpha1-microglobulin, immunoglobulin G, 1 g light chains type kappa and/or lambda, microalbumin, and/or urinary/cerebrospinal fluid protein); tests for protein—CSF (e.g., analytes include immunoglobulin G and/or urinary/cerebrospinal fluid protein); toxicology tests (e.g., analytes include serum acetaminophene, serum barbiturates, serum benzodiazepines, serum salicylate, serum tricyclic antidepressants, and/or urine ethyl alcohol); and/or tests for drugs of abuse (e.g., analytes include amphetamine, cocaine, barbiturates, benzodiazepines, ecstacy, methadone, opiate, phencyclidine, tetrahydrocannabinoids, propoxyphene, and/or methaqualone). In certain embodiments, the NMR device may replace large, expensive integrated analyzers, for example, those that integrate chemiluminescence, nephelometry, photometry, and/or multisensor technologies. Other analytes include those mentioned in the *Tietz Textbook of Clinical Chemistry and Molecular Diagnostics*, Burtis, Ashwood, and Bruns, ISBN 0721601898, Elsevier, 4$^{th}$ edition (2006).

NMR Systems/Devices

FIG. 1 is a schematic diagram 100 of an NMR system for detection of an echo response of a liquid sample to an RF excitation, thereby detecting the presence and/or concentration of an analyte in the liquid sample. A bias magnet 102 establishes a bias magnetic field Bb 104 through a sample 106. The nanoparticles are in a lyophilized state in the sample well (the term "well" as used herein includes any indentation, container, or support) 108 until introduction of the liquid sample 106 into the well 108, or the nanoparticles can be added to the sample 106 prior to introduction of the liquid sample into the well 108. An RF coil 110 and RF oscillator 112 provides an RF excitation at the Larmor frequency which is a linear function of the bias magnetic field Bb. The RF coil 110 is wrapped around the sample well 108. The excitation RF creates instability in the spin of the water protons (or free protons in a non-aqueous solvent). When the RF excitation is turned off, the protons "relax" to their original state and emit an RF signal characteristic of the concentration of the analyte. The coil 110 acts as an RF antenna and detects an "echo" of the relaxation. The echo of interest is the decay in time (generally 10-300 milliseconds) and is called the T2 signal. The RF signal from the coil 110 is amplified 114 and processed to determine the T2 (decay time) response to the excitation in the bias field Bb. The well 108 may be a small capillary tube with microliters of the analyte and a microcoil wound around it. Alternatively, the coil may be configured as shown in any of FIGS. 2A-E about or in proximity to the well.

Figure 2A:
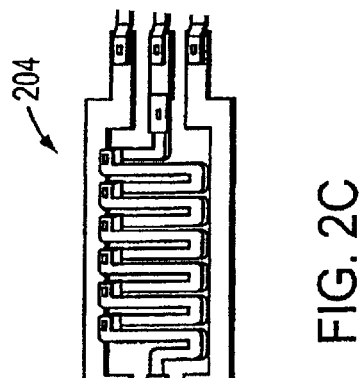
FIGS. 2A-2E illustrate micro NMR coil (RF coil) designs including a wound solenoid coil (FIG. 2A), a planar coil (FIG. 2B), a MEMS solenoid coil (FIG. 2C), a MEMS Helmholz coil (FIG. 2D), and a saddle coil (FIG. 2E), according to an illustrative embodiment of the invention.
Figure 2B:
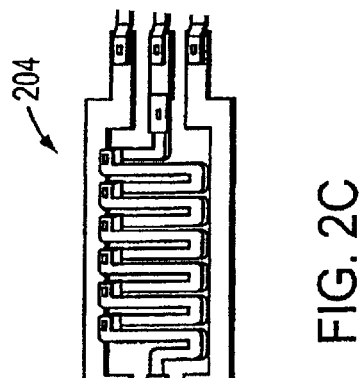
Figure 2C:
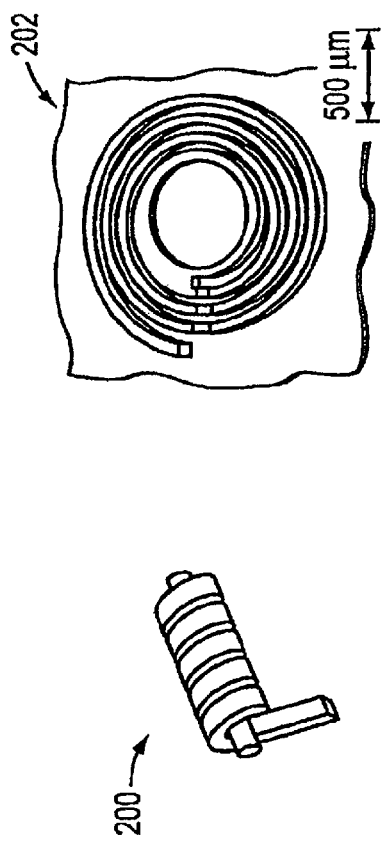
Figure 2D:
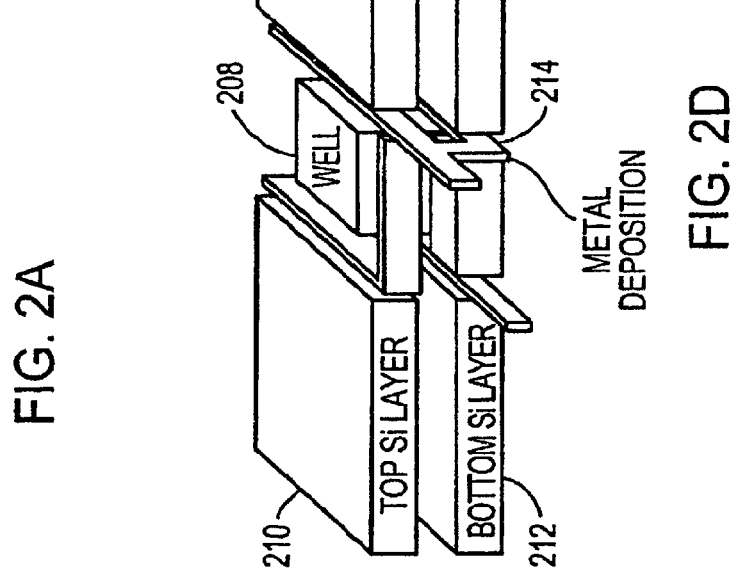
Figure 2E:
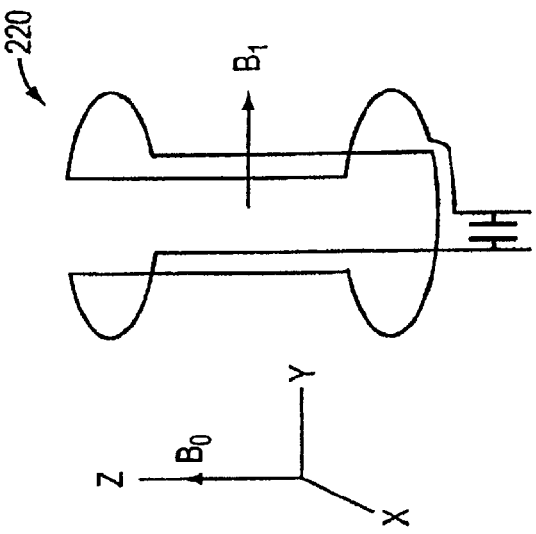

FIGS. 2A-E illustrate micro NMR coil (RF coil) designs. FIG. 2A shows a wound solenoid micro coil 200 about 100 μm in length. FIG. 2B shows a "planar" coil 202 (the coil is not truly planar, since the coil has finite thickness) about 1000 μm in diameter. FIG. 2C shows a MEMS solenoid coil 204 about 100 μm×500 μm length×width and defining a volume of about 0.02 μL. FIG. 2D shows a schematic of a MEMS Helmholtz coil 206 configuration, and FIG. 2E shows a schematic of a saddle coil 220 configuration.

A wound solenoid micro coil 200 used for traditional NMR (non-MRS) detection is described in Seeber et al., "Design and testing of high sensitivity micro-receiver coil apparatus for nuclear magnetic resonance and imaging," Ohio State University, Columbus, Ohio. A planar micro coil 202 used for traditional NMR detection is described in Massin et al., "High Q factor RF planar microcoil for micro-scale NMR spectroscopy," *Sensors and Actuators A* 97-98, 280-288 (2002). A Helmholtz coil configuration 206 features a well 208 for holding a sample, a top Si layer 210, a bottom Si layer 212, and deposited metal coils 214. An example of a Helmholtz coil configuration 206 used for traditional NMR detection is described in Syms et al, "MEMS Helmholz Coils for Magnetic Resonance Spectroscopy," *Journal of Micromechanics and Micromachining* 15 (2005) S1-S9.

The coil configuration may be chosen or adapted for specific implementation of the micro-NMR-MRS technology, since different coil configurations offer different performance characteristics. For example, each of these coil geometries has a different performance and field alignment. The planar coil 202 has an RF field perpendicular to the plane of the coil. The solenoid coil 200 has an RF field down the axis of the coil, and the Helmholtz coil 206 has an RF field transverse to the two rectangular coils 214. The Helmholtz 206 and saddle coils 220 have transverse fields which would allow the placement of the permanent magnet bias field above and below the well. Helmholtz 206 and saddle coils 220 may be most effective for the chip design, while the solenoid coil 200 may be most effective when the sample and MRS nanoparticles are held in a micro tube.

The micro-NMR devices may be fabricated by winding or printing the coils or by microelectromechanical system (MEMS) semiconductor fabrication techniques. For example, a wound or printed coil/sample well module may be about 100 μm in diameter, or as large as a centimeter or more. A MEMS unit or chip (thusly named since it is fabricated in a semiconductor process as a die on a wafer) may have a coil that is from about 10 μm to about 1000 μm in characteristic dimension, for example. The wound or printed coil/sample well configuration is referenced herein as a module and the MEMS version is referenced herein as a chip. For example, the liquid sample 108 may be held in a tube (for example, a capillary, pipette, or micro tube) with the coil wound around it, or it may be held in wells on the chip with the RF coil surrounding the well.

Figure 3:
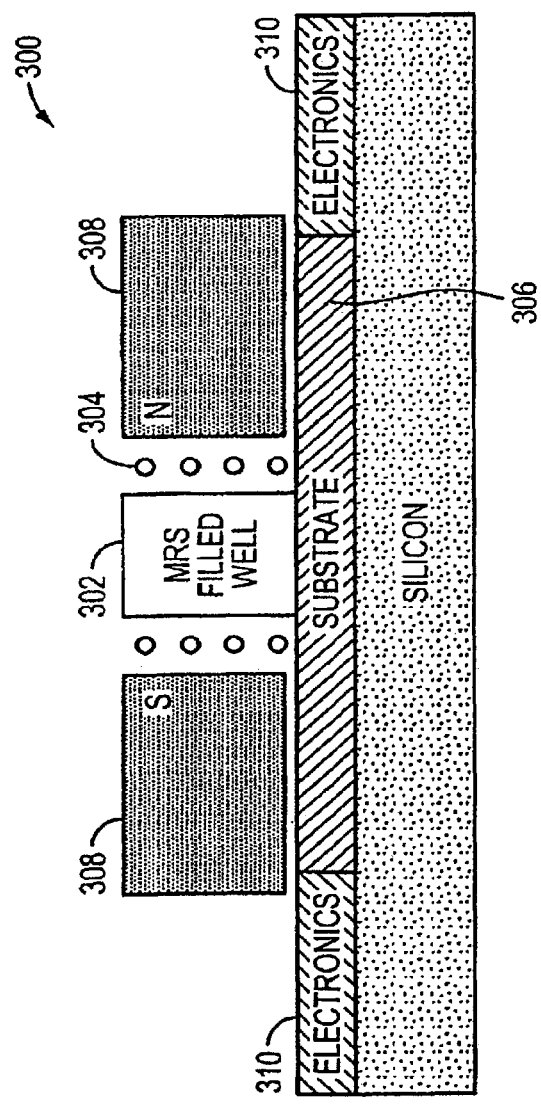
FIG. 3 is a schematic diagram of an NMR system employing magnetic nanoparticles in a micro well for holding a liquid sample, the well surrounded by an RF coil on a substrate (chip), where the magnet for creating the bias magnetic field lies on the substrate, according to an illustrative embodiment of the invention.

FIG. 3 is a schematic diagram 300 of an NMR system employing magnetic nanoparticles in a micro well 302 for holding a liquid sample, the well 302 surrounded by an RF coil 304 on a substrate (chip, support) 306, where a magnet 308 for creating the bias magnetic field lies on the substrate 306. The micro NMR unit 300 may be manufactured using MEMS technology. The well 302 containing the MRS nanoparticles is surrounded by an RF coil 304 which is in turn surrounded by the bias field magnet 308. The permanent magnet sits on a substrate 306. The electronics 310 for the amplification and/or other conditioning of the signal are shown in close proximity to the RF coil 304. This configuration may be fabricated in a MEMS silicon process wherein the coil 304 and magnet 308 are deposited on the surface of the chip and the electronics 310 are made using standard semiconductor manufacturing techniques.

Figure 4A:
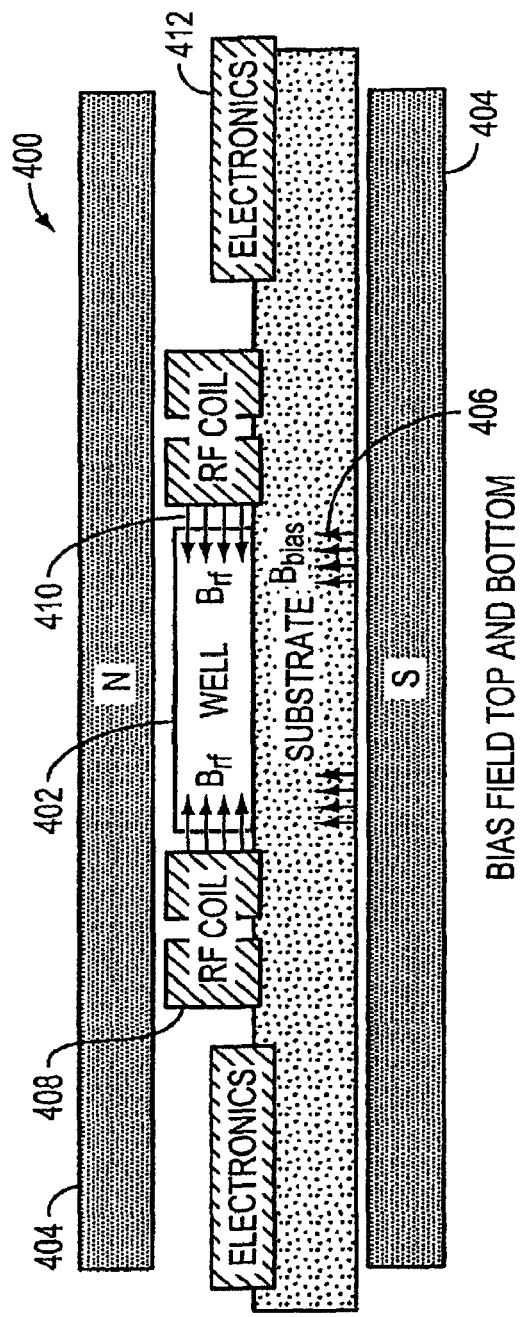
FIG. 4A is a schematic diagram of an NMR system employing magnetic nanoparticles in a micro well, where the magnet for creating a top-to-bottom bias magnetic field does not lie on the chip (the magnet is above and below the well), according to an illustrative embodiment of the invention.

FIG. 4A is a schematic diagram 400 of an NMR system employing magnetic nanoparticles in a micro well 402, where the magnet 404 for creating a top-to-bottom bias magnetic field does not lie on the chip. The magnet 404 is above and below the well 402. The bias field 406 is created by external magnets 404. In order to achieve the high bias magnetic field 406 required for NMR, the bias magnets 404 should be in very close proximity to the well 402 and RF coil 408. This can be accomplished with the micro NMR design, since the dimensions are very small and the permanent magnet can be brought to within 1 mm or less of the well/coil. In this configuration the RF coil may be chosen as a Helmholtz 206 or saddle coil 220 with its primary RF field 410 perpendicular to the bias field 406 created by the two magnets 404. In this configuration the RF coil 408 on the chip provides both the RF excitation and the RF echo sense. The circuitry 412 must switch between excitation mode and sense mode.

Figure 4B:
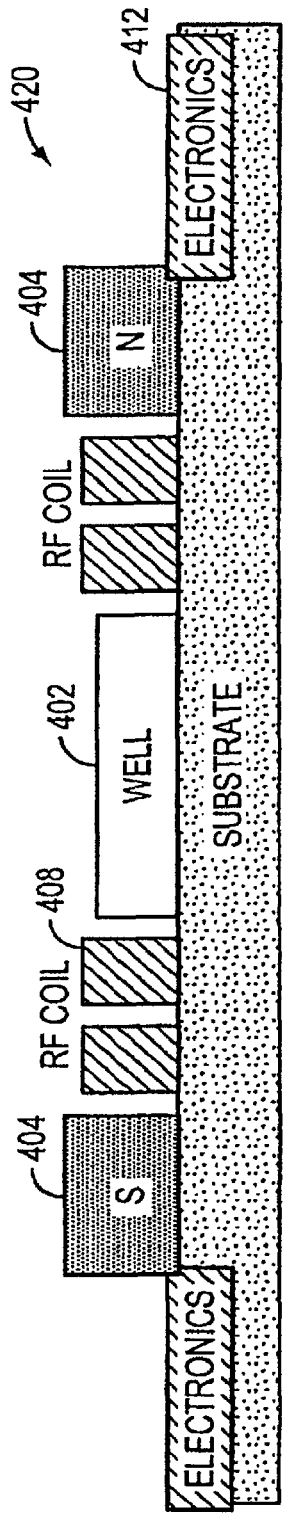
FIG. 4B is a schematic diagram of an NMR system employing magnetic nanoparticles in a micro well, where the magnet for creating a side-to-side bias magnetic field does not lie on the chip (the magnet is adjacent to the well), according to an illustrative embodiment of the invention.

FIG. 4B is a schematic diagram of an NMR system 420 employing magnetic nanoparticles in a micro well 402, where the magnet 404 for creating a side-to-side bias magnetic field does not lie on the chip. The magnet 404 is adjacent to the well 402.

Figure 5A:
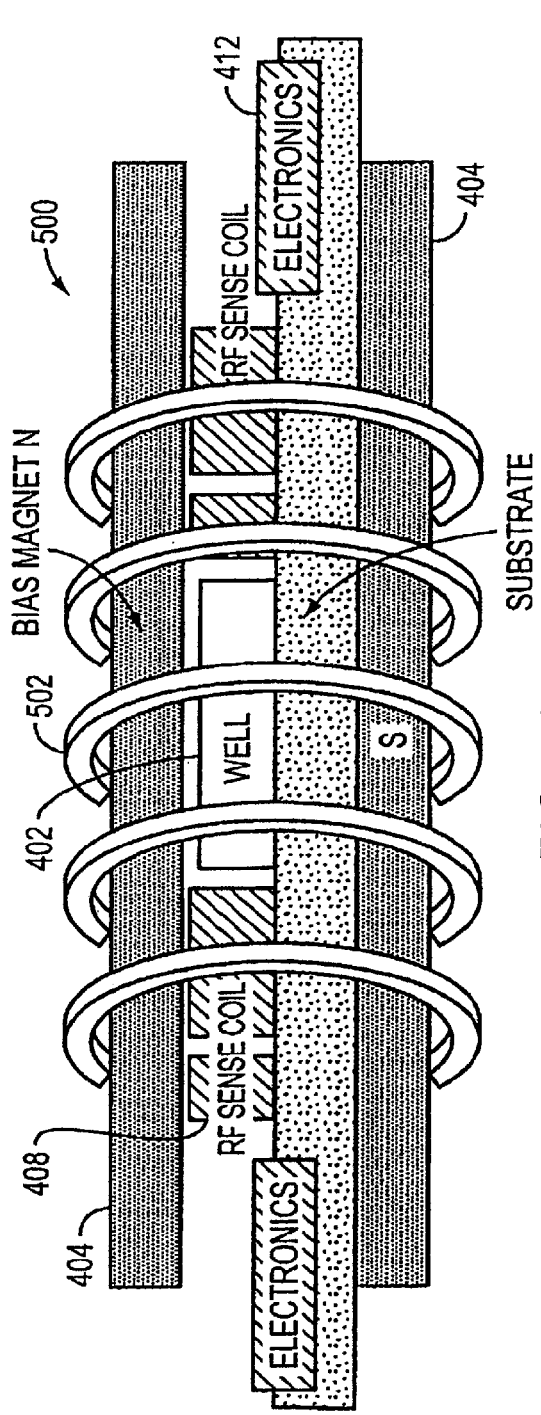
FIG. 5A is a schematic diagram of an NMR system including a single well with external RF excitation coil and external bias magnet, according to an illustrative embodiment of the invention.

FIG. 5A is a schematic diagram of an NMR system 500 including a single well 402 with external RF excitation coil 502. The magnet 404 may be external to the chip, or the magnet 404 may be attached to the chip. The RF excitation in this configuration is provided by the separate and external RF coil 502. This allows for optimization of the excitation RF coil 502 separate from the sense coil 408 on the chip which may be constrained by fabrication limitations (e.g., choice of material, thickness, cross-section, and the like). In this configuration the excitation field is produced by a solenoid 502 winding outside of the micro-NMR unit, which creates a field perpendicular to the bias field created by the bias magnet 404 and in the plane of the RF sense coil 408.

A module approach (as contrasted to the MEMS approach) presents a miniaturization of the NMR configuration 100 of FIG. 1. A liquid sample with the MRS nanoparticles is held in a small tube 108 with the solenoid RF coil 110 wrapped around it and placed within the bias field 104. The advantage of this system with respect to a MEMS system is that larger quantities of sample, or physically larger analyte(s) and/or MRS particles.

Figure 5B:
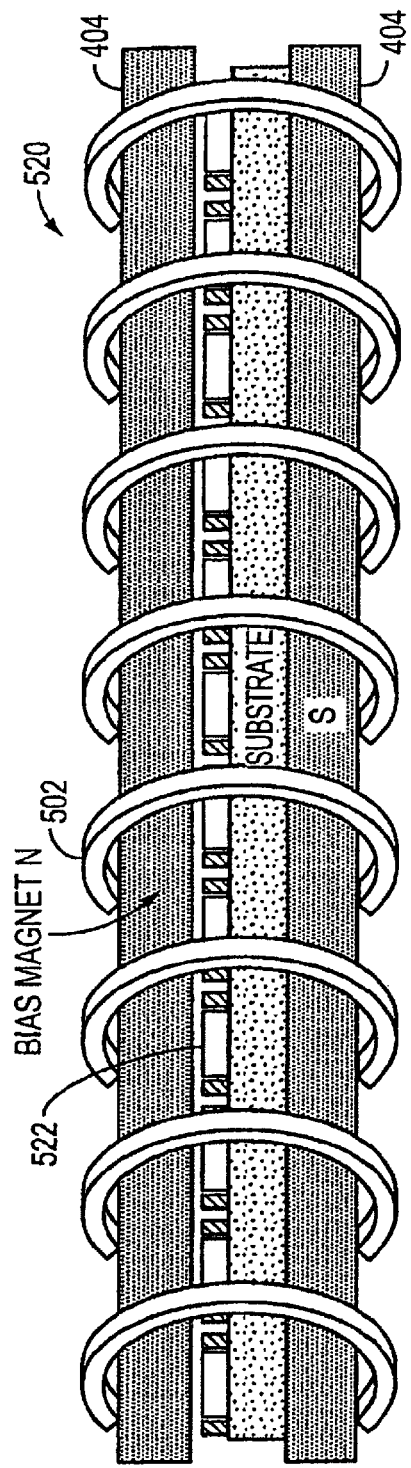
FIG. 5B is a schematic diagram of an NMR system including an array of wells with external RF excitation coil and external bias magnet, according to an illustrative embodiment of the invention.

A panel or array of numerous well/coil units may be used in various embodiments. The panel can have duplicate assay/nanoparticles to enhance sensitivity, accuracy, and/or repeatability of the analyte detection and/or analyte concentration measurements. Multiple assays can perform a variety of diagnostic tests simultaneously. FIG. 5B is a schematic diagram 520 of an NMR system including an array of wells 522 with external RF excitation coil 502 and external bias magnet 404.

Figure 6D:
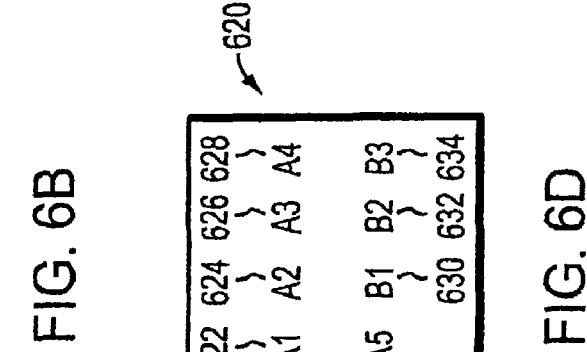
FIG. 6D is a schematic diagram of an NMR system including groups of wells with identical nanoparticles for obtaining multiple data points (redundant measurements) for increased precision, sensitivity, and/or repeatability, according to an illustrative embodiment of the invention.
Figure 6D:
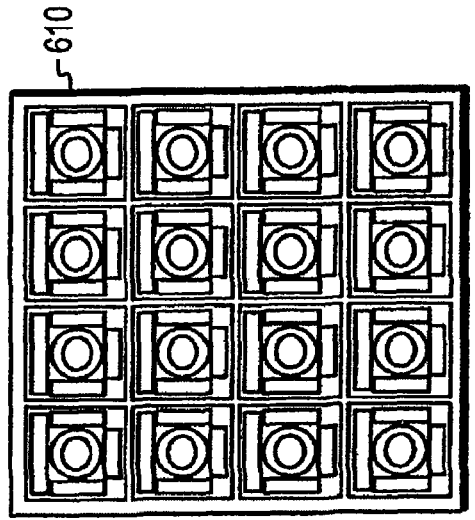
Figure 6C:
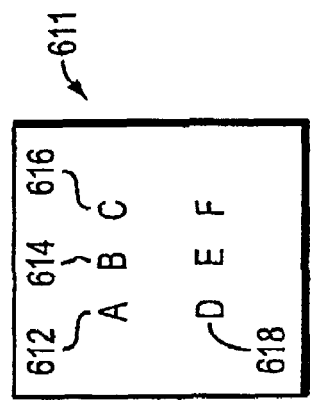
FIG. 6C is a schematic diagram of an NMR system including multiple wells containing different nanoparticles for detection of different analytes, according to an illustrative embodiment of the invention.

Multi-well configurations are shown in FIGS. 6A-D. FIG. 6A shows a single well/coil pair 600. The single well/coil pair 600 is repeated as many times as desired, as shown in the multiple well array 610 in FIG. 6B. FIG. 6C is a schematic 611 of an NMR system including multiple wells containing different nanoparticles customized for detection of different analytes. Different assay nanoparticles are placed in each well 612, 614, 616, 618 to create a test of different analytes. FIG. 6D is a schematic 620 of an NMR system including groups of wells with identical nanoparticles for obtaining multiple data points (redundant measurements) for increased precision, sensitivity, and/or repeatability. Certain assays are duplicated—for example, wells 622, 624, 626, 628 for detection of analyte A, and wells 630, 632, 634 for detection of analyte B, for increased precision, sensitivity, and/or repeatability necessary for certain tests.

Figure 7:
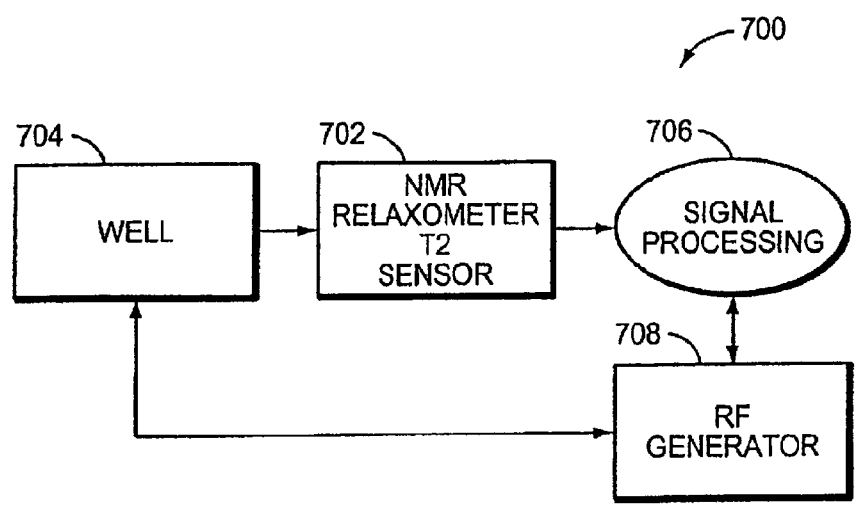
FIG. 7 is a block diagram depicting basic components of an NMR system, including electrical components, according to an illustrative embodiment of the invention.

FIG. 7 is a block diagram depicting basic components of an NMR system 700, including electrical components. The sensor (relaxometer T2 sensor) 702 provides the relaxation echo from the sample well 704 to the signal processing unit 706 while the excitation RF is provided by the RF generator 708.

Figure 8:
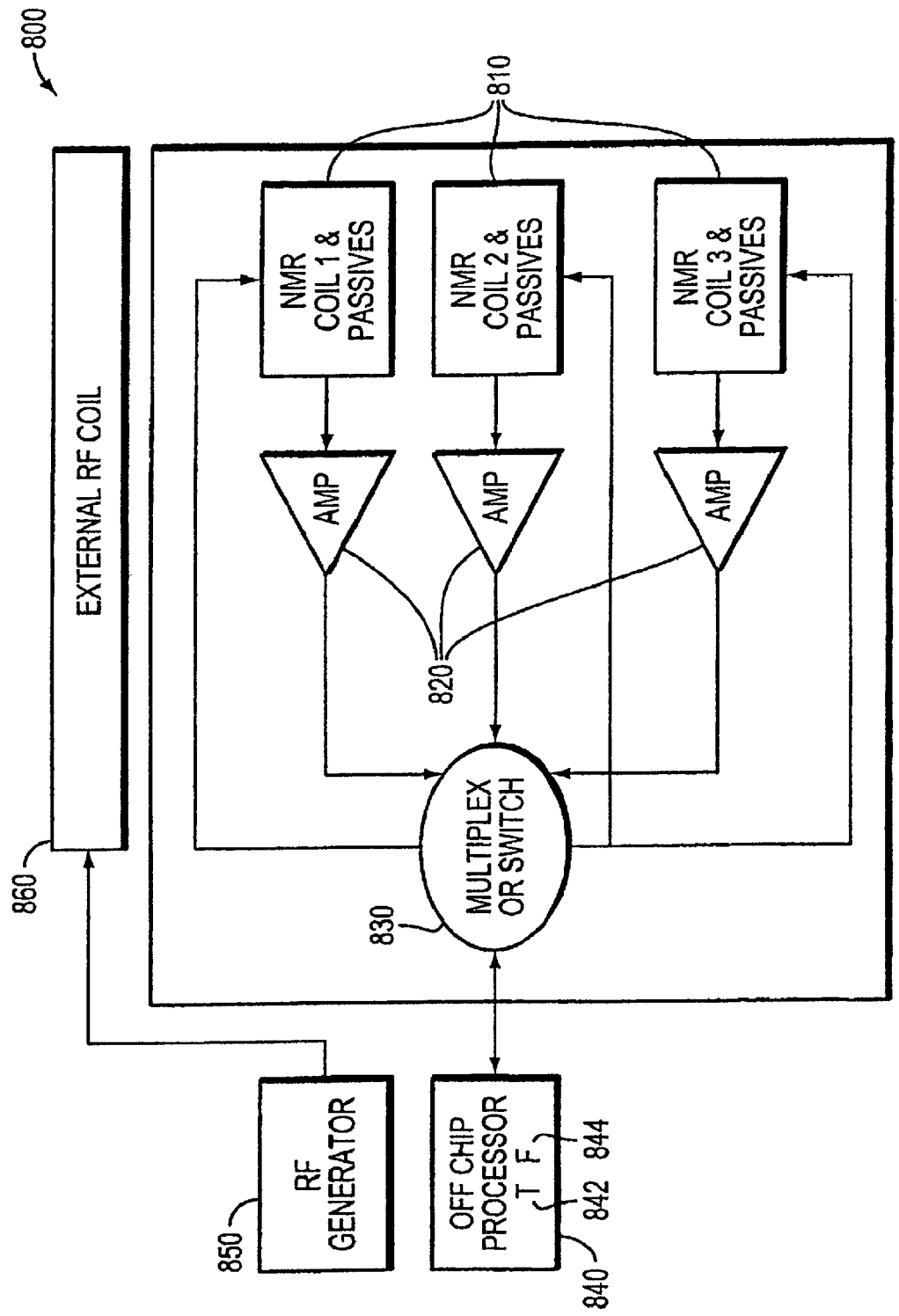
FIG. 8 is a block diagram of an NMR system including multiple wells and sensing coils and an external RF excitation coil, according to an illustrative embodiment of the invention.

FIG. 8 is a block diagram of an NMR system 800 including multiple wells and sensing coils and an external RF excitation coil. The block diagram includes the basic circuit elements in this configuration. The RF sensing coils and associated passives are represented at 810, where the associated passives include inductors, resistors and/or capacitors for the appropriate frequency response from the corresponding well. Each signal is amplified by an on-chip amplifier 820 and either is multiplexed 830 to the off-chip processor 840 or is sequentially switched 860 to the off-chip processor 840. The switching is practical because, for example, with 100 sample wells in sequence, the elapsed processing time would be about 50 seconds or less with a single echo pulse lasting about 500 ms. The off chip processor 840 manages the data and performs both time domain 842 and frequency domain 844 analysis to detect the effects of the nanoparticle aggregation. An RF generator 850 drives the external RF coil 860 at the appropriate Larmor frequency to produce the bias magnet field. The RF generator 850 may or may not be controlled by the off chip processor 840.

Figure 9:
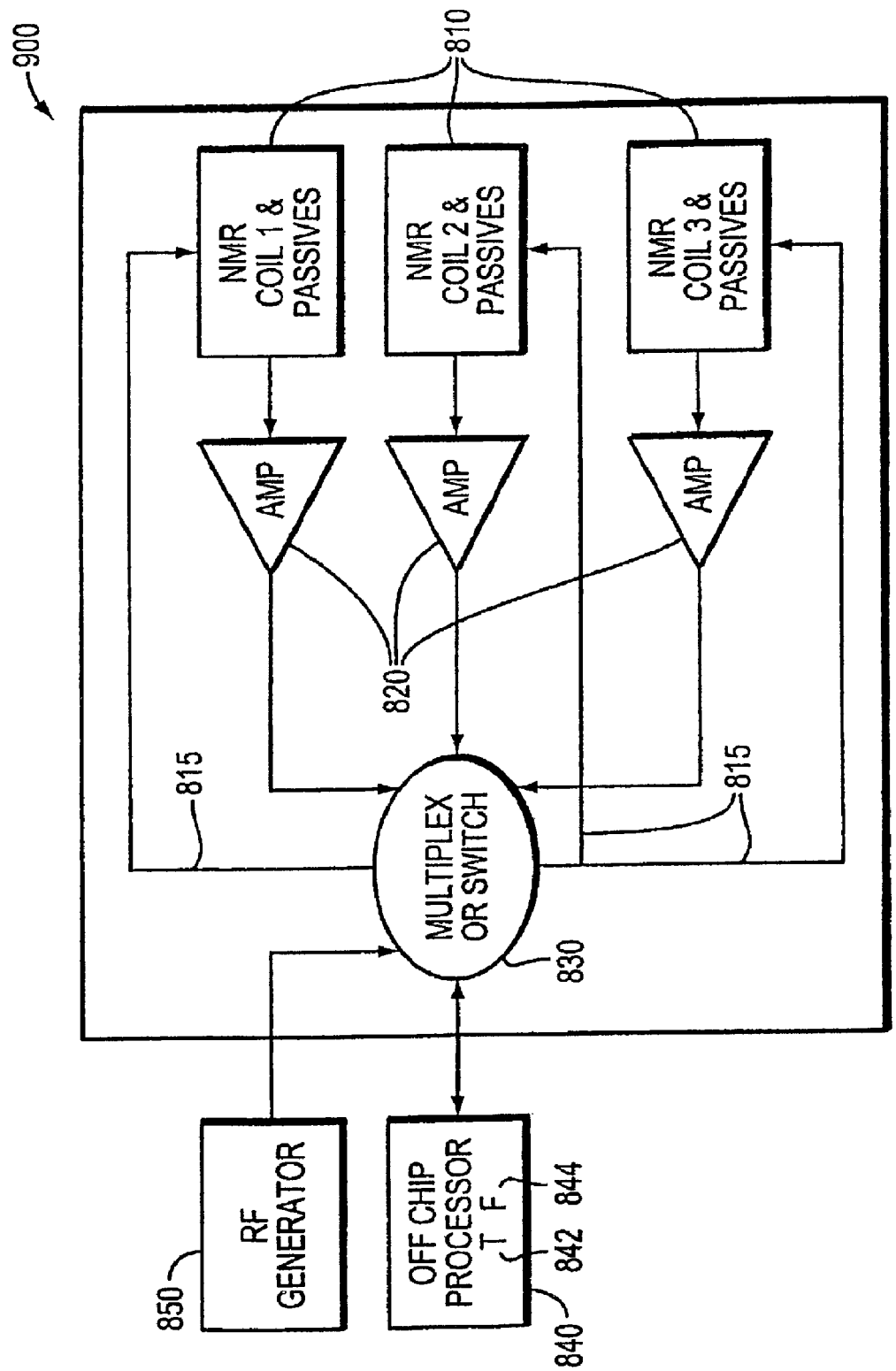
FIG. 9 is a block diagram of an NMR system including multiple wells and sensing coils without an external RF excitation coil (the sensing coils also serve as excitation coils), according to an illustrative embodiment of the invention.

FIG. 9 is a block diagram of an NMR system 900 including multiple wells and sensing coils, but without an external RF excitation coil (the sensing coils also serve as excitation coils). The on-chip elements are the same as in FIG. 8 except that the RF excitation signal must pass through the switch 830 and by pass 815 the amplifier 820 and associated circuitry to go directly to the coil 810.

Figure 10:
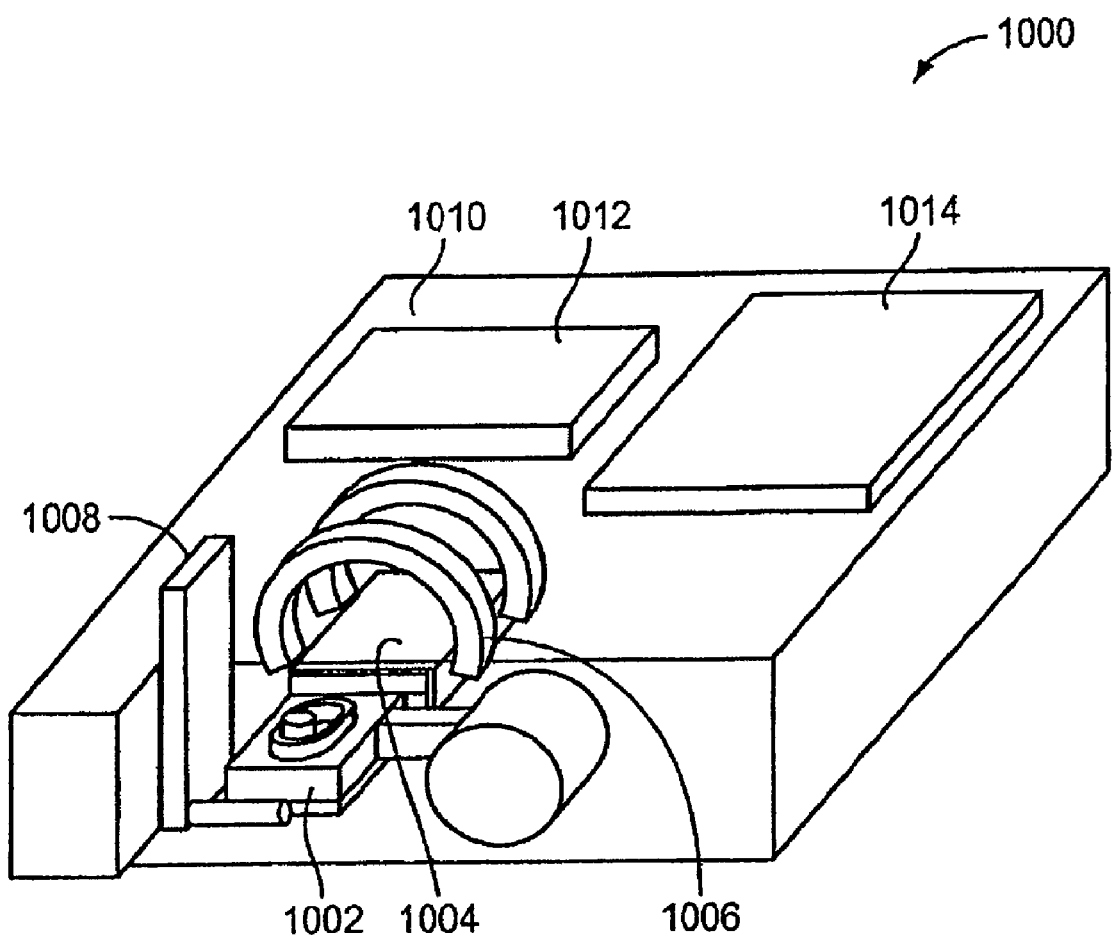
FIG. 10 is a schematic diagram of a chip module receiver/reader, according to an illustrative embodiment of the invention.

The off chip processing may be performed in a reader or similar handheld or desktop device containing the time and frequency domain analysis and the RF generator. The reader may also contain the bias field permanent magnets and/or the RF excitation coil. FIG. 10 is a schematic diagram of the chip or module receiver/reader 1000. The chip or module is positioned onto a sample plate 1002, which is inserted into the slot between the bias field permanent magnets 1004 and within the external excitation coil (if used) 1006. A mechanical slide 1008 is used to push the assay chip or module 1002 into the test slot between the permanent magnets 1004. The reader 1000 may be partially or entirely housed in a case 1010, and may feature an input keypad 1012 and/or a display 1014.

Figure 11:
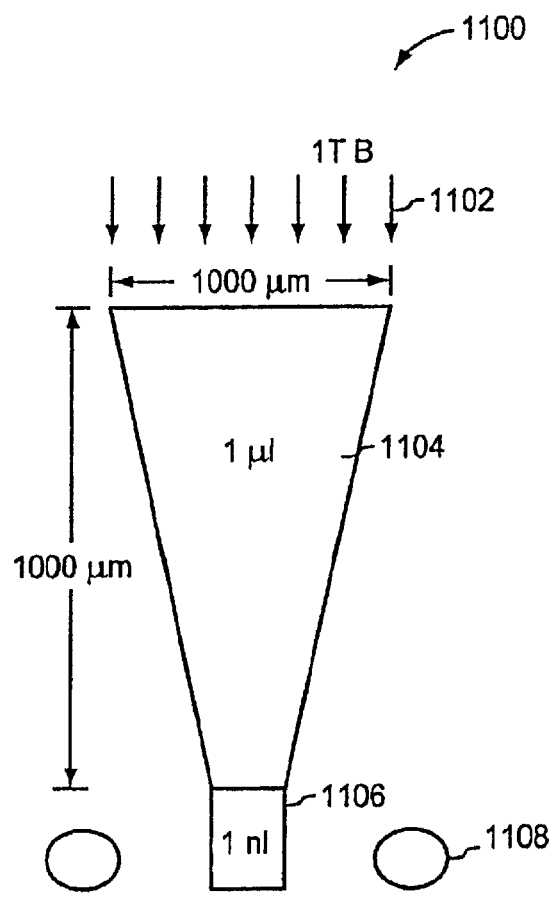
FIG. 11 is a schematic diagram of a magnetic analyte concentrator, according to an illustrative embodiment of the invention.

FIG. 11 is a schematic diagram of a magnetic analyte concentrator 1100, which takes advantage of the effect of the MRS nanoparticles to differentially move target aggregations in the intense magnetic field. The bias magnetic field 1102 will preferentially move the target molecules trapped in the aggregation of the magnetic nanoparticles in the direction of the field from the large cross-section portion 1104 of the well into the small cross-section portion 1106 of the well, thereby concentrating the sample in the area of the RF sense coil 1108. In this example, aggregates occupying a volume of approximately 1 μL are concentrated into a volume of about 1 mL, thereby providing a concentration of approximately 1000 times the original concentration. This results in an increase in sensitivity of the device by about 1000 fold. The magnet(s) and/or magnetic field used to evoke an NMR relaxation response is synergistically used to concentrate the target analyte for improved detection sensitivity. The device may include an array of many micro wells and tiny RF coils surrounding the narrow portions 1106 of these wells.

Figure 12:
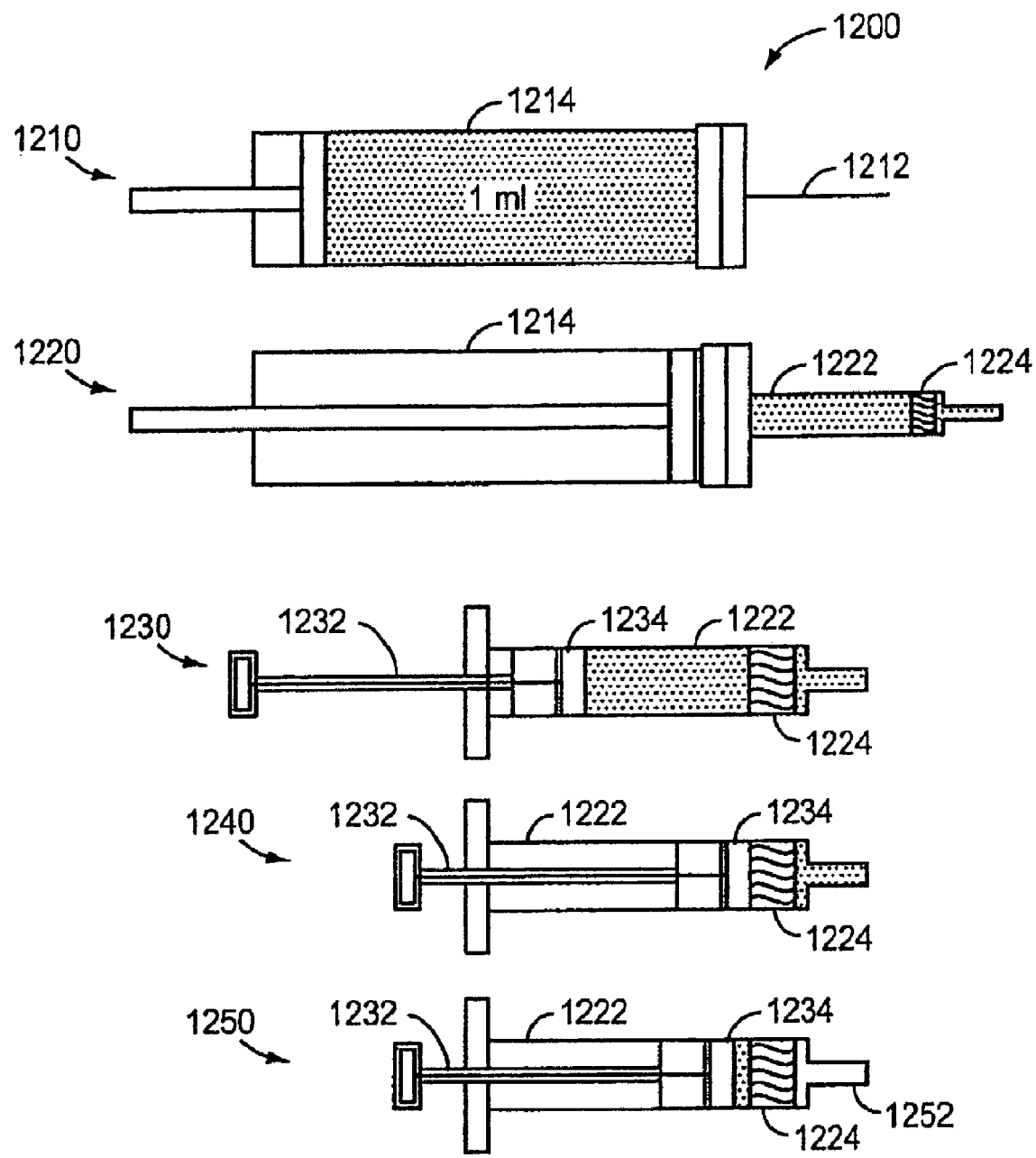
FIG. 12 is a schematic diagram of a syringe analyte concentrator, according to an illustrative embodiment of the invention.

FIG. 12 is a schematic diagram of a syringe analyte concentrator and associated method 1200. This is an additional method for concentrating an analyte for improved sensitivity in the detection of the analyte using the NMR device described herein. It may be used in combination with the magnetic concentrator shown in FIG. 11 and described above. However, the syringe analyte concentrator is not limited to application with nanoparticle aggregation/NMR detection techniques.

In step 1210, a sample is drawn through a needle 1212 into a standard 1 mL syringe 1214. In step 1220, the needle 1212 is removed and a test chamber 1222 is attached. The test chamber has a volume from about 10 to about 400 μL and includes a molecular filter 1224 at the right side of the chamber. The molecular filter 1224 may be, for example, a membrane or molecular sieve made from synthetic compounds, aluminosilicate minerals, clays, porous glass, microporous charcoal, activated carbon, desiccant, lime, silica gel, and/or zeolite. Various molecular filters are available from suppliers such as the Pall Corporation, Millipore Corporation, and Chromacol, for example. The molecular filter 1224 can be used to concentrate DNA, viruses, proteins, and/or other analytes. In step 1230, the test chamber 1222 is detached from the syringe 1214. A plunger 1232 with an integral MEMS chip 1234 at the end having one or more RF coil/well pairs is inserted. In step 1240, remaining fluid is pushed out through the filter 1224. In step 1250, the plunger 1232 is pulled back (to the left) about 1 mm to a detent, thereby drawing fluid held up in the tip 1252 back through the filter 1224 and suspending molecules and nanoparticles. The test chamber 1222 can then be inserted into the reader for NMR testing and analysis. Concentration of analyte depends upon chip size 1234 and syringe cross section. In general, because the MEMS chip is integral to the syringe plunger, the more well/coil pairs in/on the chip, the greater the diameter and the less concentration obtained. For example, where there are 40 wells, with a syringe cross section of 40 mm$^2$ and 1 mm draw back (40 mm$^3$ draw back volume), the concentration is 25 times. Where there are 10 wells, with a syringe cross section of 10 mm$^2$ and 1 mm draw back volume), the concentration is 100 times. Where there is one well, with a syringe cross section of 1 mm$^2$ and 1 mm draw back (1 mm$^3$ draw back volume), the concentration is 1000 times.

Figure 13:
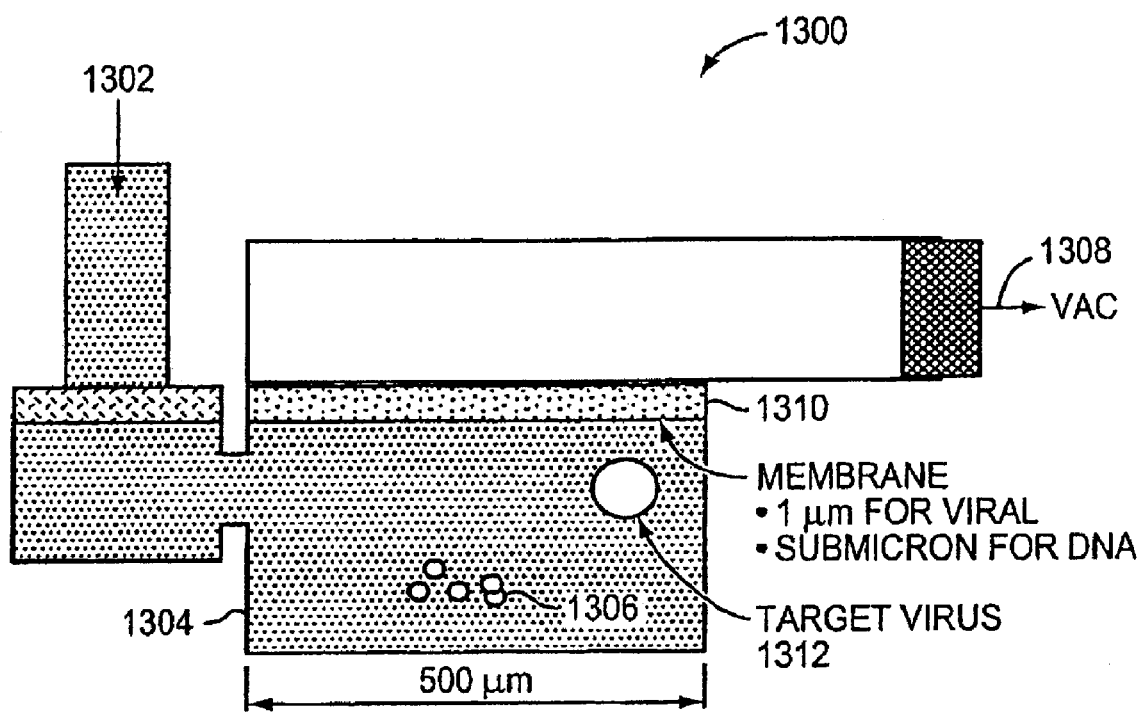
FIG. 13 is a schematic diagram of a membrane analyte concentrator, according to an illustrative embodiment of the invention.

FIG. 13 is a schematic diagram of a membrane analyte concentrator 1300. This is an additional method for concentrating an analyte for improved sensitivity in the detection of the analyte using the NMR device described herein. It may be used in combination with the magnetic concentrator shown in FIG. 11 and/or the syringe concentrator shown in FIG. 12 and described above.

The membrane analyte concentrator 1300 works by forcing an analyte-containing liquid sample 1302 through a chamber 1304 containing nanoparticles 1306 (described herein) via a vacuum 1308. A molecular filter 1310 keeps the molecules of interest in the chamber 1304, thereby concentrating the analyte and improving performance. The chamber 1304 shown in FIG. 13 has a length of about 500 μm. The molecular filter 1310 may be a membrane with pores on the order of about 1 μm for detection of a virus 1312 as analyte, for example, or with submicron pores for the detection of DNA as the analyte.

NMR systems with RF coils and micro wells containing nanoparticle sensors described herein may be designed for detection and/or concentration measurement of specific analyte(s) of interest by development of a model for particle aggregation phenomena and by development of an RF-NMR signal chain model. For example, experiments can be conducted for analyte/nanoparticle systems of interest by characterizing the physics of particle aggregation, including, for example, the effects of affinities, relevant dimensions, and concentrations. Also, experiments can be conducted to characterize the NMR signal(s) (T2, T1, and/or other signal characteristics) as functions of particle aggregation and magnetic particle characteristics. Signal characteristics specific to the MRS (magnetic resonance switch) phenomenon in a given system can be used to enhance detection sensitivity and/or otherwise improve performance. The trade-off between certain design parameters affecting MRS-relaxation T2 (and/or T1) measurement performance may be determined via experimentation; for example, trade offs between filling factor, coil geometries, Q factor, bandwidth, and/or magnetic bias field strength.

Figure 14:
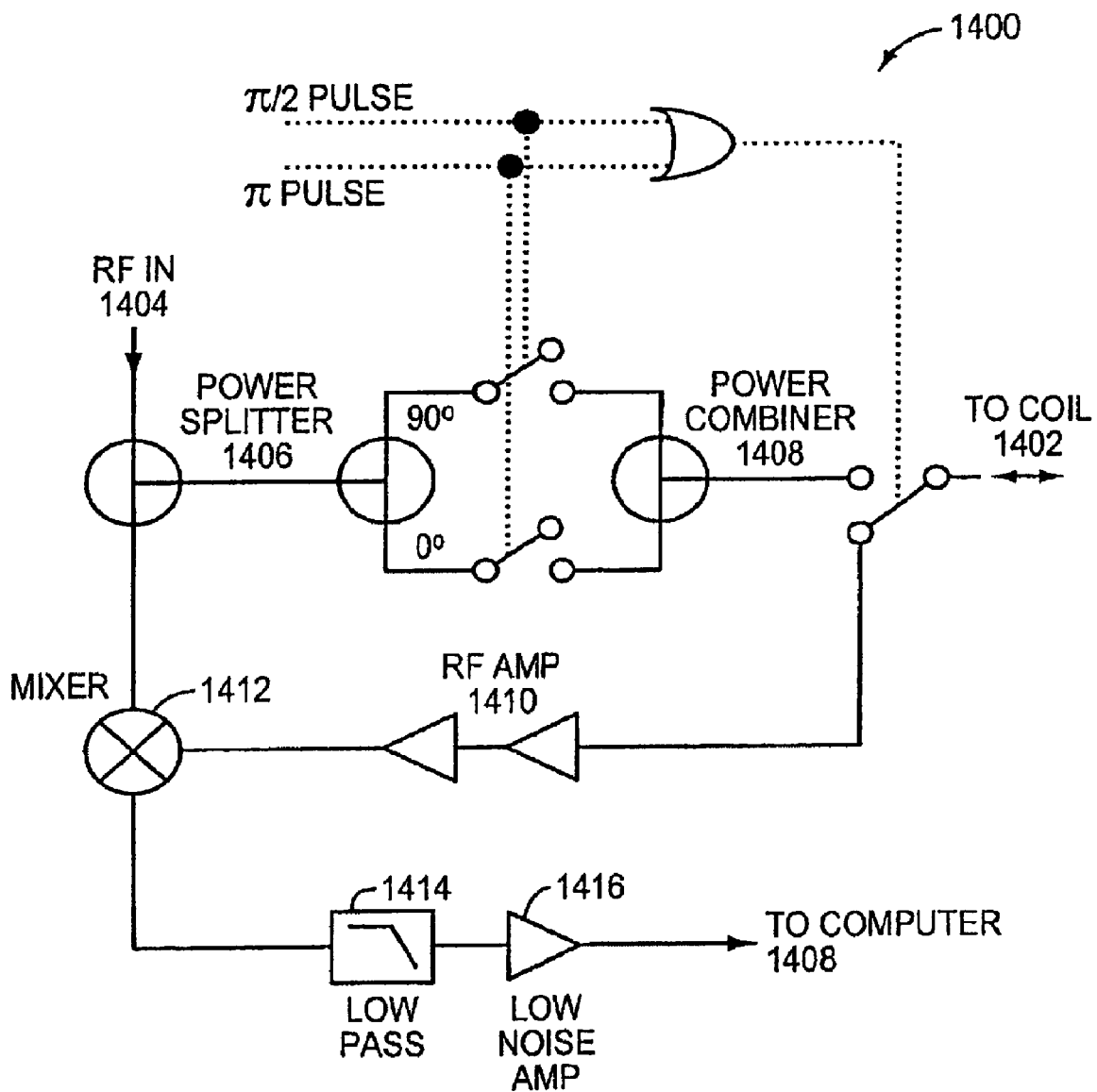
FIG. 14 is a schematic diagram of an electronics set-up for NMR measurement, according to an illustrative embodiment of the invention.

FIG. 14 is a schematic diagram of an electronics set-up 1400 for NMR measurement. The block diagram includes the basic circuit elements in this configuration. The RF sensing coil(s) is/are represented at 1402. An RF pulse generator 1404 provides an RF pulse at or near Larmor frequency. A single pulse may be delivered to the coil 1402, or a series of pulses may be delivered to the coil 1402 via switches. For example, enhanced sensitivity may be achieved for T2 relaxation measurements using multi-echo and/or spin-echo sequences. For example, Carr-Purcell-Meiboom-Gill (CPMG) fast spin-echo (FSE) sequences may achieve greater T2 measurement sensitivity. The RF generator 1404 may or may not be controlled by an off chip processor. A power splitter 1406 and power combiner 1408 are shown in FIG. 14 for delivery of RF excitation to the coil(s) 1402. The signal from each coil is amplified by an RF pre-amplifier 1410 and is processed by a mixer 1412, a low-pass filter 1414, and a low noise amplifier 1416 before signal analysis by the off-chip processor 1408. The signal analysis processor 1408 may alternatively be on-chip. The RF pre-amplifier is preferably in close proximity to the respective coil(s) 1402. The signal analysis processor 1408 manages the data and performs both time domain and frequency domain analysis. Where there are multiple wells, a multiplexer could be used, for example, after conditioning by the RF pre-amplifier 1410. In certain embodiments, the RF coil(s) 1402, RF amplifier(s) 1410, and/or other components shown in the diagram 1400 of FIG. 14 are micromachined, for example, in a BiCMOS (or BiMOS) process, as a system-on-a-chip. BiCMOS refers to the integration of bipolar junction transistors and CMOS (complementary-symmetry/metal-oxide semiconductor) technology into a single device.

In order to maximize power transfer from the RF amplifier 1410, the coil is matched to a given impedance using variable capacitors. During signal detection, the NMR signal from the coil 1402 may be amplified (e.g. by a factor of about 400) by the RF preamplifier 1410, and then down-converted to audio-frequencies by the mixer 1412. The intermediate frequency signal may be amplified (e.g. by a factor of about 100) and filtered for frequencies, for example, above about 30 kHz before being digitized.

The NMR system may include a chip with RF coil(s) and electronics micromachined thereon. For example, the chip may be surface micromachined, such that structures are built on top of a substrate. Where the structures are built on top of the substrate and not inside it, the properties of the substrate are not as important as in bulk micromachining, and expensive silicon wafers used in bulk micromachining can be replaced by less expensive materials such as glass or plastic. Alternative embodiments, however, may include chips that are bulk micromachined. Surface micromachining generally starts with a wafer or other substrate and grows layers on top. These layers are selectively etched by photolithography and either a wet etch involving an acid or a dry etch involving an ionized gas, or plasma. Dry etching can combine chemical etching with physical etching, or ion bombardment of the material. Surface micromachining may involve as many layers as is needed.

Where the relaxation measurement is T2, accuracy and repeatability (precision) will be a function of the signal-to-noise ratio (S/N), the pulse sequence for refocusing (e.g. CPMG, BIRD, Tango, and the like), as well as signal processing factors, such as signal conditioning (e.g. amplification, rectification, and/or digitization of the echo signals), time/frequency domain transformation, and signal processing algorithms used. Signal-to-noise ratio may be a function of the magnetic bias field (B), sample volume, filling factor, coil geometry, coil Q-factor, electronics bandwidth, amplifier noise, and/or temperature, for example.

An illustrative experimental protocol for design or customization of an analyte detection unit for detection of a particular analyte is described below. The illustrative protocol includes performing experiments with a single micro coil, for example, a solenoid would around a capillary tube. Experiments would be conducted to determine how T2 changes as a function of analyte type and concentration, and NMR particle ligand and affinity. Experiments would be conducted to analyze the effect on the T2 signal of the excitation frequency (at and around the Larmor frequency), the pulse sequence, signal conditioning, the bias field (e.g. from about 0.45 T to about 7 T), and Q factor. The effect of Q factor may be determined by performing experiments using coils made from different materials and/or performing and/or by performing experiments at different temperatures, in order to test the effect of coil resistance on the signal quality.

For example, to obtain a 10-fold improvement in the 0.02 ng/mL detection limit for Troponin (10-fold increase in sensitivity), it would be necessary to discern a delta-T2 less than about 5.6 milliseconds from a traditional (non-MRS-measured) T2 of about 100 milliseconds. The minimum signal-to-noise ratio (S/N) would need to be about 20 to detect this difference.

Assuming a target sample volume of 100 nl and a solenoid 542 micron in diameter by 400 micron long, the predicted performance is shown below in Table 1 in the shaded entry. This arrangement provides a predicted robust S/N of 73 and a 0.3 microvolt signal with a 1 T field and 1000 cps bandwidth. S/N increases to a predicted 1300 and 14 microvolts signal with a 7 T field. Varying the coil design to create a higher Q may enhance the performance further. Experiments can be performed at higher magnetic field strengths, e.g. a 7 T field strength provided by commercially available NMR devices, to confirm the viability of system design for achieving the 10-fold increase in the 0.02 ng/mL Troponin detection limit, or 56 femto-molar limit, with a 1 T field.

TABLE 1

Predicted coil performance

| Coil Type Volume in cc | Volume nanoliters | Volume in c micron | Coil Depth microns | Coil Dia micron | Filling Factor Vs/Vc | Turns | Q | Bandwi Tesla cps | S/N | Signal volts | Solenoid |
|---|---|---|---|---|---|---|---|---|---|---|---|
| 1 | 1,000,000 | 1.00E+12 | 11730 | 10,000 | 1 | 1 | 10 | 1000 | 1 | 23,128 | 1.01E−03 |
| 0.1 | 100,000 | 1.00E+11 | 280 | 20,468 | 1 | 1 | 10 | 1000 | 1 | 7,314 | 4.25E−03 |
| 0.01 | 10,000 | 1.00E+10 | 1000 | 3,425 | 1 | 1 | 10 | 1000 | 1 | 2,313 | 1.19E−04 |
| 0.001 | 1,000 | 1.00E+09 | 5000 | 484 | 1 | 1 | 10 | 1000 | 2 | 2,069 | 9.51E−06 |
| 0.0001 | 100 | 1.00E+08 | 400 | 542 | 1 | 1 | 1 | 1000 | 1 | 73 | 2.97E−07 |
| 0.00001 | 10 | 1.00E+07 | 35 | 579 | 1 | 1 | 10 | 1000 | 1 | 73 | 3.40E−06 |
| 0.3 | 300,000 | 3.00E+11 | 20000 | 4,195 | 0.044 | 3 | 10 | 1000 | 0.47 | 856 | 1.18E−04 |
| 0.04 | 40,000 | 4.00E+10 | 20000 | 1,532 | 0.006 | 3 | 10 | 1000 | 0.47 | 114 | 1.58E−05 |
| 0.000002 | 2 | 2.00E+06 | 10 | 484 | 1 | 5 | 8 | 3E+05 | 1 | 2 | 9.51E−06 |
| 0.000001 | 1 | 1.00E+06 | 10 | 342 | 1 | 5 | 15 | 10 | 1 | 283 | 8.92E−06 |

EQUIVALENTS

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A device for the detection of one or more analytes, the device comprising:
   (i) a permanent magnet defining a magnetic field;
   (ii) a support defining a well for holding a liquid sample comprising magnetic particles and the one or more analytes and having an RF coil disposed about the well, the RF coil configured to detect an echo response produced by exposing the liquid sample to a bias magnetic field created using the permanent magnet and an RF excitation;
   (iii) an electrical element in communication with the RF coil, the electrical element configured to amplify, rectify, transmit, and/or digitize the signal corresponding to the echo response; and
   (iv) a removable cartridge sized for convenient insertion into and removal from the device and having a compartment comprising one or more populations of magnetic particles having binding moieties on their surfaces, wherein the binding moieties are operative to alter an aggregation of the magnetic particles in the presence of the one or more analytes.

2. The device of claim 1, wherein the well and the RF coil are configured to provide a filling factor of at least about 0.1.

3. The device of claim 1, wherein the well has a volume of less than about 300 μL.

4. The device of claim 1, wherein the well and the RF coil are configured such that the volume circumscribed by the RF coil is less than about 300 μL.

5. The device of claim 1, wherein the RF coil has a characteristic dimension from about 10 μm to about 1000 μm.

6. The device of claim 1, further comprising a tube for holding the liquid sample, the tube having a varying cross section.

7. The device of claim 1, wherein at least one of the binding moieties is operative to bind to at least one of the following: (i) the one or more analytes; (ii) another of the binding moieties; and (iii) an aggregation-inducing molecule in the liquid sample, thereby producing an aggregate of multiply-linked magnetic particles as a function of the presence or concentration of the one or more analytes in the liquid sample.

8. The device of claim 7, wherein an aggregate of multiply-linked magnetic particles is disaggregated as a function of the presence or concentration of the one or more analytes in the liquid sample.

9. The device of claim 1, wherein the removable cartridge comprises an array of compartments, and wherein magnetic particles having different binding moieties are disposed in different compartments for detection of the one or more analytes, the different binding moieties promoting aggregation or disaggregation of the magnetic particles in the presence of the one or more analytes.

10. The device of claim 9, wherein magnetic particles having different binding moieties are disposed in different compartments for detection of multiple analytes.

11. The device of claim 9, wherein magnetic particles having the same binding moieties are disposed in different compartments for replicate measurements.

12. The device of claim 9, wherein magnetic particles having the same binding moieties are disposed in different compartments for detection of varying analyte concentrations in the liquid sample.

13. The device of claim 1, wherein the liquid sample comprises blood.

14. The device of claim 1, wherein the liquid sample comprises urine.

15. The device of claim 1, wherein one of the one or more analytes is a biologically active substance.

16. The device of claim 15, wherein the biologically active substance is selected from a protein, a peptide, a polypeptide, an amino acid, a nucleic acid, an oligonucleotide, a therapeutic agent, a metabolite of a therapeutic agent, RNA, DNA, an antibody, a carbohydrate, a polysaccharide, glucose, a lipid, a gas, an electrolyte, a lipoprotien, cholesterol, a fatty acid, a glycoprotein, a proteoglycan, and a lipopolysaccharide.

17. The device of claim 16, wherein one of the one or more analytes is a protein.

18. The device of claim 17, wherein the protein is retinol binding protein.

19. The device of claim 17, wherein the peptide is an interleukin.

20. The device of claim 1, wherein the bias magnetic field has a strength of from about 0.45 Tesla to about 7 Tesla.

21. The device of claim 20, further comprising a display for indicating the presence or concentration of the one or more analytes.

22. The device of claim 1, wherein the cartridge is configured for the detection of a particular analyte.

23. The device of claim 22, wherein the cartridge is configured for the detection of a general chemistry analyte.

24. The device of claim 23, wherein the general chemistry analyte is creatinine.

25. The device of claim 22, wherein the particular analyte is an immunosuppressive drug.

26. The device of claim 25, wherein the immunosuppressive drug is tacrolimus.

27. The device of claim 22, wherein the particular analyte is an antifungal drug.

28. The device of claim 27, wherein the antifungal drug is fluconazole.

29. The device of claim 22, wherein the cartridge is configured for the detection of an infectious disease pathogen.

30. The device of claim 29, wherein the infectious disease pathogen is a bacterial, viral, fungal, algal, protozoal, or helminthic pathogen.

31. The device of claim 1, wherein the removable cartridge comprises lyophilized magnetic particles.

32. A method for detecting one or more analytes in a liquid sample, the method comprising:
   (a) placing the liquid sample in a device of claim 1, the device comprising (i) a permanent magnet defining a magnetic field, (ii) a support defining a well for holding a liquid sample comprising magnetic particles and the one or more analytes and having an RF coil disposed about the well, the RF coil configured to detect an echo response produced by exposing the liquid sample to a bias magnetic field created using the permanent magnet and an RF excitation, (iii) an electrical element in communication with the RF coil, the electrical element configured to amplify, rectify, transmit, and/or digitize the signal corresponding to the echo response, and (iv) a removable cartridge sized for convenient insertion into and removal from the device and having a compartment comprising one or more populations of magnetic particles having binding moieties on their surfaces, wherein the binding moieties are operative to alter an aggregation of the magnetic particles in the presence of the one or more analytes;
   (b) contacting the liquid sample with the magnetic particles in the presence of the bias magnetic field;
   (c) exposing the sample to an RF excitation;
   (d) following step (c), detecting an echo response produced by the liquid sample; and
   (e) on the basis of the result of step (d), detecting the one or more analytes.

33. The method of claim 32, further comprising using the result of step (e) to diagnose a medical condition.

34. The method of claim 33, wherein the medical condition is an adverse drug response.

35. The method of claim 33, wherein the medical condition is an infection.

36. The method of claim 33, wherein the medical condition is a renal disorder.

37. The method of claim 33, wherein the medical condition is selected from the group consisting of pain, fever, infection, a cardiac condition, stroke, thrombosis, heart attack, a gastrointestinal disorder, a urinary tract disorder, a skin disorder, a blood disorder, and a cancer.

38. The method of claim 32, wherein one of the one or more analytes is a marker for the detection of a chemical weapon.

39. The method of claim 32, wherein one of the one or more analytes is a marker for the detection of a biological weapon.

40. A method of monitoring one or more analytes in a liquid sample for the diagnosis, management, or treatment of a medical condition in a patient, the method comprising:
   (a) placing the liquid sample in a device of claim 1, the device comprising (i) a permanent magnet defining a magnetic field, (ii) a support defining a well for holding a liquid sample comprising magnetic particles and the one or more analytes and having an RF coil disposed about the well, the RF coil configured to detect an echo response produced by exposing the liquid sample to a bias magnetic field created using the permanent magnet and an RF excitation, (iii) an electrical element in communication with the RF coil, the electrical element configured to amplify, rectify, transmit, and/or digitize the signal corresponding to the echo response, and (iv) a removable cartridge sized for convenient insertion into and removal from the device and having a compartment comprising one or more populations of magnetic particles having binding moieties on their surfaces, wherein the binding moieties are operative to alter an aggregation of the magnetic particles in the presence of the one or more analytes;
   (b) contacting the liquid sample with the magnetic particles in the presence of the bias magnetic field;
   (c) exposing the sample to an RF excitation;
   (d) following step (c), detecting an echo response produced by the liquid sample;
   (e) on the basis of the result of step (d), detecting the one or more analytes; and
   (f) using the result of step (e) to diagnose, manage, or treat the medical condition.

41. The method of claim 40, wherein the monitoring is intermittent.

42. The method of claim 40, wherein the monitoring is continuous.

43. A method of determining an appropriate dose of a therapeutic agent in a patient, the method comprising:
   (a) administering the therapeutic agent to the patient;
   (b) following step (a), obtaining a sample comprising the therapeutic agent or metabolite thereof from the patient;
   (c) placing the liquid sample in a device of claim 1, the device comprising (i) a permanent magnet defining a magnetic field, (ii) a support defining a well for holding a liquid sample comprising magnetic particles and the one or more analytes and having an RF coil disposed about the well, the RF coil configured to detect an echo response produced by exposing the liquid sample to a bias magnetic field created using the permanent magnet and an RF excitation, (iii) an electrical element in communication with the RF coil, the electrical element configured to amplify, rectify, transmit, and/or digitize the signal corresponding to the echo response, and (iv) a removable cartridge sized for convenient insertion into and removal from the device and having a compartment comprising one or more populations of magnetic particles having binding moieties on their surfaces, wherein the binding moieties are operative to alter an aggregation of the magnetic particles in the presence of the one or more analytes;
   (d) contacting the sample with the magnetic particles in the presence of the bias magnetic field;
   (e) exposing the sample to an RF excitation;
   (f) following step (e), detecting an echo response produced by the sample; and
   (g) on the basis of the result of step (f), determining the concentration of the therapeutic agent or metabolite thereof,
wherein, if the concentration of the therapeutic agent or metabolite thereof is above the appropriate therapeutic range, the dose of the therapeutic agent being administered to the patient is reduced, and if the concentration of the therapeutic agent or metabolite thereof is below the therapeutic range, the dose of the therapeutic agent being administered to the patient is increased.

44. The method of claim 43, wherein the determining is intermittent.

45. The method of claim 43, wherein the determining is continuous.

46. The method of claim 32, wherein the well and the RF coil are configured to provide a filling factor of at least about 0.1.

47. The method of claim 32, wherein the well has a volume of less than about 300 μL.

48. The method of claim 32, wherein the well and the RF coil are configured such that the volume circumscribed by the RF coil is less than about 300 μL.

49. The method of claim 32, wherein the RF coil has a characteristic dimension from about 10 μm to about 1000 μm.

50. The method of claim 32, further comprising a tube for holding the liquid sample, the tube having a varying cross section.

51. The method of claim 32, wherein the liquid sample comprises blood.

52. The method of claim 32, wherein the liquid sample comprises urine.

53. The method of claim 32, wherein one of the one or more analytes is a biologically active substance.

54. The method of claim 53, wherein the biologically active substance is selected from a protein, a peptide, a polypeptide, an amino acid, a nucleic acid, an oligonucleotide, a therapeutic agent, a metabolite of a therapeutic agent, RNA, DNA, an antibody, a carbohydrate, a polysaccharide, glucose, a lipid, a gas, an electrolyte, a lipoprotien, cholesterol, a fatty acid, a glycoprotein, a proteoglycan, and a lipopolysaccharide.

55. The method of claim 54, wherein one of the one or more analytes is a protein.

56. The method of claim 55, wherein the protein is retinol binding protein.

57. The method of claim 55, wherein the peptide is an interleukin.

58. The method of claim 32, wherein one of the one or more analytes is a general chemistry analyte.

59. The method of claim 58, wherein the general chemistry analyte is creatinine.

60. The method of claim 32, wherein one of the one or more analytes is an immunosuppressive drug.

61. The method of claim 60, wherein the immunosuppressive drug is tacrolimus.

62. The method of claim 32, wherein one of the one or more analytes is an antifungal drug.

63. The method of claim 62, wherein the antifungal drug is fluconazole.

64. The method of claim 32, wherein one of the one or more analytes is an infectious disease pathogen.

65. The method of claim 64, wherein the infectious disease pathogen is a bacterial, viral, fungal, algal, protozoal, or helminthic pathogen.

66. The method of claim 32, wherein at least one of the binding moieties is operative to bind to at least one of the following: (i) the one or more analytes; (ii) another of the binding moieties; and (iii) an aggregation-inducing molecule in the liquid sample, thereby producing an aggregate of multiply-linked magnetic particles as a function of the presence or concentration of the one or more analytes in the liquid sample.

67. The method of claim 66, wherein an aggregate of multiply-linked magnetic particles is disaggregated as a function of the presence or concentration of the one or more analytes in the liquid sample.

* * * * *

UNITED STATES PATENT AND TRADEMARK OFFICE
CERTIFICATE OF CORRECTION

| | |
|---|---|
| PATENT NO. | : 8,310,232 B2 |
| APPLICATION NO. | : 12/844680 |
| DATED | : November 13, 2012 |
| INVENTOR(S) | : W. D. Lee |

It is certified that error appears in the above-identified patent and that said Letters Patent is hereby corrected as shown below:

In the Specification

Column 15, Line 12, replace "in invention" with --the invention--.

Column 18, Line 45, replace "Helmholz" with --Helmholtz--.

Column 24, Lines 46-47, replace "erythropoitin" with --erythropoietin--.

Column 26, Line 55, replace ".beta.-lactam" with --beta-lactam--.

Column 27, Lines 64-65, replace "anti-gluacoma" with --anti-glaucoma--.

Column 29, Line 9, replace "phenyloin" with --phenytoin--.

Column 30, Line 16, replace "phenyloin" with --phenytoin--;

Line 41, replace "disulfuram" with --disulfiram--.

Column 31, Line 63, replace "antigonists" with --antagonists--.

Column 32, Line 28, replace "gynacology" with --gynecology--.

Column 33, Lines 34-35, replace "fosphenyloin, mephenyloin, and phenyloin" with --fosphenytoin, mephenytoin, and phenytoin--.

Column 34, Line 54, replace "dimentioa" with --dementia--;

Line 56, replace "dysplnea" with --dyspnea--.

Signed and Sealed this
Fifteenth Day of October, 2013

Teresa Stanek Rea
*Deputy Director of the United States Patent and Trademark Office*

CERTIFICATE OF CORRECTION (continued)
U.S. Pat. No. 8,310,232 B2

Column 35, Lines 8-9, replace "megalooblastic" with --megaloblastic--;

Line 16, replace "endocardidtis" with --endocarditis--;

Line 17, replace "peliv" with --pelvic--;

Line 19, replace "actimoyces" with --actinomyces--.

Column 36, Line 3, replace "phenyloin" with --phenytoin--.

Column 37, Line 5, replace "Helmholz" with --Helmholtz--;

Line 19, replace "et al," with --et al.,--;

Line 19, replace "Helmholz" with --Helmholtz--.

Column 38, Line 41, replace "is that larger" with --is the larger--.

Column 40, Line 37, replace "1 mm draw back volume)," with --1 mm draw back (10 mm$^3$ draw back volume),--.

Column 41, Line 10, replace "trade offs" with --trade-offs--.

Column 42, Line 6, replace "acid or a" with --acid, a--;

Line 8, replace "etching, or" with --etching or--;

Line 26, replace "would" with --wound--;

Line 28, replace "concentration, and" with --concentration and--.